United States Patent
Bentley et al.

(10) Patent No.: US 7,323,466 B2
(45) Date of Patent: Jan. 29, 2008

(54) MORPHOLINE DERIVATIVES AS 5HT2C RECEPTOR AGONISTS FOR THE TREATMENT OF OBESITY

(75) Inventors: Jonathan Mark Bentley, Wokingham (GB); Claire Elizabeth Dawson, Wokingham (GB); Wolfgang Guba, Muellheim (DE); Paul Hebeisen, Basel (CH); Nathaniel Monck, Wokingham (GB); Robert Mark Pratt, Wokingham (GB); Hans Richter, Grenzach-Wyhlen (DE); Stephan Roever, Inzlingen (DE); Vicki Ruston, Wokingham (GB)

(73) Assignees: Hoffman-La Roche Inc., Nutley, NJ (US); Vernalis Research Limited, Wokingham (GB)

(*) Notice: Subject to any disclaimer, the term of this patent is extended or adjusted under 35 U.S.C. 154(b) by 112 days.

(21) Appl. No.: 11/332,103

(22) Filed: Jan. 13, 2006

(65) Prior Publication Data
US 2006/0178510 A1 Aug. 10, 2006

(30) Foreign Application Priority Data
Jan. 18, 2005 (EP) .................. 05100281

(51) Int. Cl.
*A61K 31/5375* (2006.01)
*C07D 265/30* (2006.01)
(52) U.S. Cl. .................. 514/238.8; 544/106; 544/170; 514/231.2
(58) Field of Classification Search ................ 544/106, 544/170; 514/231.2, 238.8
See application file for complete search history.

(56) References Cited

U.S. PATENT DOCUMENTS 5,574,030 A * 11/1996 Masaki et al. ......... 514/211.15

5,852,006 A * 12/1998 Masaki et al. .............. 514/183

FOREIGN PATENT DOCUMENTS

| EP | 0435 387 | 7/1991 |
| GB | 1 184 023 | 3/1970 |
| WO | WO 02/22572 | 3/2002 |

OTHER PUBLICATIONS

Brown et al, *J. Pharm. Pharmacol*, vol. 42, (1990) pp. 797-799.
Keller and Wahli: Trends Endocrin. Metab. 1993; 4: 291-296.
Macdonald and Lane: Current Biology vol. 5 pp. 618-621 (1995).

* cited by examiner

*Primary Examiner*—Golam M. M. Shameem
(74) *Attorney, Agent, or Firm*—George W. Johnston; Dennis P. Tramaloni; Brian C. Remy

(57) ABSTRACT

The present invention refers to chemical compounds of formula (I)

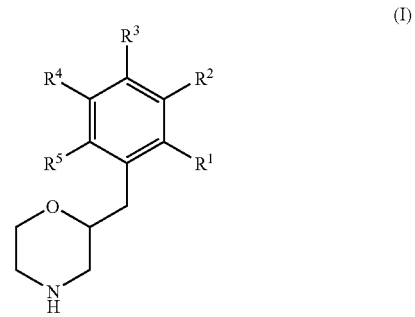

as well as pharmaceutically acceptable salts and esters thereof, wherein $R^1$ to $R^5$ have the significance given in claim 1. These compounds can be used for the preparation of medicaments.

14 Claims, No Drawings

MORPHOLINE DERIVATIVES AS 5HT2C RECEPTOR AGONISTS FOR THE TREATMENT OF OBESITY

PRIORITY TO RELATED APPLICATIONS

This application claims the benefit of European Application No. 05100281.4 filed Jan. 18, 2005, which is hereby incorporated by reference in its entirety.

FIELD OF THE INVENTION

The present invention is directed to new morpholine derivatives, to processes and intermediates for their preparation, to pharmaceutical compositions containing them and to their medicinal use. The active compounds of the present invention are useful in treating obesity and other disorders.

In a preferred embodiment, the invention is directed to compounds of the formula (I):

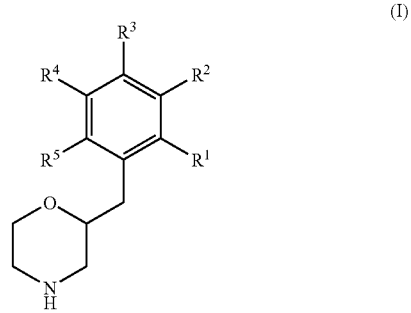

and pharmaceutically acceptable salts and esters thereof.

All documents cited or relied upon below are expressly incorporated herein by reference.

BACKGROUND OF THE INVENTION

It has been recognized that obesity is a disease process influenced by environmental factors in which the traditional weight loss methods of dieting and exercise need to be supplemented by therapeutic products (S. Parker, "*Obesity: Trends and Treatments*", Scrip Reports, PJB Publications Ltd, 1996).

Whether someone is classified as overweight or obese is generally determined on the basis of their body mass index (BMI), which is calculated by dividing body weight (kg) by height squared ($m^2$). Thus, the units of BMI are $kg/m^2$ and it is possible to calculate the BMI range associated with minimum mortality in each decade of life. Overweight is defined as a BMI in the range 25-30 $kg/m^2$, and obesity as a BMI greater than 30 $kg/m^2$. There are problems with this definition in that it does not take into account the proportion of body mass that is muscle in relation to fat (adipose tissue). To account for this, obesity can also be defined on the basis of body fat content: greater than 25% and 30% in males and females, respectively.

As the BMI increases there is an increased risk of death from a variety of causes that is independent of other risk factors. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (XENICAL®) and Sibutramine. Orlistat (a lipase inhibitor) inhibits fat absorption directly and tends to produce a high incidence of unpleasant (though relatively harmless) side-effects such as diarrhoea. Sibutramine (a mixed 5-HT/noradrenalin reuptake inhibitor) can increase blood pressure and heart rate in some patients. The serotonin releaser/reuptake inhibitors fenfluramine (Pondimin®) and dexfenfluramine (Redux™) have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

Diabetes is a disease in which a patient's ability to control glucose levels in blood is impaired, because the ability to respond properly to the action of insulin has been partially lost. In type II diabetes, often referred to as non-insulin dependent diabetes mellitus (NIDDM), which afflicts 80-90% of all diabetic patients in developed countries, the Islets of Langerhans in the pancreas still produce insulin. However, the target organs, mainly muscle, liver and adipose tissue, exhibit a profound resistance to insulin stimulation, thus the body compensates by producing abnormally high levels of insulin. In the later stages of the disease, however, insulin secretion decreases due to exhaustion of the pancreas.

Current first line treatment for diabetes generally involves adoption of a diet low in fat and glucose and taking regular exercise. However, compliance can be moderate and as the disease progresses, treatment with hypoglycemic drugs, e.g. sulfonylureas or metformin, becomes necessary. A promising new class of drugs has recently been introduced that resensitize patients to their own insulin (insulin sensitizers), thereby reverting blood glucose and triglyceride levels to normal, and thus abolishing, or at least reducing, the requirement for exogenous insulin. Troglitazone (Resulin™) and rosiglitazone (Avandia™) belong to the thiazolidinediones (TZD) class of PPARγ-agonists and were the first representatives of the class approved for NIDDM treatment in several countries. These compounds, however, suffer from side effects including rare but severe liver toxicity (as seen with troglitazone), and increased body weight in humans. Therefore, new, better and more efficacious drugs for the treatment of conditions involving hyperglycemia, particularly NIDDM are urgently needed. Recent studies provided evidence that coagonism of PPARα and PPARγ would result in compounds with enhanced therapeutic potential, i. e. with an improved lipid profile effect on top of the normalization of glucose- and insulin-levels (Keller and Wahli: Trends Endocrin. Metab. 1993; 4: 291-296, Macdonald and Lane: Current Biology Vol. 5 pp. 618-621 (1995)).

The novel compounds of the present invention can be used as efficacious drugs for the treatment and prevention of diabetes, particularly of non-insulin dependent diabetes mellitus.

SUMMARY OF THE INVENTION

In an embodiment of the present invention, provided is a compound of formula (I):

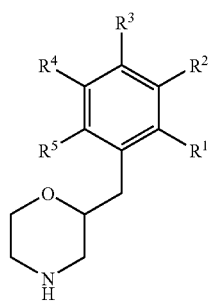

(I)

wherein $R^1$, $R^2$, $R^3$, $R^4$ and $R^5$ are independently selected from hydrogen, alkyl, cycloalkyl, aryl, halogen, cyano, alkoxy, hydroxy, arylalkyl, arylalkoxy, alkenylalkoxy, cycloalkylalkoxy, cycloalkylalkoxyalkyl, hydroxyalkyl, alkoxyalkyl, hydroxyalkoxy, alkoxyalkoxy, alkenyl, alkenyloxy, N-hydroxy-amidinyl, aryloxyalkoxyalkyl, cyanoalkyl, cyanoalkoxy, alkinyloxy, alkinylalkoxy, heterocyclyl, heterocyclylalkyl, heterocyclylalkoxy, arylheterocyclylalkoxy, haloalkylarylheterocyclylalkoxy, haloalkylheterocyclylalkoxy, aralkylheterocyclylalkoxy, haloalkyl, alkylcarbonyl, alkylsulfonylphenyl, alkylsulfanyl, haloalkoxy and haloalkoxy substituted with hydroxyl and, wherein two of $R^1$, $R^2$, $R^3$, $R^4$ and $R^5$ optionally form together —$(CH_2)_n$—O— or —O—$CF_2$—O—;

n is 1, 2, 3 or 4;

with the proviso that at least one of $R^1$, $R^2$, $R^3$, $R^4$ and $R^5$ is not hydrogen and 2-(4-tert-butyl-benzyl)-morpholine is excluded;

and pharmaceutically acceptable salts and esters thereof.

In another embodiment of the present invention, provided is a process for the preparation of a compound of formula I, comprising one of the following reactions: reaction of a compound according to formula (B2) in the presence of a base and ethanolamine-O-sulfate in order to obtain a compound according to formula (I)

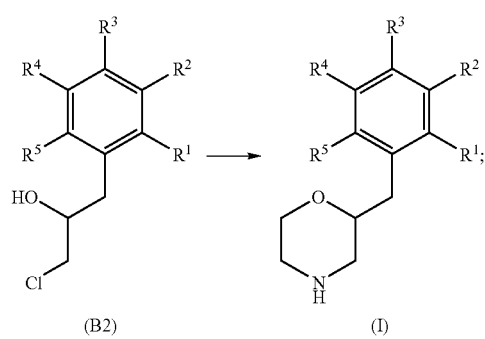

reaction of a compound (M3) in the presence of a compound (M2) in order to form a compound (M4) which is transformed into a compound of the formula I by cleaving of the protecting group PG;

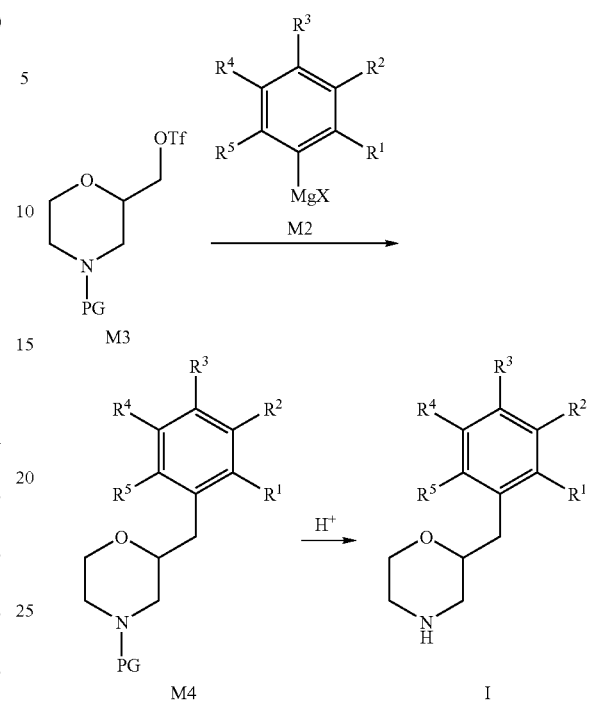

PG means a protecting group;
Tf means the triflic group.

In a further embodiment of the present invention, provided is a pharmaceutical composition, comprising a therapeutically effective amount of a compound according to formula (I) and a therapeutically inert carrier.

In a yet another embodiment of the present invention, provided is a method for the treatment and prophylaxis of disorders of the central nervous system, cardiovascular disorders, gastrointestinal disorders, diabetes insipidus, and sleep apnoea, comprising the step of administering a therapeutically effective amount of a compound according to formula (I) to a patient in need thereof.

In a yet further embodiment of the present invention, provided is a method for the treatment and prophylaxis of eating disorders and obesity, comprising the step of administering a therapeutically effective amount of a compound according to formula (I) to a patient in need thereof.

In a still another embodiment of the present invention, provided is a method for the treatment and prophylaxis of disorders selected from diabetes mellitus, Type I diabetes, Type II diabetes, diabetes secondary to pancreatic disease, diabetes related to steroid use, Type III diabetes, hyperglycemia, diabetic complications and insulin resistance, comprising the step of administering a therapeutically effective amount of a compound according to formula (I) to a patient in need thereof.

In a still yet further embodiment of the present invention, provided is a method of treatment of obesity in a human in need of such treatment, comprising the step of administering to said human a therapeutically effective amount of a compound according to formula (I) and a therapeutically effective amount of a lipase inhibitor.

DETAILED DESCRIPTION

In the present description the term "alkyl", alone or in combination, signifies a straight-chain or branched-chain alkyl group with 1 to 8 carbon atoms, preferably a straight or branched-chain alkyl group with 1-4 carbon atoms. Examples of straight-chain and branched $C_1$-$C_8$ alkyl groups are methyl, ethyl, propyl, isopropyl, butyl, isobutyl, tert-butyl, the isomeric pentyls, the isomeric hexyls, the isomeric heptyls and the isomeric octyls, preferably methyl, ethyl, propyl and isopropyl. Particularly preferred are methyl and ethyl.

The term "cycloalkyl", alone or in combination, signifies a cycloalkyl ring with 3 to 8 carbon atoms and preferably a cycloalkyl ring with 3 to 6 carbon atoms. Examples of $C_3$-$C_8$ cycloalkyl are cyclopropyl, methyl-cyclopropyl, dimethyl-cyclopropyl, cyclobutyl, methyl-cyclobutyl, cyclopentyl, methyl-cyclopentyl, cyclohexyl, methylcyclohexyl, dimethyl-cyclohexyl, cycloheptyl and cyclooctyl, preferably cyclopropyl and cyclopentyl and particularly cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert-butoxy, preferably methoxy and ethoxy.

The term "cycloalkoxy", alone or in combination, signifies a group of the formula cycloalkyl-O— in which the term "cycloalkyl" has the previously given significance.

The term "hydroxyalkyl", alone or in combination, signifies an alkyl group as previously defined, wherein one or several hydrogen atoms, preferably one hydrogen atom has been replaced by a hydroxyl group. Examples are hydroxymethyl, hydroxyethyl and 2-hydroxyethyl.

The term "alkyl substituted with halogen", alone or in combination, signifies an alkyl group as previously defined, wherein one or several hydrogen atoms, preferably one to three hydrogen atoms have/has been replaced by halogen. Examples of haloalkyl groups are trifluoromethyl, trifluoroethyl, pentafluoroethyl and trichloromethyl. Preferred examples are monofluoromethyl, difluoromethyl and trifluoromethyl. Particularly preferred is fluoromethyl and difluoromethyl.

The term "carbonyl" refers to a group of the formula —C(O)—.

The term "aryl", alone or in combination, signifies a phenyl or naphthyl group which optionally carries one to three substituents each independently selected from alkyl, alkoxy, halogen, carboxy, alkoxycarbonyl, aminocarbonyl, hydroxy, amino, nitro and the like, such as phenyl, p-tolyl, 4-methoxyphenyl, 4-tert-butoxyphenyl, 4-fluorophenyl, 2-chlorophenyl, 3-chlorophenyl, 4-chlorophenyl, 4-hydroxyphenyl, 1-naphthyl and 2-naphthyl. Preferred is phenyl.

The term "aralkyl", alone or in combination, signifies an alkyl or cycloalkyl group, preferably an alkyl group as previously defined in which one or several, preferably one hydrogen atom has been replaced by an aryl group as defined before. Preferred is benzyl.

The term "aralkoxy", alone or in combination, signifies a group of the formula aralkyl-O— in which the term "aralkyl" has the previously given significance.

The term "heterocyclyl", alone or in combination signifies a saturated, partially unsaturated or aromatic 5- to 10-membered heterocycle, which contains one or more hetero atoms selected from nitrogen, oxygen and sulphur. If desired, it can be substituted on one or more carbon atoms e.g. by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e. =N—) by oxido, with halogen, alkyl, cycloalkyl and alkoxy being preferred. Examples of such heterocyclyl groups are pyrrolidinyl, piperidinyl, piperazinyl, morpholinyl, thiomorpholinyl, pyrazoyl, imidazoyl (e.g. imidazol-4-yl and 1-benzyloxycarbonyl-imidazol-4-yl), pyrazoyl, pyridyl, pyrazinyl, pyrimidinyl, hexahydro-pyrimidinyl, furyl, thienyl, thiazolyl, oxazolyl, indolyl (e.g. 2-indolyl), quinolyl (e.g. 2-quinolyl, 3-quinolyl and 1-oxido-2-quinolyl), isoquinolyl (e.g. 1-isoquinolyl and 3-isoquinolyl), tetrahydroquinolyl (e.g. 1,2,3,4-tetrahydro-2-quinolyl), 1,2,3,4-tetrahydroisoquinolyl (e.g. 1,2,3,4-tetrahydro-1-oxo-isoquinolyl) and quinoxalinyl. Preferred examples are pyridyl, chloro-pyridyl and methyl-isoxazolyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —NH$_2$, methylamino, ethylamino, dimethylamino, diethylamino, methyl-ethylamino, morpholin-1-yl, pyrrolidin-1-yl or piperidinyl etc., preferably amino, dimethylamino and diethylamino and particularly primary amino.

The term "halogen" signifies fluorine, chlorine, bromine or iodine and preferably fluorine, chlorine or bromine and particularly fluorine and chlorine.

The term "carboxy", alone or in combination, signifies a —COOH group.

The term "cyano", alone or in combination, signifies a —CN group.

The term "alkylsulfanyl", alone or in combination, signifies an alkyl-S— group, wherein the term "alkyl" is defined as before.

The term "sulfonyl", alone or in combination, signifies a —SO$_2$—group.

The term "oxy", alone or in combination, signifies an —O— group.

The term "alkenyl", alone or in combination, signifies a straight-chain or branched-chain hydrocarbon group comprising a carbon carbon double bond and 2 to 10, preferably 2 to 8 carbon atoms, more preferably 2 to 4 carbon atoms such as e.g. but-2-enyl, allyl and vinyl.

The term "alkinyl", alone or in combination, signifies a straight-chain or branched-chain hydrocarbon group comprising a carbon carbon tripple bond and 2 to 10, preferably 2 to 8 carbon atoms, more preferably 2 to 4 carbon atoms such as e.g. ethynyl and propynyl.

The term "haloalkyl", alone or in combination, means an alkyl group as defined before, wherein one or more, preferably 1 to 5, particularly 1 to 3 hydrogen atoms are replaced by halogen such as e.g. trifluoromethyl, difluoromethyl and pentafluoroethyl.

The term "haloalkoxy", alone or in combination, signifies a group of the formula haloalkyl-O— in which the term "haloalkyl" has the previously given significance.

The term "pharmaceutically acceptable salts" refers to those salts which retain the biological effectiveness and properties of the free bases or free acids, which are not biologically or otherwise undesirable. Preferred are the salts which are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like.

In addition "pharmaceutically acceptable salts" may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. The compound of formula I can also be present in the form of zwitterions.

The invention expressly includes pharmaceutically usable solvates of compounds according to formula I. The compounds of formula I can be solvated, e.g. hydrated. The solvation can be effected in the course of the manufacturing process or can take place, e.g. as a consequence of hygroscopic properties of an initially anhydrous compound of formula I (hydration). The term pharmaceutically acceptable salts also includes pharmaceutically usable solvates.

"Pharmaceutically acceptable esters" means that compounds of general formula (I) may be derivatized at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

In more detail, for example, the COOH groups of compounds according to formula I can be esterified. The alkyl and aralkyl esters are examples of suitable esters. The methyl, ethyl, propyl, butyl and benzyl esters are preferred esters. The methyl and ethyl esters are especially preferred. Further examples of pharmaceutically usable esters are compounds of formula I, wherein the hydroxy groups can be esterified. Examples of such esters are formate, acetate, propionate, butyrate, isobutyrate, valerate, 2-methylbutyrate, isovalerate and N,N-dimethylaminoacetate. Preferred esters are acetate and N,N-dimethylaminoacetate.

The invention expressly includes prodrugs of compounds according to formula I.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragées and hard gelatin capsules are lactose, other sugars and sugar alcohols like sorbitol, mannitol, maltodextrin, or other fillers; surfactants like sodium lauryl sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

Preferred are the compounds according to formula I and their pharmaceutically acceptable salts. Preferred salts are the hydrochloride salts. Particularly preferred are the compounds according to formula I.

Preferred are compounds of formula I, wherein $R^1$, $R^2$, $R^3$, $R^4$ and $R^5$ are independently selected from hydrogen, alkyl, cycloalkyl, halogen, cyano, alkoxy, hydroxy, arylalkyl, arylalkoxy, alkenylalkoxy, cycloalkylalkoxy, cycloalkylalkoxyalkyl, hydroxyalkyl, alkoxyalkyl, hydroxyalkoxy, alkoxyalkoxy, alkenyl, alkenyloxy, N-hydroxyamidinyl, aryloxyalkoxyalkyl, cyanoalkyl, cyanoalkoxy, alkinyloxy, alkinylalkoxy, heterocyclyl, heterocyclylalkyl, heterocyclylalkoxy, haloalkyl, alkylcarbonyl, haloalkoxy and haloalkoxy substituted with hydroxyl and, wherein two of $R^1$, $R^2$, $R^3$, $R^4$ and $R^5$ optionally form together —$(CH_2)_n$—O— or —O—$CF_2$—O— and, with the proviso that at least one of $R^1$, $R^2$, $R^3$, $R^4$ and $R^5$ is not hydrogen and 2-(4-tert-butyl-benzyl)-morpholine is excluded.

Preferred are compounds of formula I, wherein $R^1$, $R^2$, $R^3$, $R^4$ and $R^5$ are independently selected from hydrogen, alkyl, cycloalkyl, halogen, cyano, alkoxy, hydroxy, arylalkyl, arylalkoxy, alkenylalkoxy, cycloalkylalkoxy, cycloalkylalkoxyalkyl, hydroxyalkyl, alkoxyalkyl, hydroxyalkoxy, alkoxyalkoxy, alkenyl, alkenyloxy, N-hydroxyamidinyl, aryloxyalkoxyalkyl, cyanoalkyl, cyanoalkoxy, alkinyloxy, alkinylalkoxy, heterocyclyl, heterocyclylalkyl, heterocyclylalkoxy, haloalkyl, alkylcarbonyl and haloalkoxy and, wherein two of $R^1$, $R^2$, $R^3$, $R^4$ and $R^5$ optionally form together —$(CH_2)_n$—O— or —O—$CF_2$—O— and, with the proviso that at least one of $R^1$, $R^2$, $R^3$, $R^4$ and $R^5$ is not hydrogen and 2-(4-tert-butyl-benzyl)-morpholine is excluded.

Further preferred are those compounds of formula I, wherein $R^1$, $R^2$, $R^3$, $R^4$ and $R^5$ are independently selected from hydrogen, alkyl, halogen, cyano, alkoxy, hydroxy, arylalkyl, arylalkoxy, alkenylalkoxy, cycloalkylalkoxy, cycloalkylalkoxyalkyl, hydroxyalkyl, alkoxyalkyl, hydroxyalkoxy, alkoxyalkoxy, alkenyl, alkenyloxy, N-hydroxy-amidinyl, aryloxyalkoxyalkyl, cyanoalkyl, cyanoalkoxy, alkinyloxy, alkinylalkoxy, heterocyclyl, heterocyclylalkyl, heterocyclylalkoxy, haloalkyl, alkylcarbonyl and haloalkoxy and, wherein two of $R^1$, $R^2$, $R^3$, $R^4$ and $R^5$ optionally form together —$(CH_2)_n$—O— or —O—$CF_2$—O— and, with the proviso that at least one of $R^1$, $R^2$, $R^3$, $R^4$ and $R^5$ is not hydrogen and 2-(4-tert-butyl-benzyl)-morpholine is excluded.

Also preferred are those compounds according to formula I, wherein $R^1$, $R^2$, $R^3$, $R^4$ and $R^5$ are independently selected from hydrogen, alkyl, halogen, cyano, alkoxy, hydroxy, arylalkyl, arylalkoxy, alkenylalkoxy, cycloalkylalkoxy, cycloalkylalkoxyalkyl, hydroxyalkyl, alkoxyalkyl, hydroxyalkoxy, alkoxyalkoxy, alkenyl, alkenyloxy, N-hydroxy-amidinyl, aryloxyalkoxyalkyl, cyanoalkyl, cyanoalkoxy, alkinyloxy, alkinylalkoxy, heterocyclyl, heterocyclylalkyl, heterocyclylalkoxy, haloalkyl, alkylcarbonyl and haloalkoxy and, wherein two of $R^1$, $R^2$, $R^3$, $R^4$ and $R^5$ optionally form together —$(CH_2)_n$—O— and, with the proviso that at least one of $R^1$, $R^2$, $R^3$, $R^4$ and $R^5$ is not hydrogen and 2-(4-tert-butyl-benzyl)-morpholine is excluded.

Further preferred are those compounds according to formula I, wherein $R^1$, $R^2$, $R^3$, $R^4$ and $R^5$ are independently selected from hydrogen, alkyl, halogen, cyano, alkoxy, hydroxy, arylalkyl, arylalkoxy, alkenylalkoxy, cycloalkylalkoxy, cycloalkylalkoxyalkyl, hydroxyalkyl, alkoxyalkyl, hydroxyalkoxy, alkoxyalkoxy, alkenyl, alkenyloxy, N-hydroxy-amidinyl, aryloxyalkoxyalkyl, cyanoalkyl, cyanoalkoxy, alkinyloxy, alkinylalkoxy, heterocyclyl, heterocyclylalkyl, heterocyclylalkoxy, haloalkyl and haloalkoxy and, wherein two of $R^1$, $R^2$, $R^3$, $R^4$ and $R^5$ optionally form together —$(CH_2)_n$—O— and, with the proviso that at least one of $R^1$, $R^2$, $R^3$, $R^4$ and $R^5$ is not hydrogen and 2-(4-tert-butyl-benzyl)-morpholine is excluded.

Further preferred are compounds of formula I, wherein $R^1$, $R^2$, $R^3$, $R^4$ and $R^5$ are independently selected from hydrogen, alkyl, halogen, cyano, alkoxy, hydroxy, arylalkyl, arylalkoxy, alkenylalkoxy, cycloalkylalkoxy, hydroxyalkyl, alkoxyalkyl, hydroxyalkoxy, alkoxyalkoxy, alkenyl, alkenyloxy, N-hydroxy-amidinyl, aryloxyalkoxyalkyl, cyanoalkyl, cyanoalkoxy, alkinyloxy, alkinylalkoxy, heterocyclyl, heterocyclylalkyl, heterocyclylalkoxy, haloalkyl and haloalkoxy and, wherein two of $R^1$, $R^2$, $R^3$, $R^4$ and $R^5$ optionally form together —$(CH_2)_n$—O— and, with the proviso that at least one of $R^1$, $R^2$, $R^3$, $R^4$ and $R^5$ is not hydrogen and 2-(4-tert-butyl-benzyl)-morpholine is excluded.

Further preferred are those compounds of formula I, wherein one of $R^1$ and $R^5$ is hydrogen and the other one is alkyl, halogen, cyano, alkoxy, hydroxy, arylalkyl, arylalkoxy, alkenylalkoxy, cycloalkylalkoxy, hydroxyalkyl, alkoxyalkyl, hydroxyalkoxy, alkoxyalkoxy, alkenyl, N-hydroxy-amidinyl, aryloxyalkoxyalkyl, cyanoalkyl, cyanoalkoxy, alkinyloxy, heterocyclylalkyl, heterocyclylalkoxy, haloalkyl and haloalkoxy and, wherein two of $R^1$, $R^2$, $R^3$, $R^4$ and $R^5$ optionally form together —$(CH_2)_n$—O—.

Further preferred are compounds of formula I, wherein $R^1$ and $R^5$ are independently selected from hydrogen, halogen, hydroxyl, alkoxy and haloalkoxy. Particularly preferred are compounds of formula I, wherein $R^1$ and $R^5$ are independently selected from hydrogen, halogen, hydroxy and haloalkoxy. Further particularly preferred are those compounds of formula I, wherein $R^1$ and $R^5$ are independently selected from hydrogen, fluoro, hydroxy and difluoromethoxy.

Very preferred are those compounds according to formula I, wherein $R^1$ and $R^5$ are hydrogen.

Also preferred are those compounds of formula I, wherein $R^2$ and $R^4$ are independently selected from hydrogen, alkyl, halogen, hydroxyalkyl, alkoxyalkyl, alkenyl, N-hydroxy-amidinyl, aryloxyalkoxyalkyl, heterocyclyl, heterocyclylalkyl and haloalkyl and, wherein $R^3$ and $R^4$ optionally form together —$(CH_2)_n$—O—. The term heterocyclyl, alone or in combination, as used in the definition of $R^2$ and $R^4$ means preferably pyridinyl, chloro-pyridinyl or 3,5-dimethyl-isoxazolyl. Particularly preferred are those compounds of formula I, wherein the term heterocyclyl, alone or in combination, as used in the definition of $R^2$ and $R^4$ means pyridinyl or chloro-pyridinyl.

Particularly preferred are those compounds according to formula I, wherein $R^2$ and $R^4$ are independently selected from hydrogen, alkyl, halogen, hydroxyalkyl, alkoxyalkyl, vinyl, N-hydroxy-amidinyl, aryloxyalkoxyalkyl, chloro-pyridinyl, pyridinylalkyl and trifluoromethyl and, wherein $R^3$ and $R^4$ optionally form together —$(CH_2)_2$—O—.

Very preferred are compounds of formula I, wherein $R^2$ and $R^4$ are independently selected from hydrogen, alkyl, halogen and trifluoromethyl. Particularly preferred are those compounds according to formula I, wherein one of $R^2$ and $R^4$ is hydrogen and the other one is alkyl, halogen or trifluoromethyl.

Preferred are those compounds of formula I, wherein $R^3$ is hydrogen, halogen, alkoxy, arylalkoxy, alkenylalkoxy, cycloalkylalkoxy, alkoxyalkoxy, alkenyloxy, cyanoalkoxy, heterocyclylalkoxy, haloalkoxy or haloalkoxy substituted with hydroxyl or, wherein $R^3$ and $R^4$ optionally form together —$(CH_2)_n$—O—.

Further preferred are the compounds of formula I, wherein $R^3$ is hydrogen, halogen, alkoxy, arylalkoxy, alkenylalkoxy, cycloalkylalkoxy, alkoxyalkoxy, alkenyloxy, cyanoalkoxy, heterocyclylalkoxy or haloalkoxy or, wherein $R^3$ and $R^4$ optionally form together —$(CH_2)_n$—O—. The term heterocyclyl, alone or in combination, as used in the definition of $R^3$ means e.g. methyl-isoxazolyl, tetrahydrofuranyl, imidazolyl, pyridinyl, thiazolyl, furanyl, oxadiazolyl, methyloxazolyl, benzothiazolyl, dimethyl-isoxazolyl, methylthiazolyl and preferably methyl-isoxazolyl.

Further particularly preferred are compounds of formula I, wherein $R^3$ is haloalkoxy substituted with hydroxyl.

Particularly preferred are those compounds of formula I, wherein $R^3$ is hydrogen, alkoxy, cycloalkylalkoxy, methyl-isoxazolylalkoxy or trifluoromethoxy.

Very preferred are those compounds according to formula I, wherein $R^3$ is hydrogen, methoxy, ethoxy, cyclopropylmethoxy, methyl-isoxazolylmethoxy or trifluoromethoxy.

Preferred are the compounds of formula I, wherein n is 2 or 3. Particularly preferred are those compounds of formula I, wherein n is 2.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant).

The term "asymmetric carbon atom" (C*) means a carbon atom with four different substituents. According to the Cahn-Ingold-Prelog Convention the asymmetric carbon atom can be of the "R" or "S" configuration.

Preferred are chiral compounds of formula I.

Preferred are those compounds of formula I, wherein the compound is of formula

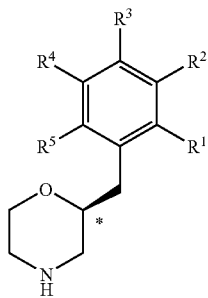

(Ib)

wherein the carbon atom C* is of the S configuration and $R^1$ to $R^5$ are defined as before.

Particularly preferred are those compounds according to formula I, wherein the compound is of formula

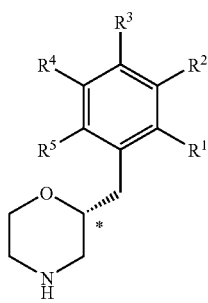

(Ia)

wherein the carbon atom C* is of the R configuration and $R^1$ to $R^5$ are defined as before.

Examples of preferred compounds of formula I are 1. 4-Bromo-2-(R)-1-morpholin-2-ylmethyl-phenol;
2. (R)-2-(4-Methoxy-3-trifluoromethyl-benzyl)-morpholine;
3. (R)-2-(2,5-Difluoro-4-methoxy-benzyl)-morpholine;
4. (R)-2-[3-Bromo-4-(5-methyl-isoxazol-3-ylmethoxy)-benzyl]-morpholine;
5. (R)-2-(2-Fluoro-4-methoxy-5-methyl-benzyl)-morpholine;
6. (R)-2-(4-Benzyloxy-3-bromo-benzyl)-morpholine;
7. (R)-2-{4-[((E)-But-2-enyl)oxy]-3-chloro-benzyl}-morpholine;
8. (R)-2-(4-Fluoro-3-trifluoromethyl-benzyl)-morpholine;
9. (R)-2-(3-Bromo-4-methoxy-benzyl)-morpholine;
10. (R)-2-(4-Ethoxy-3-trifluoromethyl-benzyl)-morpholine;
11. (R)-2-(4-Cyclopropylmethoxy-3-trifluoromethyl-benzyl)-morpholine;
12. (R)-2-(4-Methoxy-3-methyl-benzyl)-morpholine;
13. (R)-2-(2-Fluoro-5-trifluoromethyl-benzyl)-morpholine;
14. (R)-2-(3-Trifluoromethyl-benzyl)-morpholine;
15. (R)-2-(3-Bromo-benzyl)-morpholine;
16. (R)-2-(3-Chloro-benzyl)-morpholine;
17. (R)-2-[4-Methoxy-3-(1-methoxy-ethyl)-benzyl]-morpholine;
18. (R)-2-(3,4-Dichloro-benzyl)-morpholine;
19. (R)-2-(4-Allyloxy-3-bromo-benzyl)-morpholine;
20. (R)-2-[3-Chloro-4-(5-methyl-isoxazol-3-ylmethoxy)-benzyl]-morpholine;
21. (R)-2-(4-Allyloxy-3-chloro-benzyl)-morpholine;
22. (R)-2-(3-Bromo-4-ethoxy-benzyl)-morpholine;
23. (R)-2-(3-Bromo-4-cyclopropylmethoxy-benzyl)-morpholine;
24. (R)-2-(4-Methoxy-3-vinyl-benzyl)-morpholine;
25. N-Hydroxy-2-methoxy-5-(R)-1-morpholin-2-ylmethyl-benzamidine;
26. (R)-2-[3-(2-Phenoxy-ethoxymethyl)-benzyl]-morpholine;
27. (S)-2-(3-Chloro-4-cyclopropylmethoxy-benzyl)-morpholine;
28. (R)-2-(3-Chloro-4-ethoxy-benzyl)-morpholine;
29. 2-(R)-1-Morpholin-2-ylmethyl-phenol;
30. (R)-2-(4-Chloro-3-methyl-benzyl)-morpholine;
31. (R)-2-[3-(2-Pyridin-4-yl-ethyl)-benzyl]-morpholine;
32. (2-Bromo-4-(R)-(1-morpholin-2-ylmethyl)-phenoxy)-acetonitrile;
33. (R)-2-(3-Methyl-benzyl)-morpholine;
34. (R)-2-(2-Difluoromethoxy-benzyl)-morpholine;
35. (S)-2-(3-Bromo-4-methoxy-benzyl)-morpholine;
36. (R)-2-[3-Bromo-4-(2-methoxy-ethoxy)-benzyl]-morpholine;
37. (R)-2-[4-(2,2,2-Trifluoro-ethoxy)-3-trifluoromethyl-benzyl]-morpholine;
38. (R)-2-(3-Bromo-4-prop-2-ynyloxy-benzyl)-morpholine;
39. (R)-2-(3-Chloro-4-prop-2-ynyloxy-benzyl)-morpholine;
40. (R)-2-[3-Chloro-4-(2,2,2-trifluoro-ethoxy)-benzyl]-morpholine;
41. (R)-2-(3-Vinyl-benzyl)-morpholine;
42. (R)-2-(5-Chloro-2-fluoro-benzyl)-morpholine;
43. (R)-2-[3-Chloro-4-(2-methoxy-ethoxy)-benzyl]-morpholine;
44. (R)-2-[3-Chloro-4-(pyridin-3-ylmethoxy)-benzyl]-morpholine;
45. (R)-2-[3-(6-Chloro-pyridin-3-yl)-benzyl]-morpholine;
46. (R)-2-(3-Bromo-4-methoxy-5-methyl-benzyl)-morpholine;
47. (R)-2-(3-Fluoro-4-methoxy-benzyl)-morpholine;
48. (R)-2-[3-(2-Pyridin-3-yl-ethyl)-benzyl]-morpholine;
49. 1-(2-Methoxy-5-(R)-1-morpholin-2-ylmethyl-phenyl)-ethanol;
50. (R)-2-(7-Bromo-2,3-dihydro-benzofuran-5-ylmethyl)-morpholine;
51. 2,4-Dibromo-6-(R)-1-morpholin-2-ylmethyl-phenol;
52. (R)-2-[3-Chloro-4-(tetrahydro-furan-2-ylmethoxy)-benzyl]-morpholine;
53. (R)-2-(3-Ethyl-4-methoxy-benzyl)-morpholine;
54. (R)-2-[3-(3,5-dimethyl-isoxazol-4-yl)-4-methoxybenzyl]-morpholine;
55. 1-(2-Methoxy-5-(R)-1-morpholin-2-ylmethyl-phenyl)-ethanone;
56. (R)-2-(3-Iodo-4-methoxy-benzyl)-morpholine;
57. (R)-2-(5-Bromo-2,4-dimethoxy-benzyl)-morpholine;
58. (R)-2-(3-Chloro-4-propyloxy-benzyl)-morpholine;
59. (R)-2-(3-Bromo-4-cyclopentyloxy-benzyl)-morpholine;
60. (R)-2-(5-Bromo-2-difluoromethoxy-benzyl)-morpholine;
61. (R)-2-(3-Bromo-4-butoxy-benzyl)-morpholine;
62. (R)-2-(3-Bromo-4-isopropoxy-benzyl)-morpholine;
63. (R)-2-(3-Bromo-4-propoxy-benzyl)-morpholine;

64. (R)-2-(3-Chloro-4-methoxy-benzyl)-morpholine;
65. (R)-2-(5-Chloro-2-fluoro-4-methoxy-benzyl)-morpholine;
66. (R)-2-(2,2-Difluoro-benzo[1,3]dioxol-4-ylmethyl)-morpholine;
67. (R)-2-(2-Fluoro-3-trifluoromethyl-benzyl)-morpholine;
68. (R)-2-[3-(2-Pyridin-2-yl-ethyl)-benzyl]-morpholine;
69. 2-(3-Ethyl-benzyl)-morpholine;
70. 2-(2-Fluoro-3-methyl-benzyl)-morpholine;
71. 2-(4-Fluoro-3-methylbenzyl)-morpholine;
72. 2-(3-Bromo-4-methoxy-benzyl)-morpholine;
73. 2-(3-Bromobenzyl)-morpholine;
74. (S)-2-(3-Trifluoromethyl-benzyl)-morpholine;
75. 2-(2-Difluoromethoxy-benzyl)-morpholine;
76. 2-(3-Methyl-benzyl)-morpholine;
77. 2-(3-Trifluoromethyl-benzyl)-morpholine;
78. (R)-4-(2,5-Difluoro-4-(R)-(1-morpholin-2-ylmethyl)-phenoxy)-1,1,1-trifluoro-butan-2-ol;
79. (R)-2-[2,5-Difluoro-4-(5-methyl-isoxazol-3-ylmethoxy)-benzyl]-morpholine;
80. (R)-2-(2-Chloro-4'-methanesulfonyl-biphenyl-4-ylmethyl)-morpholine;
81. (R)-2-(3-Chloro-4-methylsulfanyl-benzyl)-morpholine;
82. (R)-2-(3-Cyclopropyl-4-methoxy-benzyl)-morpholine;
83. (R)-2-{3-Chloro-4-[5-(4-methoxy-phenyl)-[1,2,4]oxadiazol-3-ylmethoxy]-benzyl}-morpholine;
84. (R)-2-[3-Chloro-4-(2-phenyl-5-methyl-oxazol-4-ylmethoxy)-benzyl]-morpholine;
85. (R)-2-[3-Chloro-4-(5-phenyl-[1,2,4]oxadiazol-3-ylmethoxy)-benzyl]-morpholine;
86. (R)-2-{3-Chloro-4-[5-(4-trifluoromethyl-phenyl)-[1,2,4]oxadiazol-3-ylmethoxy]-benzyl}-morpholine;
87. (R)-2-{3-Chloro-4-[2-(4-chloro-phenyl)-thiazol-4-ylmethoxy]-benzyl}-morpholine;
88. (R)-2-[3-Chloro-4-(5-trifluoromethyl-furan-2-ylmethoxy)-benzyl]-morpholine;
89. (R)-2-[4-(1-Benzyl-1H-imidazol-2-ylmethoxy)-3-chloro-benzyl]-morpholine;
90. (R)-2-[3-Chloro-4-(pyridin-2-ylmethoxy)-benzyl]-morpholine;
91. 2-(2-Chloro-4-(R)-(1-morpholin-2-ylmethyl)-phenoxymethyl)-benzothiazole;
92. (R)-2-[3-Chloro-4-(3,5-dimethyl-isoxazol-4-ylmethoxy)-benzyl]-morpholine;
93. (R)-2-[3-Chloro-4-(2-methyl-thiazol-4-ylmethoxy)-benzyl]-morpholine;
94. (R)-2-(2-Chloro-3'-fluoro-4'-methyl-biphenyl-4-ylmethyl)-morpholine;
95. (R)-2-(3-Methoxymethyl-benzyl)-morpholine and
96. (R)-2-(3-Cyclopropylmethoxymethyl-benzyl)-morpholine.

Examples of particularly preferred compounds of formula I are
(R)-2-(4-Methoxy-3-trifluoromethyl-benzyl)-morpholine;
(R)-2-[3-Bromo-4-(5-methyl-isoxazol-3-ylmethoxy)-benzyl]-morpholine;
(R)-2-(4-Ethoxy-3-trifluoromethyl-benzyl)-morpholine;
(R)-2-(4-Cyclopropylmethoxy-3-trifluoromethyl-benzyl)-morpholine;
(R)-2-(4-Methoxy-3-methyl-benzyl)-morpholine;
(R)-2-(3-Trifluoromethyl-benzyl)-morpholine;
(R)-2-(3-Chloro-benzyl)-morpholine;
(R)-2-[3-Chloro-4-(5-methyl-isoxazol-3-ylmethoxy)-benzyl]-morpholine;
(R)-2-(3-Bromo-4-ethoxy-benzyl)-morpholine;
(R)-2-[3-Chloro-4-(2,2,2-trifluoro-ethoxy)-benzyl]-morpholine;
(R)-2-(3-Chloro-4-ethoxy-benzyl)-morpholine;
(2-Bromo-4-(R)-(1-morpholin-2-ylmethyl)-phenoxy)-acetonitrile;
(R)-4-(2,5-Difluoro-4-(R)-1-morpholin-2-ylmethyl-phenoxy)-1,1,1-trifluoro-butan-2-ol and
(R)-2-[3-Chloro-4-(2,2,2-trifluoro-ethoxy)-benzyl]-morpholine.

Processes for the manufacture of the compounds according to formula I are an embodiment of the present invention. The substituents and indices used in the following schemes have the significance given above unless indicated to the contrary.

The synthesis of 2-benzylmorpholine and its use as an appetite suppressant/anorexant are described in the Journal of Pharmacy and Pharmacology (1990), 42(11), 797-9). The synthetic route starts from 1-phenyl-2-propene/allylbenzene which is subjected to bromine and water to give 2-bromo-3-phenyl-1-propanol (A). Use of sodium hydroxide with the bromo-alcohol yields 2-benzyloxirane. This in turn is reacted with ethanolamine-O-sulfate under basic conditions, and then cyclized by the addition of further base (sodium hydroxide) and raised temperatures to form the target compound 2-benzylmorpholine (I; $R^1$-$R^5$=hydrogen) (Scheme 1). The appetite suppressing activity of this compound was reported to reside in the (+)-enantiomer, after the isomers had been separated by dibenzoyl tartaric acid salt resolution. No stereochemical configuration was assigned.

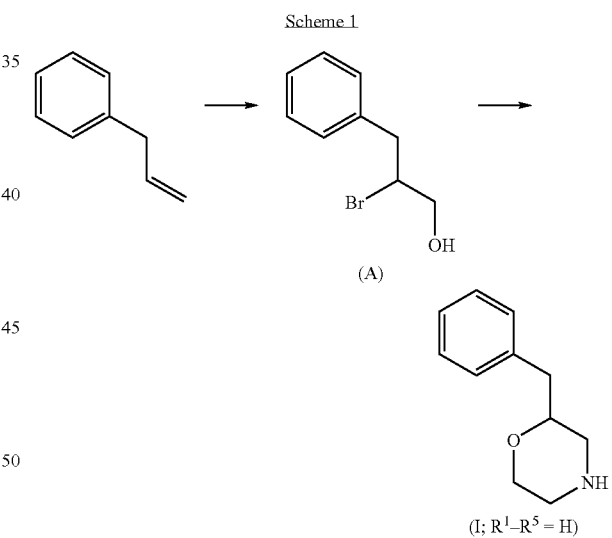

Scheme 1

The stereo-selective synthesis of this compound has been reported since (Tetrahedron: Asymmetry (1998), 9(22), 4021-4026). This route used Baker's yeast reduction of (Z)-alpha-bromocinnamaldehyde in the presence of absorbing resins to allow the preparation of the corresponding saturated (S)-bromohydrin (A') in high yields and enantiomeric excess. The absolute configuration is assigned through conversion into the (R)-Ph oxirane and (S)-PhCH2CH(OH)Me. The (R)-epoxide is transformed into (R)-benzylmorpholine (IA, $R^1$ to $R^5$=H), the pharmacologically active enantiomer of the appetite suppressant 2-benzylmorpholine, to which the (R) configuration is assigned (Scheme 2).

Scheme 2

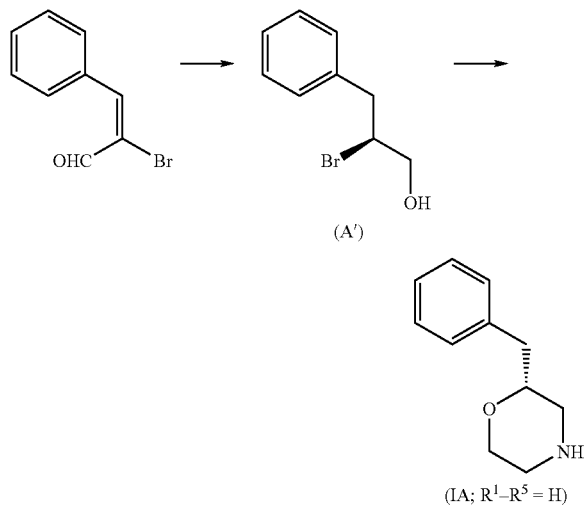

General synthetic routes for preparation of compounds of the present invention:

To facilitate synthesis of chiral materials of known stereochemistry aryl organometallic reagents were reacted with (R)-epichlorohydrin in the presence of either copper (I) salts (for example copper (I) bromide) or Lewis acids (for example boron trifluoride) to yield chlorohydrin intermediates (B). The organometallic species used included, for example, aryl lithium halides or aryl magnesium halides. The copper salts used included, for example copper (I) bromide or copper (I) iodide. The Lewis acids used included for example, boron trifluoride. Exposure of the chlorohydrin intermediates to a base and ethanolamine-O-sulfate, in a similar manner to that mentioned above yields the suitably substituted (R)-2-benzylmorpholine (Ia; Scheme 3). Typically the (S)-enantiomer can be made in an analogous manner from (S)-epichlorohydrin.

Scheme 3

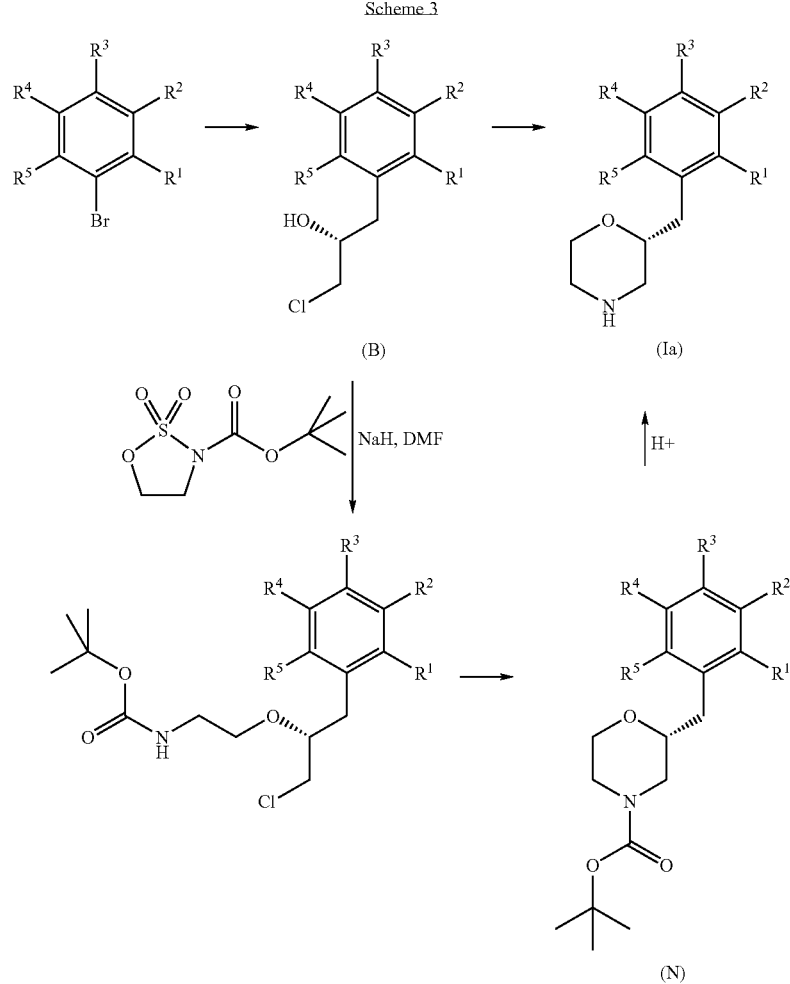

Further manipulation of the morpholines formed would be done by protection of the morpholine nitrogen and then functional transformation of the aromatic ring. Alternatively the e.g. Boc-protected morpholines (N) can be directly accessed via alkylation of the hydroxy group in the chloro-hydrins (B) using N-Boc-sulfamidates (prepared as described in WO2002072584) and a base such as, e.g. sodium hydride, in an appropriate solvent such as, e.g. N,N-dimethylformamide and subsequent ring closure under basic conditions (e.g. sodium hydride in N,N-dimethylformamide).

The synthetic schemes for the list of ten preferred compounds are given below.

3-Bromobenzotrifluoride (C) was reacted with magnesium turnings to give the 3-trilfuoromethylphenylmagnesium bromide, Grignard reagent. Addition of copper (I) bromide and slow addition of (R)-epichlorohydrin at 0° C. gives R-1-chloro-3-(3-trifluoromethylphenyl)-2-propanol (D). Reaction of the chloro-alcohol with sodium hydroxide as base, ethanolamine-O-sulfate under the conditions described in Journal of Pharmacy and Pharmacology ((1990), 42(11), 797-9) yields R-2-(3-trifluoromethyl)benzylmorpholine (Example 14; Scheme 4)

In a similar way (R)-2-(4-methoxy-3-methyl)benzylmorpholine (Example 12) can be made starting from 4-bromo-2-methyl-anisole.

Scheme 4

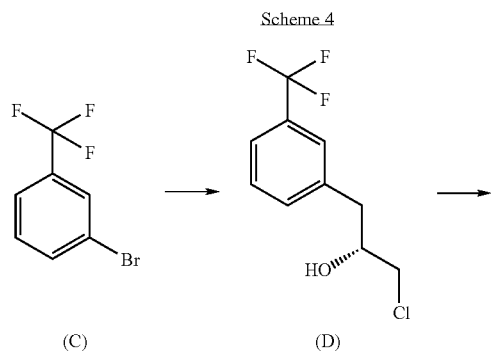

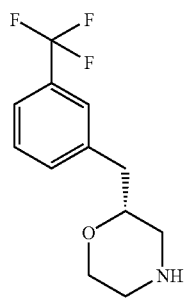

(Example 14)

2-Bromo-anisole was transformed into an aryl lithium reagent on reaction with n-butyllithium at −78° C. Boron trifluoride can then be added and subsequent slow addition of R-epichlorohydrin and slow warming to room temperature gives the desired R-1-chloro-3-(2-methoxy)phenyl-2-propanol (E). This can then be reacted with ethanolamine-O-sulfate, as mentioned above, to obtain the desired R-2-(2-methoxy)benzyl morpholine (Ia; $R^1$=methoxy, $R^2$=$R^3$=$R^4$=$R^5$=hydrogen). Dealkylation occurs with hydrobromic acid (to yield example 29) and the phenol derivative can be protected at the morpholine nitrogen, for example as the tertiary-butylcarbamate using e.g. di-tert-butyl dicarbonate. This then allows reaction with halogenating agents like N-bromo-succinimide, to obtain both N-tert-butoxycarbonyl-R-2-(5-bromo-2-hydroxy)benzylmorpholine and tert-butoxycarbonyl-R-2-(3,5-dibromo-2-hydroxy)benzyl morpholine. Removal of the protecting group under acidic conditions, e.g. using trifluoroacetic acid, gives the R-2-(5-bromo-2-hydroxy)benzyl morpholine (Example 1) and the dibromo-analogue (Example 51; Scheme 5). A similar route can be used to make R-2-(4-hydroxy)benzylmorpholine.

Scheme 5

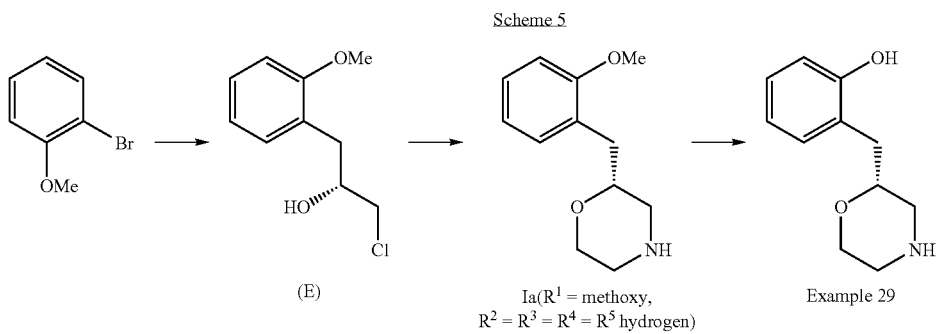

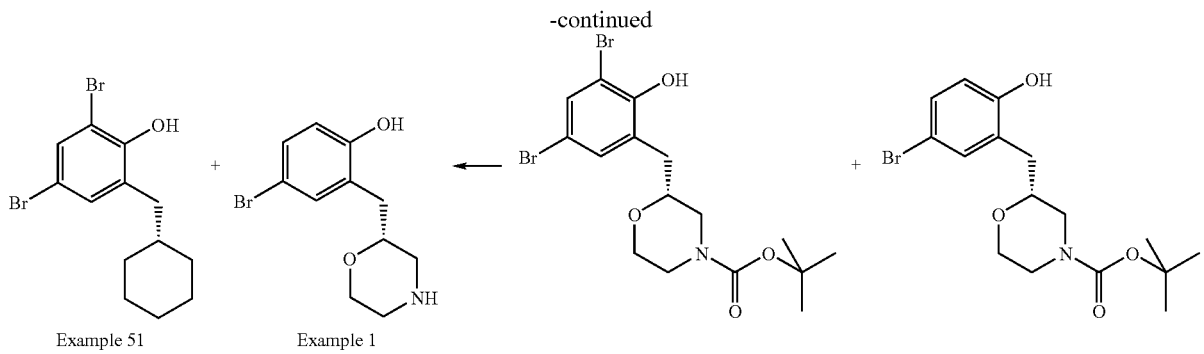

As an alternative route to R-2-(4-hydroxy)-benzylmorpholine, R-2-(4-benzyloxy)-benzylmorpholine can be made from 1-bromo-4-benzyloxybenzene and (R)-epichlorohydrin. R-2-(4-benzyloxy)-benzylmorpholine is protected as the tert-butylcarbamate and subjected to hydrogenation conditions to deprotect the phenol. R-2-(4-hydroxy)-benzylmorpholine is halogenated with either N-chloro or N-bromosuccinimide. 3-Halo-4-hydroxy-benzylmorpholines were then alkylated using sodium hydride as base and a range of alkyl halides and arylmethyl halides or heteroarylmethyl halides (Scheme 6).

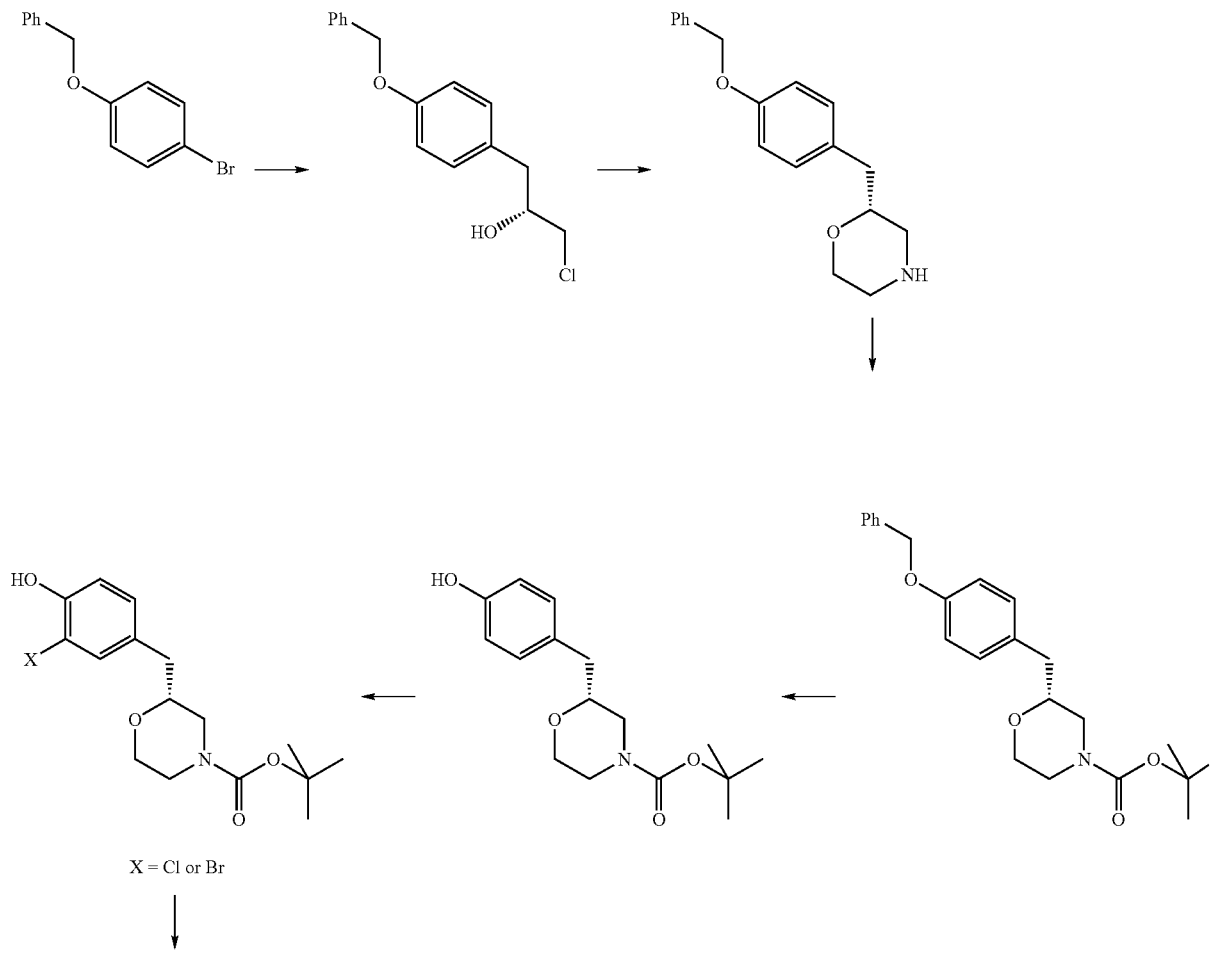

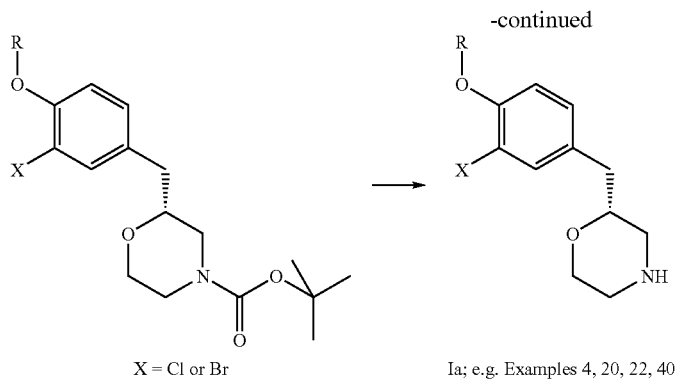

X = Cl or Br      Ia; e.g. Examples 4, 20, 22, 40

Alternatively the 4-alkoxy moiety can be incorporated via alkoxide displacement of aromatic fluorides that are ortho-positioned to a suitably activating group, for example trifluoromethyl. Starting from 4-bromo-2-fluorobenzotrifluoride and (R)-epichlorohydrin, R-2-(4-fluoro-3-trifluoromethyl)benzylmorpholine (Example 8) is obtained. This can be protected on the morpholine nitrogen as the tert-butylcarbamate and reacted with alcohols and bases (for example sodium hydride or cesium carbonate) under high temperature or microwave activated conditions to yield the desired 4-alkoxy-3-trifluoromethyl adducts as shown below. Subsequent deprotection yields the desired final products such as, e.g. examples 2, 10 or 11 (Scheme 7).

Another chemical route to compounds of the general formula I starts from 2-(methoxy-methyl-carbamoyl)-morpholine-4-carboxylic acid tert-butyl ester (G) which can be obtained from morpholine-2-carboxylic acid ethyl ester (F) (J. Med. Chem. 1993, 36, 683-689). For this purpose the morpholine nitrogen is protected as e.g. the tert-butylcarbamate. The ester is then cleaved to the acid by e.g. saponification and the acid is converted to the morpholin-2-(N-methyl-N-methoxy)carboxamide (G) through treatment with N,O-dimethylhydroxylamine hydrochloride after activation of the acid with, e.g. N,N'-carbonyldiimidazole. The amide (G) can be reacted with organometallic aryl reagents such as e.g. Grignard or lithium compounds which Scheme 7

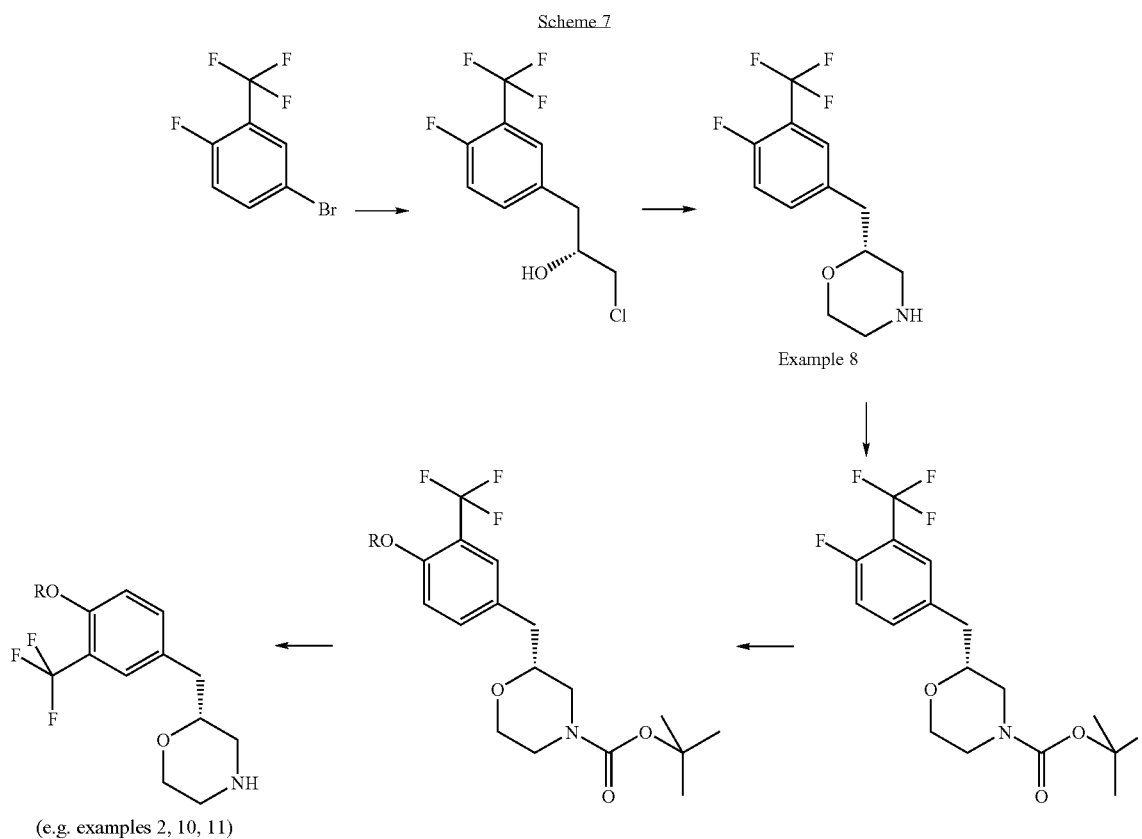

(e.g. examples 2, 10, 11)

can be prepared from the corresponding halogenated aryl compounds to furnish the 2-benzoyl substituted morpholines (H). The ketone is reduced to the alcohol, which is then further converted to the bromide (L). Reduction of the bromide and deprotection gives the desired compounds of general formula I.

Typically the enantiomers of compounds of the general formula I can be made in an analogous manner from (R) or (S)-2-(methoxy-methyl-carbamoyl)-morpholine-4-carboxylate which in turn can be obtained by e.g. separation of racemic (G) using chiral HPLC.

Scheme 8

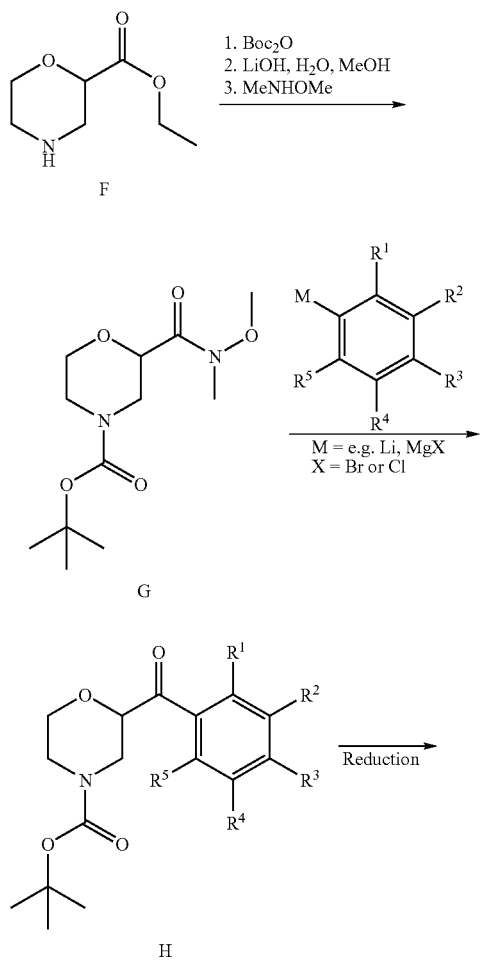

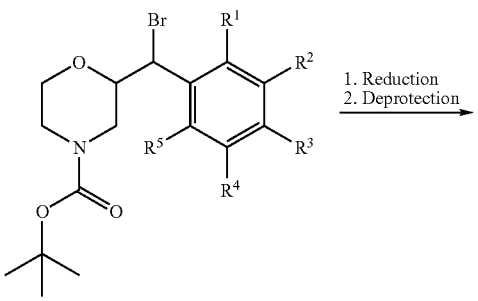

L

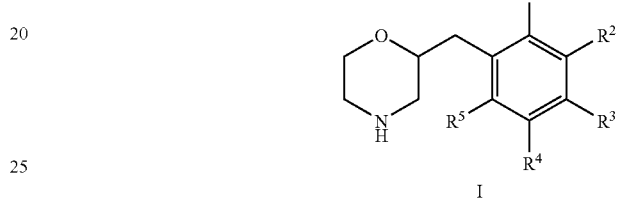

I

Alternatively, the morpholine-2-carboxylic acid ethyl ester (F) (J. Med. Chem. 1993, 36, 683-689) can be N-protected with e.g. a trityl protective group, reduced to the hydroxymethylmorpholine using, e.g. lithium aluminium hydride, and the free alcohol converted to the trifluoromethanesulfonic acid 4-trityl-morpholin-2-ylmethyl ester (M) using e.g. triflic anhydride and a base such as, e.g. pyridine. The intermediate (M) can be reacted with organometallic aryl reagents such as e.g. Grignard compounds under copper catalysis using e.g. copper (I) chloride, to furnish the 2-benzyl morpholines which after deprotection yield the compounds of the general formula I (scheme 9).

Typically the enantiomers of compounds of the general formula I can be made in an analogous manner from either (R) or (S)-trifluoro-methanesulfonic acid 4-trityl-morpholin-2-ylmethyl ester which in turn can be obtained by, e.g. chiral synthesis of hydroxymethylmorpholine in analogy to the method of Berg et. Al. (J. Med. Chem., 1998, 41, 1934-42) or separation of racemic hydroxymethylmorpholine or intermediate (M) using chiral HPLC.

Scheme 9

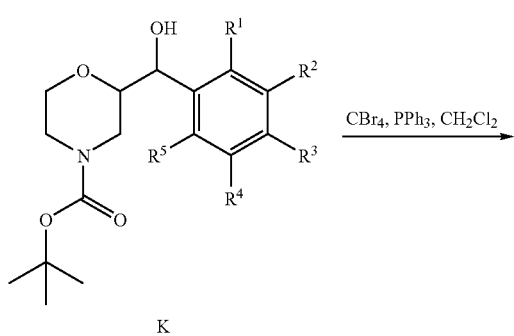

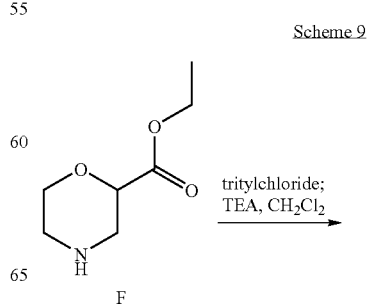

-continued

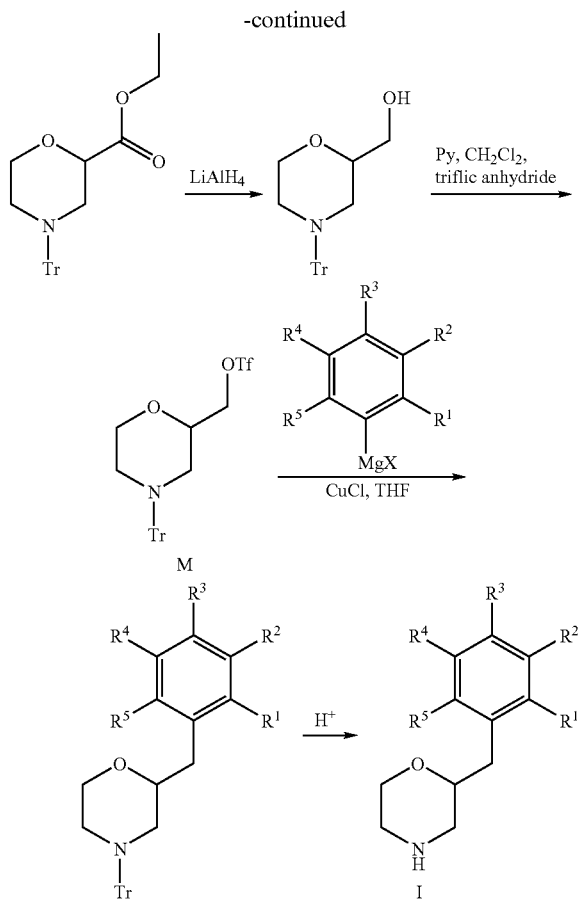

It is a further embodiment of the invention to provide compounds according to formula I for use as therapeutically active substances.

It is another embodiment of the invention to provide compounds of formula I as described above for the production of medicaments for the prophylaxis and therapy of illnesses which are caused by disorders associated with the 5-HT$_2$ receptors, the 5-HT$_{2A}$, 5-HT$_{2B}$ and 5-HT$_{2C}$ subtypes, particularly the 5-HT$_{2C}$ subtype.

Likewise it is an embodiment of the invention to provide pharmaceutical compositions comprising a compound of formula I and a therapeutically inert carrier.

It is a further embodiment of the invention to provide a compound in accordance with formula I for use in the production of medicaments for the treatment and prophylaxis of eating disorders and obesity.

Also preferred is the use of a compound in accordance with formula I for the production of medicaments for the treatment and prophylaxis of diabetes mellitus (DM) including Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), diabetes insipidus, hyperglycemia, diabetic complications and insulin resistance.

Particularly preferred is the use of a compound in accordance with formula I for the production of medicaments for the treatment of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), hyperglycemia, diabetic complications and insulin resistance.

It is a further particularly preferred embodiment of the invention to provide a compound in accordance with formula I for use in the production of medicaments for the treatment of Type II diabetes (non-insulin dependent diabetes mellitus (NIDDM)).

An embodiment of the invention is the use of compounds in accordance with formula I for the production of medicaments for the treatment and prophylaxis of disorders of the central nervous system, cardiovascular disorders, gastrointestinal disorders, diabetes insipidus and sleep apnoea.

Particularly an embodiment of the invention is the above use, wherein the disorders of the central nervous system are selected from depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioral disorders, behavioral disorders associated with dementia, organic mental disorders, mental disorders in childhood, aggression, age-related memory disorders, chronic fatigue syndrome, drug and alcohol addiction, bulimia, anorexia nervosa, premenstrual tension, trauma, stroke, neurodegenerative diseases, encephalitis, meningitis and urinary incontinence.

A further preferred embodiment of the present invention is the above mentioned use of the compounds according to formula I, wherein the cardiovascular disorder is thrombosis.

Also preferred is the aforementioned use of the compounds according to formula I, wherein the gastrointestinal disorder is dysfunction of gastrointestinal motility.

A further embodiment of the invention are compounds in accordance with formula I, when manufactured according to the processes described herein.

A further embodiment of the present invention is a method for the treatment and prophylaxis of disorders of the central nervous system, cardiovascular disorders, gastrointestinal disorders, diabetes insipidus and sleep apnoea, which method comprises administering an effective amount of a compound of formula I as described.

Preferred is this method, wherein the disorders of the central nervous system are selected from depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioral disorders, behavioral disorders associated with dementia, organic mental disorders, mental disorders in childhood, aggressivity, age-related memory disorders, chronic fatigue syndrome, drug and alcohol addiction, bulimia, anorexia nervosa, premenstrual tension, trauma, stroke, neurodegenerative diseases, encephalitis, meningitis and urinary incontinence.

A further embodiment of the present invention is the method for the treatment and prophylaxis of sexual dysfunction which method comprises administering an effective amount of a compound of formula I as described.

Preferred is a method for the treatment and prophylaxis of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, type III diabetes (malnutrition related diabetes), diabetes insipidus, hyperglycemia, diabetic complications and insulin resistance, which method comprises administering an effective amount of a compound in accordance with formula I.

Particularly preferred is a method for the treatment and prophylaxis of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, type III diabetes (malnutrition related diabetes), hyperglycemia, diabetic complications and insulin resistance, which method comprises administering an effective amount of a compound in accordance with formula I.

It is a preferred embodiment of the invention to provide a method for the treatment and prophylaxis of eating disorders and obesity, which method comprises administering an effective amount of a compound of formula I.

It is a preferred embodiment of the invention to provide a method for the treatment and prophylaxis of Type II diabetes (non-insulin dependent diabetes mellitus (NIDDM), which method comprises administering an effective amount of a compound of formula I.

It is a further preferred embodiment of the invention to provide a method of treatment of obesity in a human which comprises administration of a therapeutically effective amount of a compound according to formula I and a therapeutically effective amount of a lipase inhibitor, particularly, wherein the lipase inhibitor is orlistat. Also an embodiment of the invention is the method as described above for the simultaneous, separate or sequential administration.

It is a further preferred embodiment to provide a method of treatment of Type II diabetes (non-insulin dependent diabetes mellitus (NIDDM) in a human which comprises administration of a therapeutically effective amount of a compound according to formula I and a therapeutically effective amount of a lipase inhibitor, particularly, wherein the lipase inhibitor is orlistat. Also an embodiment of the invention is the method as described above for the simultaneous, separate or sequential administration of a compound according to formula I and a lipase inhibitor, particularly orlistat.

It is a further preferred embodiment of the invention to provide a method of treatment of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), diabetes insipidus, hyperglycemia, diabetic complications and insulin resistance in a human which comprises administration a therapeutically effective amount of a compound according to formula I and a therapeutically effective amount of a lipase inhibitor, particularly, wherein the lipase inhibitor is orlistat. It is also an embodiment of the invention to provide a method as described above for the simultaneous, separate or sequential administration of a compound according to formula I and a lipase inhibitor, particularly orlistat.

It is a further particularly preferred embodiment of the invention to provide a method of treatment of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), hyperglycemia, diabetic complications and insulin resistance in a human which comprises administration a therapeutically effective amount of a compound according to formula I and a therapeutically effective amount of a lipase inhibitor, particularly, wherein the lipase inhibitor is orlistat. It is also an embodiment of the invention to provide a method as described above for the simultaneous, separate or sequential administration of a compound according to formula I and a lipase inhibitor, particularly orlistat.

A further embodiment of the invention is the use of a compound of formula I in the manufacture of a medicament for the treatment and prevention of obesity in a patient who is also receiving treatment with a lipase inhibitor and particularly, wherein the lipase inhibitor is orlistat.

A further embodiment of the invention is the use of a compound of formula I in the manufacture of a medicament for the treatment and prevention of obesity in a patient who is also receiving treatment with a compound selected from the following list: Nerve growth factor agonist (e.g. axokine), growth hormone agonist (e.g. AOD-9604), adrenergic uptake inhibitor (e.g. GW-320659), 5-HT reuptake inhibitor (e.g. Prozac), 5-HT/NA reuptake inhibitor (e.g. sibutramine), DA reuptake inhibitor (e.g. Buproprion), 5-HT, NA and DA reuptake blocker, steroidal plant extract (eg P57), NPY1 or 5 antagonist, MC4 agonist, CCKA agonist, MCH antagonist (e.g. SNAP 7941), H3 receptor antagonist, H1 agonist, CRF agonist, Galanin antagonist, uncoupling protein, orexin antagonist, GLP-1 agonist, IL-6 agonist, α-MSH agonist, AGRP antagonist, 5-HT$_{1B}$ agonist, POMC antagonist, NN2211, Exendin-4 agonists and CB-1 inverse agonist or antagonist.

A further embodiment of the invention is the use of a compound of formula I in the manufacture of a medicament for the treatment and prevention of Type II diabetes (non-insulin dependent diabetes mellitus (NIDDM)) in a patient who is also receiving treatment with a lipase inhibitor and particularly, wherein the lipase inhibitor is orlistat.

A further preferred embodiment of the present invention is the use of a compound according to formula I in the manufacture of a medicament for the treatment and prevention of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), diabetes insipidus, hyperglycemia, diabetic complications and insulin resistance in a patient who is also receiving treatment with a lipase inhibitor particularly, wherein the lipase inhibitor is orlistat.

A further particularly preferred embodiment of the present invention is the use of a compound according to formula I in the manufacture of a medicament for the treatment and prevention of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), hyperglycemia, diabetic complications and insulin resistance in a patient who is also receiving treatment with a lipase inhibitor particularly, wherein the lipase inhibitor is orlistat.

A further embodiment of the present invention is the use of a compound according to formula I in the manufacture of a medicament for the treatment of sexual dysfunction.

It is also an embodiment of the invention to provide a pharmaceutical composition comprising a compound of formula I, a therapeutically inert carrier and a therapeutically effective amount of a lipase inhibitor, particularly, wherein the lipase inhibitor is orlistat.

Other combinations which may be considered are Sibutramine comprising combinations or combination with CB-1 inverse agonist/antagonist.

It is also a preferred embodiment of the invention to provide a method of treatment and/or prevention in mammals disorders where a reduction of the blood glucose concentration is beneficial comprising administering a therapeutically effective amount of a compound of formula I. Particularly preferred is this use or method wherein the disorders are disorders involving elevated plasma blood glucose.

The compounds of formula (I) may be used in the treatment (including prophylactic treatment) of disorders associated with 5-$HT_2$ receptor function. The compounds may act as receptor agonists or antagonists. Preferably, the compounds may be used in the treatment (including prophylactic treatment) of disorders associated with 5-$HT_{2B}$ and/or 5-$HT_{2C}$ receptor function. Preferably, the compounds may be used in the treatment (including prophylactic treatment) of disorders where a 5-$HT_{2C}$ receptor agonist is required.

A further preferred embodiment of the present invention is a process for the preparation of a compound of formula I comprising one of the following reactions:

reaction of a compound according to formula (B2) in the presence of a base such as e.g. sodium hydroxide in water and ethanolamine-O-sulfate in order to obtain a compound according to formula (I)

reaction of a compound (M3) in the presence of a compound (M2) particularly in the presence of a copper salt such as e.g. copper (I) chloride, particularly in tetrahydrofuran, in order to form a compound (M4) which is transformed into a compound of the formula I by cleaving of the protecting group PG, preferably the trityl protecting group PG means a protecting group;
Tf means the triflic group.

Another preferred aspect of this invention are the following intermediates:

(R)-2-(3-Bromo-benzyl)-morpholine-4-carboxylic acid tert-butyl ester (R)-2-(3-Chloro-4-trifluoromethanesulfonyloxy-benzyl)-morpholine-4-carboxylic acid tert-butyl ester (R)-2-(3-Bromo-4-hydroxy-benzyl)-morpholine-4-carboxylic acid tert-butyl ester (R)-2-(3-Chloro-4-hydroxy-benzyl)-morpholine-4-carboxylic acid tert-butyl ester (R)-2-(2,5-Difluoro-4-hydroxy-benzyl)-morpholine-4-carboxylic acid tert-butyl ester (S)-2-(Methoxy-methyl-carbamoyl)-morpholine-4-carboxylic acid tert-butyl ester (R)-2-(Methoxy-methyl-carbamoyl)-morpholine-4-carboxylic acid tert-butyl ester Trifluoro-methanesulfonic acid 4-trityl-morpholin-2-ylmethyl ester (R)-2-(4-Fluoro-3-trifluoromethylbenzyl)-morpholine-4-carboxylic acid tert-butyl ester (R)-2-(4-Methoxy-benzyl)-morpholine-4-carboxylic acid tert-butyl ester (R)-2-(4-Hydroxy-benzyl)-morpholine-4-carboxylic acid tert-butyl ester (R)-2-(4-Methoxy-3-iodobenzyl)-morpholine-4-carboxylic acid tert-butyl ester (R)-2-(3-Vinyl-benzyl)-morpholine-4-carboxylic acid tert-butyl ester N-benzyl-(R)-2-(3-chloro-4-fluoro-benzyl)-morpholine The processes as described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from basic compounds.

The compositions of the present invention may be formulated in a conventional manner using one or more pharmaceutically acceptable carriers. Thus, the active compounds of the invention may be formulated for oral, buccal, intranasal, parenteral (e.g. intravenous, intramuscular or subcutaneous) transdermal or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropylmethylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulating agents such as suspending, stabilizing and/or dispersing agents.

Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g. containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g. obesity) is 0.1 to 500 mg of the active ingredient per unit dose which could be administered, for example, 1 to 4 times per day.

Assay Procedures

Binding to Serotonin Receptors

The binding of compounds of formula (I) to serotonin receptors was determined in vitro by standard methods. The preparations were investigated in accordance with the assays given hereinafter.

Method (a): For the binding to the $5\text{-HT}_{2C}$ receptor the $5\text{-HT}_{2C}$ receptors were radiolabeled with $[^3\text{H}]$-5-HT. The affinity of the compounds for $5\text{-HT}_{2C}$ receptors in a CHO cell line was determined according to the procedure of D. Hoyer, G. Engel and H. O. Kalkman, *European J. Pharmacol.*, 1985, 118, 13-23.

Method (b): For the binding to the $5\text{-HT}_{2B}$ receptor the $5\text{-HT}_{2B}$ receptors were radiolabeled with $[^3\text{H}]$-5-HT. The affinity of the compounds for human $5\text{-HT}_{2B}$ receptors in a CHO cell line was determined according to the procedure of K. Schmuck, C. Ullmer, P. Engels and H. Lubbert, *FEBS Lett.*, 1994, 342, 85-90.

Method (c): For the binding to the $5\text{-HT}_{2A}$ receptor the $5\text{-HT}_{2A}$ receptors were radiolabeled with $[^{125}\text{I}]$-DOI. The affinity of the compounds for $5\text{-HT}_{2A}$ receptors in a CHO cell line was determined according to the procedure of D. J. McKenna and S. J. Peroutka, *J. Neurosci.*, 1989, 9, 3482-90.

The thus determined activity of the compound of the Example is shown in Table 1.

TABLE 1

| Compound | Method (a) $K_i$ (2C) | Method (b) $K_i$ (2B) | Method (c) $K_i$ (2A) |
|---|---|---|---|
| (structure) | 169 nM | >10000 nM | >10000 nM |
| Example 14 | 10 nM | 55 nM | 89 nM |
| Example 46 | 82 nM | >10000 nM | 641 nM |

Preferred compounds of formula I as described above have Ki (2C) values below 10000 nM; especially preferred compounds have Ki (2C) values below 1000 nM, particularly preferred compounds have Ki (2C) values below 100 nM. Most preferred compounds have Ki (2C) values below 30 nM.

Functional Activity

The functional activity of compounds of formula (I) was assayed using a Fluorimetric Imaging Plate Reader (FLIPR). CHO cells expressing the human $5\text{-HT}_{2C}$ or human $5\text{-HT}_{2A}$ receptors were counted and plated into standard 96 well microtitre plates on the day before testing to give a confluent monolayer. The cells were then loaded with the calcium sensitive dye, Fluo-3-AM. Unincorporated dye was removed using an automated cell washer to leave a total volume of 100 μL/well of assay buffer (Hanks balanced salt solution containing 20 mM Hepes and 2.5 mM probenecid). The drug (dissolved in 50 μL of the assay buffer) was added at a rate of 70 μL/sec to each well of the FLIPR 96 well plate during fluorescence measurements. The measurements were taken at 1 sec intervals and the maximum fluorescent signal was measured (approx 10-15 secs after drug addition) and compared with the response produced by 10 μM 5-HT (defined as 100%) to which it was expressed as a percentage response (relative efficacy). Dose response curves were constructed using Graphpad Prism (Graph Software Inc.).

TABLE 2

| Compound | h5-HT2C | | h5-HT2A | |
| --- | --- | --- | --- | --- |
| | EC$_{50}$ [nM] | Rel. Eff. [%] | EC$_{50}$ [nM] | Rel. Eff.[%] |
| 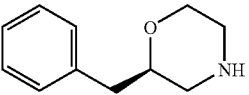 | >3000 | 41 | >3000 | 2 |
| Example 14 | 7 | 97 | 511 | 47 |
| Example 46 | 53 | 94 | >3000 | 21 |

The compounds of formula (I) have activity at the human 5-HT$_{2C}$ receptor in the range of 10,000 to 0.01 nM.

Preferred compounds of formula I as described above have activity at the human 5-HT$_{2C}$ receptor below 10000 nM; especially preferred compounds below 1000 nM, particularly preferred compounds below 100 nM. Most preferred compounds have activity at the human 5-HT$_{2C}$ receptor below 30 nM.

Regulation of Feeding Behavior

The in vivo activity of compounds of formula (1) was assessed for their ability to regulate feeding behavior by recording food consumption in food deprived animals.

Rats were trained to have access to food for 2 h per day and were food deprived for 22 h. When they were trained under this schedule, the amount of food taken every day during these 2 h food intake session was consistent day after day.

To test the ability of the 5-HT$_{2C}$ receptor agonists to decrease food intake, 8 animals were used in a cross-over study. Rats were individually housed in plexiglass boxes with a grid on the floor and a paper was placed below the cage floor to collect any spillage. A food dispenser (becher) filled with a preweighed amount of food was presented to them for 2 h. At the end of the food intake session, rats returned to their home cage. Each rat was weighed before the start of the experiment and the amount of food consumed during this 2 h food intake session was recorded. Either various doses of test compound or Vehicle was administered orally 60 min before the 2 h food intake session. Sibutramine was included in the experiment as a positive control.

An Anova analysis with repeated measures was used followed by a posthoc test Student Neumann-Keuls. * P<0.05 compared to Saline-treated rats.

The minimum effective dose (m.e.d.) is defined as the lowest dose which produces a statistically significant reduction in food intake. The minimum effective doses for selected particularly preferred compounds of formula I are 30 mg/kg p.o. and below.

The invention will now be described in detail with reference to the following examples. It will be appreciated that the invention is described by way of example only and modification of detail may be made without departing from the scope of the invention.

EXAMPLES

Example 1

(R)-2-(5-Bromo-2-hydroxybenzyl)morpholine

Deprotection of N-Boc-(R)-2-(5-bromo-2-hydroxybenzyl)morpholine, using hydrogen chloride (4M, in methanol), afforded the morpholine example 1 as an off-white solid (51 mg, 100%).

LC (50% to 80% gradient 220 nm XTERRA 2 ml/min) 100% @ 0.94 min.

Mass spec: found [M–H]$^-$ 270/272.

Intermediates

N-Boc-(R)-2-(5-Bromo-2-hydroxybenzyl)morpholine and

N-Boc-(R)-2-(3,5-Dibromo-2-hydroxybenzyl)morpholine

N-Bromosuccinimide (67 mg, 0.375 mmol) was added to a solution of intermediate (c), N-Boc-(R)-2-(2-hydroxybenzyl)morpholine, (100 mg, 0.341 mmol) in dimethylformamide (5 mL) at ambient temperature and the mixture stirred for 23 hr. The mixture was partitioned between ethyl acetate and water and the organic phase separated and further washed with water (x3), dried (Na$_2$SO$_4$) and concentrated to give the crude product which was purified by chromatography (silica: 10% ethyl acetate/iso-hexane) to give the N-BOC protected monobromide intermediate (a), N-Boc-(R)-2-(5-Bromo-2-hydroxybenzyl)morpholine, as a white solid (70 mg, 55% yield).

LC (50% to 80% gradient 220 nm XTERRA 2 ml/min) 96% @ 5.29 min.

Mass spec: found [M–H]$^+$ 370/372.

and N-BOC protected dibromide intermediate (b), N-Boc-(R)-2-(5-Bromo-2-hydroxybenzyl)morpholine, as a white solid (72 mg, 45% yield).

LC (50% to 80% gradient 220 nm XTERRA 2 ml/min) 94% @ 6.55 min.

Mass spec: found [M–H]$^+$ 448/450/452.

N-BOC-(R)-2-(2-hydroxybenzyl)morpholine

To a cooled (ice bath) solution of, (R)-2-(2-methoxybenzyl)morpholine, intermediate (d) (285 mg, 1.38 mmol) in dichloromethane (10 mL) was added boron tribromide (1.0M dichloromethane, 3.04 mL, 3.04 mmol). The reaction mixture was stirred to ambient temperature over 19 hrs before being re-cooled in an ice bath and stirred with aq. potassium carbonate (419 mg, 3.04 mmol) for 30 mins. After warming, the organic phase was separated and concentrated. The residue was taken up in dioxane and added to a solution of di-tertbutyl dicarbonate (331 mg, 1.52 mmol) in water (10 mL) and stirred for 1 hr. Extraction with ethyl acetate, separation and drying afforded a brown oil which was purified by chromatography (silica: 10% ethyl acetate/iso-hexane) to afford the phenolic intermediate (c), N-BOC-(R)-2-(2-hydroxybenzyl)morpholine, as a white solid (116 mg, 29% yield).

LC (20% to 50% gradient 210 nm XTERRA 2 ml/min) 99.1% @ 8.72 min.

Mass spec: found [M–H]$^-$ 292.

(R)-2-(2-methoxybenzyl)morpholine

Powdered sodium hydroxide (7.2 g, 180 mmol) was dissolved in water (15 mL). The solution was allowed to cool to ambient temperature before addition of intermediate (a) (R)-1-chloro-3-(2-methoxyphenyl)-2-propanol(6.0 g, 30.0 mmol) in methanol (20 mL+2×5 mL washes) via dropping funnel. After stirring for 5 mins 2-aminoethane hydrogen sulfate (16.9 g, 120 mmol) was added in portions over 5 mins and the reaction mixture heated to 40° C. After 2 hrs, toluene (75 mL) and powdered sodium hydroxide (7.2 g, 180 mmol) were added and the reaction heated to 65° C. and stirred for 17 hrs. The mixture was cooled, diluted with water (300 mL) and extracted with toluene (2×150 mL). The combined organics were washed with water (slowly separating emulsion obtained) and brine, dried ($Na_2SO_4$) and concentrated under reduced pressure to afford the crude product as a pale yellow oil (5.21 g). Purification by column chromatography (silica: ethyl acetate/ethanol/triethylamine, 79/20/1 ratio) afforded intermediate (d), (R)-2-(2-methoxybenzyl)morpholine as a colorless oil (6.04 g, 50% yield).

LC (20% to 50% gradient 210 nm XTERRA 2 ml/min) 89% @ 1.62 min.

Mass spec: found $[MH]^+$ 208.

(R)-1-chloro-3-(2-methoxyphenyl)-2-propanol

To a solution of 2-bromoanisole (11.21 g, 59.93 mmol) in dry tetrahydrofuran (Aldrich sure-seal, 160 mL) at −70° C. was added n-butyllithium (1.05 eq. of 2.5M in hexanes, freshly opened, 25.2 mL, 62.93 mmol). After 30 mins stirring at −70° C., $BF_3$ etherate (9.36 g, 65.9 mmol) was added. After a further 30 mins at −70° C. (R)-epichlorohydrin (5.55 g, 59.93 mmol) in tetrahydrofuran (50 mL) was added. After 2 hrs the reaction mixture was quenched by the addition of 10% aqueous ammonium chloride (50 mL) followed by warming to ambient temperature. ethyl acetate was added and the organic phase washed with water and brine. Drying ($Na_2SO_4$) and concentration under reduced pressure afforded the crude product as a pale yellow semi-solid (9.88 g). Purification by silica gel chromatography (5% ethyl acetate/iso-hexane) afforded the intermediate (e), (R)-1-chloro-3-(2-methoxyphenyl)-2-propanol, as colorless oil (6.04 g, 50% yield).

δH (400 MHz, $CDCl_3$) 7.24 (1H, t, J 7.9 Hz), 7.18 (1H, d, J 7.7 Hz), 6.94 (1H, t, J 6.7 Hz), 6.88 (1H, d, J 8.1 Hz), 4.14-4.07 (1H, m), 3.84 (3H, s), 3.57 (1H, dd, J 11.0, 4.5 Hz), 3.50 (1H, dd, J 11.0 Hz, 6.5 Hz), 2.93 (2H, d, J 6.6 Hz), 2.61 (1H, d, J 4.4 Hz).

LC (20% to 50% gradient 210 nm XTERRA 2 ml/min) 93% @ 1.41 min.

Example 2

(R)-2-(4-methoxy-3-trifluoromethylbenzyl)morpholine

Intermediate (a), N-Boc-(R)-2-(4-methoxy-3-trifluoromethylbenzyl)morpholine (23 mg, 0.06 mmol), was deprotected using trifluoroacetic acid, (20% v/v solution in dichloromethane, 1 mL total) over 2.5 hrs. The reaction mixture was poured onto an SCX-2 column (2 g) and washed with dichloromethane (2 mL×2) and dichloromethane: methanol (1:1 v/v, 2 mL×2). The column was then washed with ammonia (2N solution in methanol, 2 mL×3) and the ammonia washes were concentrated in vacuo to yield the desired morpholine, example 2 as a white solid (15 mg, 89%).

LC (50% to 80% gradient 210 nm XTERRA 2 ml/min) 99.4% @ 1.12 min.

Mass spec: $[MH]^+$ 276.

Intermediates

N-Boc-(R)-2-(4-methoxy-3-trifluoromethylbenzyl)morpholine

Intermediate (b), N-Boc-(R)-2-(4-fluoro-3-trifluoromethylbenzyl)morpholine, (67 mg, 0.18 mmol) was dissolved in methanol (1.5 mL) with cesium carbonate (0.240 g, 0.74 mmol) and subjected to microwave heating at 135° C. for 30 mins and then microwave heating at 130° C. for 20 mins.

The material was partitioned between water (4 mL) and dichloromethane (4 mL), shaken and separated through a PTFE separator. The dichloromethane solution was then dried (MgSO4), filtered and concentrated in vacuo. The residue was purified by column chromatography (silica, 20% ethylacetate/isohexane) to yield the desired intermediate (a), N-Boc-(R)-2-(4-methoxy-3-trifluoromethylbenzyl)morpholine, as a colorless oil (26 mg).

N-Boc-(R)-2-(4-fluoro-3-trifluoromethylbenzyl)morpholine

Intermediate (c) (R)-2-(4-fluoro-3-trifluoromethylbenzyl)morpholine (2.14 g, 8.13 mmol) was dissolved in dichloromethane (30 mL) and cooled to 0° C. then ditertiarybutyldicarbonate (1.95 g, 8.95 mmol) added over 5 minutes. The reaction was stirred at room temperature for 72 hrs, concentrated in vacuo and the residue purified by column chromatography (silica; 20% to 30% ethyl acetate/isohexane) to yield the desired intermediate (b) as a colorless oil (1.17 g).

LC (50% to 80% gradient 220 nm XTERRA 2 ml/min) 97.8% @ 5.80 min.

Mass spec: $[MH]^+$ 364; $[M-tertBuOCO+H]^+$ 264

(R)-2-(4-fluoro-3-trifluoromethylbenzyl)morpholine

Powdered sodium hydroxide (3.36 g, 84 mmol) was dissolved in water (5.6 mL) and cooled to room temperature. Intermediate (d) (R)-1-chloro-3-(4-fluoro-3-trifluoromethylphenyl)-2-propanol (assumed 13 mmol) was added as a solution in methanol (13.3 mL in total) and the mixture stirred for 5 minutes at room temperature. 2-aminoethane hydrogen sulfate (7.90 g, 56 mmol) was added in one portion and the resultant mixture warmed to 40° C. (bath temperature) for 2 hrs. Toluene (35 mL) and sodium hydroxide (powdered 3.36 g, 84 mmol) were added and the reaction heated at 65° C. (bath temperature) for 18 hrs, with vigorous stirring. The reaction was allowed to cool to room temperature and poured into water (80 mL), layers separated and the aqueous layer extracted with ethyl acetate (40 mL×2). Combined organic layers were washed with brine (30 mL), dried (MgSO4), filtered and concentrated in vacuo. The residue was purified by column chromatography (silica; triethylamine/ethanol ethanol/ethyl acetate, 1/20/79 ratio) yielded the desired intermediate (c), (R)-2-(4-fluoro-3-trifluoromethylbenzyl)morpholine, as yellow oil (2.34 g).

LC (50% to 80% gradient 220 nm XTERRA 2 ml/min) 87.3% @ 1.43 min.

Mass spec: $[MH]^+$ 264

(R)-1-chloro-3-(4-fluoro-3-trifluoromethylphenyl)-2-propanol

5-Bromo-2-fluoro-benzotrifluoride (3.16 g, 13 mmol) was added over 5-10 minutes as a solution in diethyl ether (14 mL in total) dropwise to magnesium turnings (0.316 g, 13 mmol) in diethyl ether (1 mL), under an atmosphere of nitrogen. The reaction was maintained at a gentle reflux by control of addition rate during addition of the bromide and then allowed to cool to room temperature and stirred for a further 1 hr. Copper (I) iodide (206 mg, 1.08 mmol) was added in one portion and the reaction mixture cooled to 0° C. over 10 minutes. (R)-epichlorohydrin (1.0 g, 10.8 mmol)

was added as a solution in diethyl ether (14 mL in total) over 10 minutes and the reaction allowed to warm to room temperature and stirred for 2 hrs. Ammonium chloride (saturated aqueous solution, 10 mL) and the mixture poured into water (40 mL) and extracted with ethyl acetate (30 mL×2). The combined organic layers were washed with brine (20 mL), dried (MgSO$_4$), filtered and concentrated in vacuo. Column chromatography (silica; 5% ethyl acetate/isohexane) yielded the desired intermediate (d), (R)-1-chloro-3-(4-fluoro-3-trifluoromethylphenyl)-2-propanol, as a pale yellow oil (3.75 g).

δH (400 MHz, CDCl$_3$) 7.50-7.47 (1H, br d, J 6.9 Hz), 7.45-7.42 (1H, m), 7.15 (1H, dd, J 10.0, 8.6 Hz), 4.08-4.01 (1H, m), 3.62 (1H, dd, J 11.4, 3.8 Hz), 3.50 (1H, dd, J 11.3, 6.3 Hz), 2.90 (2H, ddd, J 20.6, 14.1, 6.6 Hz), 2.19 (1H, d, J 5.0 Hz).

LC (50% to 80% gradient 220 nm XTERRA 2 ml/min) 94.1% @ 3.28 min.

Example 3

(R)-2-(2,5-difluoro-4-methoxybenzyl)morpholine

Example 3 was prepared as described for example 1, intermediate (d), but using (R)-1-chloro-3-(2,5-difluoro-4-methoxyphenyl)-2-propanol, intermediate (a), to obtain the desired morpholine, example 3 as a pale yellow oil, (0.528 g).

LC (20% to 50% gradient 210 nm XTERRA 2 ml/min) 97.4% @ 4.10 min.

Mass spec: [MH]+244.

Intermediates (R)-1-chloro-3-(2,5-difluoro-4-methoxyphenyl)-2-propanol (R)-1-chloro-3-(2,5-difluoro-4-methoxyphenyl)-2-propanol, was prepared, using the same procedure as described for example 2, intermediate (d), but from 4-bromo-3,5-difluoroanisole and (R)-epichlorohydrin, to yield the desired intermediate (a).

Example 4

(R)-2-(3-bromo-4-(2-methylisoxazol-4-yl)methoxybenzyl)morpholine

Intermediate (a) (66 mg, 0.18 mmol) was dissolved in acetone (1.5 mL) and treated with potassium carbonate (49 mg, 0.36 mmol) and 4-bromomethyl-2-methyl-isoxazole (70 mg, 0.53 mmol) was added and the resulting reaction was shaken at 55° C. for 16 hrs. The reaction was filtered and concentrated under a flow of nitrogen. The crude residue was dissolved in tetrahydrofuran:ethanol (1:1, 4 mL) and polymer supported thiophenol (0.43 g, 0.64 mmol), MP-carbonate (0.24 g, 0.64 mmol) and diisopropylethylamine (119 uL, 0.68 mmol) added. The reaction was shaken for 24 hrs, then filtered and concentrated under a high flow of nitrogen. The crude residue was dissolved in (20% v/v solution in dichloromethane, 2.5 mL) and shaken for 3 hrs at room temperature. The reaction mixture was added directly to an SCX-2 column (2 g) and washed with dichloromethane (2 mL×2) and methanol (2 mL×2). The SCX-2 column was then washed with ammonia (2N in methanol, 3×2 mL). Combined ammonia washes were concentrated in vacuo. The residue was purified by preparative HPLC to yield the desired morpholine example 4 as a colorless oil (30 mg).

LC (50% to 80% gradient 210 nm XTERRA 2 ml/min) 99.1% @ 1.20 min.

Mass spec: found [MH]+ 367/369.

Intermediates

N-BOC-(R)-2-(3-bromo-4-hydroxybenzyl)morpholine

To a stirred solution of intermediate (b), N-BOC-(R)-2-(4-hydroxybenzyl)morpholine (1.0 g, 3.41 mmol) in anhydrous N,N-dimethyl formamide (10 mL), under at atmosphere of nitrogen at room temperature was added N-bromosuccinimide (0.63 g, 3.58 mmol). The resulting solution was stirred at room temperature for 2 hrs and then poured into water (50 mL) and extracted with ethyl acetate (70 mL×2). Combined organic layers were washed with water (2×50 mL), brine (50 mL), dried (MgSO$_4$), filtered and concentrated in vacuo. The material was concentrated onto sodium sulfate and purified by column chromatography (silica; 17% ethyl acetate/isohexane) to yield the desired intermediate (a), N-BOC-(R)-2-(3-bromo-4-hydroxybenzyl) morpholine, as a white solid (0.89 g).

N-BOC-(R)-2-(4-hydroxybenzyl)morpholine

To a solution of the intermediate (c), N-Boc-(R)-2-(4-benzyloxybenzyl)morpholine (4.92 g, 12.8 mmol) in ethanol (100 mL), was added 10% palladium on charcoal (1.3 g, 1.28 mmol) and the flask flushed with hydrogen. The mixture was stirred at 38° C. for 16 h then filtered through celite and concentrated to afford the product intermediate (b), N-BOC-(R)-2-(4-hydroxybenzyl)morpholine, as a brown oil (3.7 g, 99%).

LC (50% to 80% gradient 210 nm XTERRA 2 ml/min) 95.4% @ 1.95 min.

Mass spec: [M–H]⁻ found 292.

N-Boc-(R)-2-(4-benzyloxybenzyl)morpholine

To a cooled solution of the intermediate (d), (R)-2-(4-benzyloxybenzyl)morpholine (4.97 g, 17.6 mmol) in dichloromethane (150 mL), was added di-tertiary-butyldicarbonate (4.4 mL, 19.3 mmol). The mixture was stirred at ambient temperature for 16 h, the solvent was evaporated and the residual oil crystallized on trituration with iso-hexane. The product, intermediate (c), N-Boc-(R)-2-(4-benzyloxybenzyl)morpholine, was isolated by filtration as a pale yellow solid (4.92 g, 73%).

LC (50% to 80% gradient 210 nm XTERRA 2 ml/min) 99.3% @ 6.64 min.

Mass spec: found [MH]+ 384.

(R)-2-(4-benzyloxybenzyl)morpholine (R)-2-(4-benzyloxybenzyl)morpholine was prepared using the same method as described for example 1, intermediate (d), using (R)-1-chloro-3-(4-benzyloxyphenyl)-2-propanol, intermediate (e) (29.1 g, 105 mmol). Following chromatography (silica gel:ethyl acetate/ethanol/triethylamine, 79/20/1 ratio) the intermediate (d), (R)-2-(4-benzyloxybenzyl)morpholine, was isolated as a pale yellow oil (4.48 g, 15% yield).

LC (50% to 80% gradient 210 nm XTERRA 2 ml/min) 98.8% @ 1.78 min.

Mass spec: found [MH]+ 284.

(R)-1-chloro-3-(4-benzyloxyphenyl)-2-propanol (R)-1-chloro-3-(4-benzyloxyphenyl)-2-propanol, was made using the same procedure as described for example 2, intermediate (d) using (R)-epichlorohydrin and benzyl 4-bromophenylether (20.0 g, 76.0 mmol). Following chromatography (silica: 10% ethyl acetate/iso-hexane) the intermediate (e), (R)-1-chloro-3-(4-benzyloxyphenyl)-2-propanol, was isolated as a brown solid (9.59 g, 44% yield).

LC (50% to 80% gradient 210 nm XTERRA 2 ml/min) 95.1% @ 4.62 min.
Mass spec: found [M+H$_2$O]$^+$ 294.

Example 5

(R)-2-(2-fluoro-4-methoxy-5-methyl-benzylmorpholine (R)-1-chloro-3-(2-fluoro-4-methoxy-5-methylphenyl)-2-propanol was prepared using the same procedure as described for example 2, intermediate (d), using 4-bromo-3-fluoro-6-methylanisole and (R)-epichlorohydrin. The resultant (R)-1-chloro-3-(2-fluoro-4-methoxy-5-methylphenyl)-2-propanol was used in the same procedure as described for example 1, intermediate (d) to obtain the desired morpholine, example 5 as a yellow oil (0.91 g, 41% yield).
LC (20% to 50% gradient 210 nm XTERRA 2 ml/min) 97.6% @ 0.80 min.
Mass spec: [MH]+253.

Example 6

(R)-2-(3-bromo-4-benzyloxybenzyl)morpholine

Intermediate (a) N-Boc-(R)-2-(3-bromo-4-benzyloxybenzyl)morpholine was deprotected using the procedure described for example 1 to obtain the desired example 6, as an orange oil (0.18 g, 38% over 2 steps).
LC (50% to 80% gradient 210 nm XTERRA 2 ml/min) 96.1% @ 3.41 min.
Mass spec: found [MH]$^+$ 362/364.

Intermediates

N-Boc-(R)-2-(3-bromo-4-benzyloxybenzyl)morpholine
N-Boc-(R)-2-(3-bromo-4-benzyloxybenzyl)morpholine was prepared using the same method as described for example 1, intermediate (d), using example 4, intermediate (c) (0.563 g, 1.47 mmol) and N-bromosuccinimide (0.29 g, 1.62 mol).

Example 7

(R)-2-(3-chloro-4-(but-2-en-1-yloxy)benzyl)morpholine

Intermediate (a) (53 mg, 0.16 mmol), was dissolved in dichloromethane (4 mL) with crotyl alcohol (1:1 cis/trans, 23 mg, 0.32 mmol) shaken at room temperature for 20 mins and diisopropylazodicarboxylate (65 mg, 0.32 mmol) added in one portion. dichloromethane (6 mL) was added to solvate the polymer. The reaction mixture was shaken for 24 hrs, then filtered. Polymer supported tosyl chloride (0.18 g, 2.82 mmol/g) and MP-carbonate (0.39 g, 2.62 mmol/g) were added to the liquor and the mixture shaken for 6 hrs. The reaction was filtered and evaporated under a high flow of nitrogen. The crude residue was dissolved in TFA (20% v/v solution in dichloromethane, 2.0 mL) and shaken for 3 hrs at room temperature. The reaction mixture was added directly to an SCX-2 column (2 g) and washed with dichloromethane (2 mL×2) and methanol (2 mL×2). The SCX-2 column was then washed with ammonia (2N in methanol, 3×2 mL). Combined ammonia washes were concentrated in vacuo and the residue purified by preparative HPLC to yield the desired morpholine example 7 as a colorless oil (12 mg).

LC (50% to 80% gradient 210 nm XTERRA 2 ml/min) 98% @ 1.89 min.
Mass spec: found [MH]$^+$ 282.

Intermediates

N-BOC-(R)-2-(3-chloro-4-hydroxybenzyl)morpholine
To a stirred solution of example 4, intermediate (b), (0.669 g, 2.28 mmol) in N,N-dimethyl formamide (3 mL) was added N-chlorosuccinimide (0.304 g, 2.28 mmol). The resulting solution was stirred at room temperature for 20 hrs and then concentrated in vacuo. The residue was dissolved in ethyl acetate (25 mL) and washed with water (2×25 mL), brine (25 mL), dried (MgSO$_4$), filtered and concentrated in vacuo. The residue was purified by column chromatography (silica gel:eluant: 15% ethyl acetate/iso-hexane), to afford the intermediate 17 as a pale yellow oil (0.52 g, 100% yield).
LC (50% to 80% gradient 210 nm XTERRA 2 ml/min) 83% @ 3.7 min.
Mass spec: found [MH]$^+$ 304 [M–tBu+H]$^+$249.

Example 8

(R)-2-(4-Fluoro-3-trifluoromethylbenzyl)morpholine (R)-1-chloro-3-(4-fluoro-3-trifluoromethylphenyl)-2-propanol was prepared using the same method as described for example 2, intermediate (d), but using 5-bromo-2-fluorobenzotrifluoride and (R)-epichlorohydrin. Example 8 was prepared as described for example 1, intermediate (d), but using (R)-1-chloro-3-(4-fluoro-3-trifluoromethylphenyl)-2-propanol to obtain the desired morpholine, example 8 as a colorless oil (0.7 g, 19%).
LC (50% to 80% gradient 210 nm XTERRA 2 ml/min) 87.3% @ 1.43 min.
Mass spec: [MH]$^+$ 264.

Example 9

(R)-2-(3-bromo-4-methoxybenzyl)morpholine

To a solution of intermediate (a) (0.26 g, 0.85 mmol) in dimethylformamide (10 m) was added N-bromosuccinimide (0.166, 0.93 mmol). The reaction mixture was stirred over 16 h at ambient temperature then partitioned between ethyl acetate and water. The organic phase was separated and further washed with water (×3), dried (Na$_2$SO$_4$) and concentrated to give the crude product as brown oil. The residue (0.238 g) was used directly in the next reaction.
The crude material was dissolved in trifluoroacetic acid (20% v/v in dichloromethane, 8 mL) over 2 hrs at room temperature. The reaction mixture was added directly to an SCX-2 column (5 g) and washed with dichloromethane (3 mL×2) and methanol (3 mL×2). The SCX-2 column was then washed with ammonia (2N in methanol, 3×2 mL). Combined ammonia washes were concentrated in vacuo and the residue purified by column chromatography (silica; triethylamine/ethanol/ethyl acetate; 1/20/79 ratio) twice to yield the desired morpholine example 9 as a colorless oil (29 mg).
LC (50% to 80% gradient 210 nm XTERRA 2 ml/min) 100% @ 0.88 min.
Mass spec: [MH]$^+$ 286/288.

Intermediates

N-Boc-(R)-2-(4-methoxybenzyl)morpholine
To a cooled solution of (R)-2-(4-Methoxybenzyl)morpholine intermediate (b) (0.262 g, 1.26 mmol) in dichloromethane (3 mL), cooled to 0° C. and was added di-tertiary-butyldicarbonate (0.32 mL, 1.39 mmol). The mixture was stirred at ambient temperature for 16 h, the solvent was evaporated and the residual oil purified by column chromatography (silica; 12% ethyl acetate/isohexane) to yield intermediate (a), N-Boc-(R)-2-(4-methoxybenzyl)morpholine, as a pale yellow oil (0.279 g, 0.91 mmol).

(R)-2-(4-Methoxybenzyl)morpholine (R)-1-chloro-3-(4-methoxyphenyl)-2-propanol was prepared using the same procedure as described for example 2, intermediate (d), using 4-bromoanisole and (R)-epichlorohydrin. Intermediate (b), (R)-2-(4-methoxybenzyl)morpholine was then prepared using the procedure as described for example 1, intermediate (d), from (R)-1-chloro-3-(4-methoxyphenyl)-2-propanol. Following purification by column chromatography (silica:ethyl acetate/ethanol ethanol/triethylamine, 79/20/1 ratio) this yielded (R)-2-(4-methoxybenzyl)morpholine, intermediate (b) as a pale yellow oil (0.288 g, 14% yield over 2 steps).

Example 10

(R)-2-(4-Ethoxy-3-trifluoromethylbenzyl)morpholine

N-Boc-(R)-2-(4-ethoxy-3-trifluoromethylbenzyl)morpholine, intermediate (a), was dissolved in TFA, (20% v/v solution in dichloromethane, 1.2 mL total) over 3 hrs. The reaction mixture was poured onto an SCX-2 column (2 g) and washed with dichloromethane (2 mL×2) and methanol (2 mL×2). The column was then washed with ammonia (2N solution in methanol, 2 mL×3) and the ammonia washes were concentrated in vacuo to yield the desired morpholine, example 10 as a yellow oil (17 mg, 85%).

LC (50% to 80% gradient 210 nm XTERRA 2 ml/min) 99.7% @ 1.59 min.

Mass spec: [MH]$^+$ 290.

Intermediates

N-Boc-(R)-2-(4-Ethoxy-3-trifluoromethylbenzyl)morpholine

Example 2, intermediate (b) (0.101 g, 0.28 mmol), was dissolved in ethanol (1.5 mL) with cesium carbonate (360 mg, 1.11 mmol) and subjected to microwave heating at 145° C. for 40 mins. The mixture was then subjected to microwave heating at 145° C. for 10 mins. The material was partitioned between water (4 mL) and dichloromethane (4 mL), shaken and separated through. The dichloromethane solution was then dried (MgSO$_4$), filtered and concentrated in vacuo. The residue was purified by column chromatography (silica, 15% to 20% ethylacetate/isohexane) to yield the desired intermediate (a), N-Boc-(R)-2-(4-Ethoxy-3-trifluoromethylbenzyl)morpholine, as a colorless oil (30 mg) that started to crystallize on standing.

LC (50% to 80% gradient 210 nm XTERRA 2 ml/min) 99.9% @ 6.14 min.

Mass spec: [MH]+390.

Example 11

(R)-2-(4-cyclopropylmethoxy-3-trifluoromethylbenzyl)morpholine

To a suspension of sodium hydride (40 mg, 0.96 mmol) in N,N-dimethyl formamide (3 mL) at 0° C. was added cyclopropylmethanol (69 mg, 0.96 mmol), and the resultant mixture stirred for 5 mins. Example 2, intermediate (b) (87 mg, 0.24 mmol) was added in one portion and the reaction mixture warmed to room temperature. The reaction was stirred for 24 hrs and then warmed to 45° C. for 24 hrs. The reaction was cooled to room temperature and poured into water (10 ml). The suspension was extracted with ethyl acetate (5 mL×2). Combined organic extracts were washed with water (5 mL×2) and brine (5 mL), dried (MgSO$_4$), filtered and concentrated in vacuo. The residue was purified by column chromatography (silica; 15% ethyl acetate/isohexane) to yield the desired product as a colorless oil (35 mg) and used directly in the next reaction. The residue was deprotected using TFA, dichloromethane (1:4, 1.3 mL) over 6 hrs, poured onto an SCX-2 column (2 g) and washed with dichloromethane (2 mL×2) and methanol (2 mL×2). The column was then washed with ammonia (2N solution in methanol, 2 mL×3) and the ammonia washes were concentrated in vacuo to yield a gum (16 mg). This material was purified by preparative HPLC to yield the desired morpholine the desired morpholine, example 11 (4 mg).

LC (50% to 80% gradient 210 nm XTERRA 2 ml/min) 98.3% @ 2.01 min.

Mass spec: [MH]$^+$ 316.

Example 12

(R)-2-(4-methoxy-3-methyl-benzyl)morpholine (R)-1-chloro-3-(4-methoxy-3-methylphenyl)-2-propanol was prepared using the same procedure as described for example 2, intermediate (d), using 4-bromo-2-methylanisole and (R)-epichlorhydrin. Example 12 was made using the same procedure as described for example 1, intermediate (d), using (R)-1-chloro-3-(4-methoxy-3-methylphenyl)-2-propanol. Following purification by column chromatography (silica: ethyl acetate/ethanol/triethylamine, 79/20/1 ratio) this gave morpholine example 12 as a pale yellow oil (0.134 g, 14% yield).

LC (20% to 50% gradient 210 nm XTERRA 2 ml/min) 97% @ 2.75 min.

Mass spec: found [MH]$^+$ 222.

Example 13

(R)-2-(2-fluoro-5-trifluoromethylbenzyl)morpholine (R)-1-chloro-3-(2-fluoro-5-trifluoromethylphenyl)-2-propanol, was prepared using the same method as described for example 2, intermediate (d), but using 3-bromo-4-fluorobenzotrifluoride, magnesium turnings, copper (I) iodide and (R)-epichlorohydrin.

Example 13 was prepared as described for example 1, intermediate (d), but using (R)-1-chloro-3-(2-fluoro-5-trifluoromethylphenyl)-2-propanol, to obtain the desired morpholine, example 13 as a colorless liquid (155 mg, 16%).

LC (50% to 80% gradient 220 nm XTERRA 2 ml/min) 83.4% @ 1.31 min.

Mass spec: [MH]+264.

Example 14

(R)-2-(3-trifluoromethyl)benzylmorpholine (R)-1-chloro-3-(3-trifluoromethylphenyl)-2-propanol was prepared using the same procedure as described for example 2, intermediate (d), but using 3-bromobenzotrifluoride and (R)-epichlorohydrin.

Example 14 was prepared using the same procedure as described for example 1, intermediate (d), using (R)-1-chloro-3-(3-trifluoromethylphenyl)-2-propanol. The residue was purified by column chromatography (silica: 1% triethylamine/20% methanol/ethyl acetate ) to yield the desired morpholine example 14 (0.21 g, 0.86 mmol, 23% over 2 steps).

LC (20% to 50% gradient 210 nm XTERRA 2 ml/min) 99.1% @ 5.39 min

Mass Spec: found [MH]$^+$ 246.

Example 15

(R)-2-(3-Bromobenzyl)morpholine 1-chloro-3-(3-bromophenyl)-2-propanol was prepared, using the same procedure as described for example 2, intermediate (d), but from 1,3-dibromobenzene and (R)-epichlorohydrin. Example 15 was prepared as described for example 1, intermediate (d), but using 1-chloro-3-(3-bromophenyl)-2-propanol, to obtain the desired morpholine, example 15 as a pale yellow oil (0.528 g, 12% yield).

LC (20% to 50% gradient 210 nm XTERRA 2 ml/min) 97.4% @ 4.10 min.

Mass spec: [MH]+256/258.

Example 16

(R)-2-(3-Chlorobenzyl)morpholine 1-chloro-3-(3-chlorophenyl)-2-propanol was prepared, using the same procedure as described for example 2, intermediate (d), but from 3-bromo-chlorobenzene and (R)-epichlorohydrin. Example 16 was prepared as described for example 1, intermediate (d), but using 1-chloro-3-(3-chlorophenyl)-2-propanol, to obtain the desired morpholine, example 16 as a colorless oil (35 mg).

LC (20% to 50% gradient 210 nm XTERRA 2 ml/min) 97.1% @ 3.48 min.

Mass spec: [MH]+212.

Example 17

(R)-2-(3-(1-Methoxyethyl)-4-methoxybenzyl)morpholine

Sodium borohydride (22 mg, 0.59 mmol) was added to a solution of intermediate (a), N-Boc-(R)-2-(3-acetyl-4-methoxybenzyl)morpholine (103 mg, 0.30 mmol) in ethanol (10 mL). The mixture was stirred for 17 h, concentrated and the residue partitioned between ethyl acetate and water. The organic phase was separated, dried (Na$_2$SO$_4$) and concentrated affording the crude product as a colorless oil. N-Boc deprotection of using hydrogen chloride (4 M in dioxane, 0.75 mL, 3.0 mmol) in methanol (10 mL) followed by purification using an SCX-2 cartridge eluting with methanol-ammonia afforded example 17 as a colorless oil (67 mg, 84%).

LC (50% to 80% gradient 220 nm XTERRA 2 ml/min) 95.1% @ 0.67 min.

Mass spec: [MH]+266.

Intermediates

N-Boc-(R)-2-(3-acetyl-4-methoxybenzyl)morpholine

Tetrakis(triphenylphosphine)palladium(0) (61 mg, 0.053 mmol) was added to a solution of intermediate (b), N-Boc-(R)-2-(3-Iodo-4-methoxybenzyl)morpholine (229 mg, 0.529 mmol), potassium carbonate (146 mg, 1.058 mmol), tetraethylammonium chloride (88 mg, 0.529 mmol) and tributyl (1-ethoxyvinyl)tin (0.179 mL, 0.529 mmol) in N,N-dimethyl formamide and heated to 90° C. for 18 h. The cooled reaction mixture was filtered and the liquors partitioned between ethyl acetate and water. The organic phase was separated and dried (Na$_2$SO$_4$) and concentrated to give the crude product which was purified by silica gel chromatography (silica: 10% ethyl acetate:dichloromethane) affording the crude material (a), N-Boc-(R)-2-(3-acetyl-4-methoxybenzyl)morpholine as a brown oil (248 mg) that was used without further purification.

N-Boc-(R)-2-(3-Iodo-4-methoxybenzyl)morpholine

Iodine (1.04 g, 4.1 mmol) was added to a solution of example 9, intermediate (a) (1.05 g, 3.42 mmol) and silver nitrite (0.79 g, 5.13 mmol) in methanol (30 mL) at ambient temperature and the mixture shaken for 19 hr. The mixture was partitioned between ethyl acetate and water and the organic phase separated and further washed with water (×3), dried (Na$_2$SO$_4$) and concentrated to give intermediate (b), N-Boc-(R)-2-(3-Iodo-4-methoxybenzyl)morpholine (1.44 g, 97%). The residue was used directly in subsequent reactions.

Example 18

(R)-2-(3,4-dichlorobenzyl)morpholine (R)-1-chloro-3-(3,4-dichlorophenyl)-2-propanol, was prepared, using the same procedure as described for example 2, intermediate (d), but from 3,4-dichlorobromobenzene and (R)-epichlorohydrin.

Example 18 was prepared as described for example 1, intermediate (d), but using (R)-1-chloro-3-(3,4-dichlorophenyl)-2-propanol, to obtain the desired morpholine, example 18 as a pale yellow oil (602 mg, 24%).

LC (50% to 80% gradient 220 nm XTERRA 2 ml/min) 93.7% @ 1.44 min.

Mass spec: [MH]+246.

Example 19

(R)-2-(3-bromo-4-(prop-2-en-1-yloxy)benzyl)morpholine

N-BOC-(R)-2-(3-bromo-4-hydroxybenzyl)morpholine, example 4, intermediate (a) (70 mg, 0.19 mmol) was dissolved in acetone (1.5 mL), treated with potassium carbonate (78 mg, 0.56 mmol) and allyl bromide (68 mg, 1.86 mmol) added. The resulting reaction was shaken at 55° C. for 16 hrs. The reaction was filtered and concentrated under a flow of nitrogen. The crude residue was dissolved in tetrahydrofuran (8 mL) with polymer supported diphenylphosphine (0.5 g) and shaken for 4 hrs. The reaction was then filtered and concentrated under a high flow of nitrogen. The crude residue was dissolved in TFA (20% v/v solution in dichloromethane, 2.5 mL) and shaken for 3 hrs at room temperature. The reaction mixture was added directly to an SCX-2 column (2 g) and washed with dichloromethane (2 mL×2) and methanol (2 mL×2). The SCX-2 column was then washed with ammonia (2N in methanol, 3×2 mL). Combined ammonia washes were concentrated in vacuo to yield the desired morpholine example 19 as a colorless oil (35 mg).

LC (50% to 80% gradient 210 nm XTERRA 2 ml/min) 99.4% @ 0.86 min.

Mass spec: found [MH]$^+$ 312/314.

Example 20

(R)-2-(3-chloro-4-(2-methylisoxazol-4-ylmethoxy) benzyl)morpholine

N-BOC-(R)-2-(3-chloro-4-hydroxybenzyl)morpholine, example 7, intermediate (a) (52 mg, 0.16 mmol), was dissolved in acetone (1.5 mL) with potassium carbonate (44 mg, 0.32 mmol) and 4-bromomethyl-2-methylisoxazole (55 uL, 0.47 mmol) added in one portion. The reaction was then heated to 55° C. and shaken at that temperature for 16 hrs. The reaction mixture was filtered, washing with acetone (1 mL×2) and the liquor evaporated under a high flow of nitrogen. The residue was dissolved in tetrahydrofuran: ethanol (1:1, 4 mL) and polymer supported thiophenol (0.43 g, 0.64 mmol), MP-carbonate (0.24 g, 0.64 mmol) and diisopropylethylamine (119 uL, 0.68 mmol) added. The reaction was shaken for 24 hrs, then filtered and concentrated under a high flow of nitrogen. The crude residue was dissolved in TFA (20% v/v solution in dichloromethane, 2.0 mL) and shaken for 3 hrs at room temperature. The reaction mixture was added directly to an SCX-2 column (2 g) and washed with dichloromethane (2 mL×2) and methanol (2 mL×2). The SCX-2 column was then washed with ammonia (2N in methanol, 3×2 mL). Combined ammonia washes were concentrated in vacuo to yield the desired morpholine example 20 as a colorless oil (19 mg).

LC (50% to 80% gradient 210 nm XTERRA 2 ml/min) 99.8% @ 1.03 min.

Mass spec: found [MH]$^+$ 324.

Example 21

(R)-2-(3-chloro-4-(prop-2-en-1-yloxy)benzyl)morpholine

N-BOC-(R)-2-(3-chloro-4-hydroxybenzyl)morpholine, example 7, intermediate (a) (52 mg, 0.16 mmol), was dissolved in acetone (1.5 mL) with potassium carbonate (44 mg, 0.32 mmol) and allyl bromide (33 uL, 0.38 mmol) added in one portion. The reaction was then heated to 55° C. and shaken at that temperature for 16 hrs. The reaction mixture was filtered, washing with acetone (1 mL×2) and the liquor evaporated under a high flow of nitrogen. The residue was dissolved in tetrahydrofuran: ethanol (1:1, 4 mL) and polymer supported thiophenol (0.43 g, 0.64 mmol), MP-carbonate (0.24 g, 0.64 mmol) and diisopropylethylamine (119 uL, 0.68 mmol) added. The reaction was shaken for 24 hrs, then filtered and concentrated under a high flow of nitrogen. The crude residue was dissolved in TFA (20% v/v solution in dichloromethane, 2.0 mL) and shaken for 3 hrs at room temperature. The reaction mixture was added directly to an SCX-2 column (2 g) and washed with dichloromethane (2 mL×2) and methanol (2 mL×2). The SCX-2 column was then washed with ammonia (2N in methanol, 3×2 mL). Combined ammonia washes were concentrated in vacuo to yield the desired morpholine example 21 as a colorless oil (15 mg).

LC (50% to 80% gradient 210 nm XTERRA 2 ml/min) 99.6% @ 1.27 min.

Mass spec: found [MH]$^+$ 268.

Example 22

(R)-2-(3-Bromo-4-ethoxybenzyl)morpholine

To a solution of intermediate (a), N-BOC-(R)-2-(4-ethoxybenzy)morpholine (0.205 g, 0.639 mmol) in dimethylformamide (15 mL) was added N-bromosuccinimide (0.125 g, 0.703 mmol). The reaction mixture was stirred over 16 h at ambient temperature then partitioned between ethyl acetate and water. The organic phase was separated and further washed with water (×3), dried (Na$_2$SO$_4$) and concentrated to give the crude product as a brown oil. Deprotection (20% trifluoroacetic acid in dichloromethane) afforded the morpholine example 22 as a yellow oil (91 mg, 80%).

LC (50% to 80% gradient 210 nm XTERRA 2 ml/min) 96.7% @ 1.25 min.

Mass spec: [MH]$^+$ 300/302.

Intermediates

N-BOC-(R)-2-(4-ethoxybenzyl)morpholine

To a solution of example 4, intermediate (b) (0.3 g, 1.02 mmol) in acetone (5 mL) was added potassium carbonate (0.283 g, 2.05 mmol) and iodoethane (0.164 mL, 2.05 mmol). The mixture was stirred at ambient temperature for 16 h. The reaction was then heated to 60° C. for a further 16 h then partitioned between ether and water. The organic phase was washed water, dried and concentrated to give an oil which was purified by chromatography (silica gel: 10% ethyl acetate/iso-hexane), to afford the intermediate (a), N-BOC-(R)-2-(4-ethoxybenzyl)morpholine as a pale yellow oil (0.205 g, 63% yield).

LC (50% to 80% gradient 210 nm XTERRA 2 ml/min) 99.7% @ 4.77 min

Mass spec: found [MH]$^+$ 322.

Example 23

(R)-2-(3-bromo-4-cyclopropyloxy)benzyl)morpholine

N-BOC-(R)-2-(3-bromo-4-hydroxybenzyl)morpholine, example 4, intermediate (a) (70 mg, 0.19 mmo) was dissolved in acetone (1.5 mL) and treated with potassium carbonate (78 mg, 0.56 mmol) and bromomethylcyclopropane (76 mg, 0.56 mmol) was added and the resulting reaction was shaken at 55° C. for 16 hrs. The reaction was filtered and concentrated under a flow of nitrogen. The crude residue was dissolved in tetrahydrofuran (8 mL) with polymer supported diphenylphosphine (0.5 g) and shaken for 4 hrs. The reaction was then filtered and concentrated under a high flow of nitrogen. The crude residue was dissolved in TFA (20% v/v solution in dichloromethane, 2.5 mL) and shaken for 3 hrs at room temperature. The reaction mixture was added directly to an SCX-2 column (2 g) and washed with dichloromethane (2 mL×2) and methanol (2 mL×2). The SCX-2 column was then washed with ammonia (2N in methanol, 3×2 mL). Combined ammonia washes were concentrated in vacuo to yield the desired morpholine example 23 as a colorless oil (19 mg).

LC (50% to 80% gradient 210 nm XTERRA 2 ml/min) 99.1% @ 1.84 min.

Mass spec: found [MH]$^+$ 326/328.

Example 24

(R)-2-(4-methoxy-3-vinylbenzyl)-morpholine

Tetrakis(triphenylphosphine)palladium(0) (31 mg, 0.027 mmol) was added to a solution of N-Boc-(R)-2-(3-iodo-4-methoxybenzyl)morpholine, example 17, intermediate (b), (115 mg, 0.266 mmol), potassium carbonate (74 mg, 0.532 mmol), tetraethylammonium chloride (44 mg, 0.266 mmol) and tributylvinylstannane (0.077 mL, 0.266 mmol) in N,N-dimethyl formamide (10 mL) and heated to 90° C. for 2 h. The cooled reaction mixture was filtered and the liquors partitioned between ethyl acetate and water. The organic phase was separated, dried (Na$_2$SO$_4$) and concentrated and the residue purified by silica gel chromatography to give the N-Boc protected material that was deprotected using hydrogen chloride in dioxane-methanol and purified by HPLC to afforded example 24 as a colorless oil (4 mg, 6.5%).

LC (50% to 80% gradient 220 nm XTERRA 2 ml/min) 97.3% @ 1.0 min.

Mass spec: [MH]$^+$ 234.

Example 25

(R)-2-(3-hydroxyimino-4-methoxybenzyl)morpholine

Intermediate (a) N-BOC-(R)-2-(3-hydroxyimino-4-methoxybenzyl)morpholine (85 mg, 0.24 mmol) was dissolved in TFA (20% v/v in dichloromethane, 5 mL total) and stirred at room temperature for 2 hrs. The reaction mixture was added directly to an SCX-2 column (1 g) and washed with dichloromethane (2 mL×2) and methanol (2 mL×2). The SCX-2 column was then washed with ammonia (2N in methanol, 3×2 mL). Combined ammonia washes were concentrated in vacuo to yield the crude product as a yellow solid (38 mg). The crude material was purified by HPLC to yield the desired morpholine example 25 as a white powder (12 mg).

LC (50% to 80% gradient 210 nm XTERRA 2 ml/min) 100% @ 1.84 min.

Mass spec: found [MH]$^+$ 251.

Intermediates

N-BOC-(R)-2-(3-hydroxyimino-4-methoxybenzyl)morpholine

Intermediate (b) N-BOC-(R)-2-(3-formyl-4-hydroxybenzyl)morpholine (0.192 g, 0.06 mmol) was dissolved in dry acetone (5 mL) with potassium carbonate (0.165 g, 1.19 mmol), under an atmosphere of nitrogen and iodomethane (0.074 mL, 1.19 mmol) added in one portion. The resulting mixture was stirred at room temperature for 18 hrs and then concentrated in vacuo. The residue was dissolved in water (10 mL) and extracted with diethyl ether (10 mL). The organic layer was dried (Na$_2$SO$_4$), filtered and concentrated in vacuo. The orange oil was purified by column chromatography (silica; 35% ethyl acetate/isohexane) to yield the desired product as a yellow oil (0.157 g, 78%). The material was used directly in the next step. N-BOC-(R)-2-(3-formyl-4-methoxybenzyl)morpholine (0.157 g, 0.468 mmol) was dissolved in ethanol (5 mL) and added to a solution of hydroxylamine hydrochloride (42 mg, 0.61 mmol) and sodium acetate (88 mg, 1.08 mmol) in ethanol (5 mL) at room temperature. The resulting mixture was stirred at room temperature for 18 hrs and then heated at 80° C. for 72 hrs. The reaction mixture was diluted with water (40 mL) and extracted with ethyl acetate (20 mL×2). Combined organic layers were washed with brine (10 mL), dried (Na$_2$SO$_4$), filtered and concentrated in vacuo to yield the desired intermediate (a), N-BOC-(R)-2-(3-hydroxyimino-4-methoxybenzyl)morpholine as a yellow oil (85 mg).

LC (20% to 50% gradient 220 nm XTERRA 2 ml/min) 91.3% @ 2.86 min.

Mass spec: [MH]$^+$ 351.

N-BOC-(R)-2-(3-formyl-4-hydroxybenzyl)morpholine

N-BOC-(R)-2-(4-hydroxybenzyl)morpholine, example 4, intermediate (b) (0.648 g, 2.21 mmol), was dissolved in acetonitrile (20 mL), with magnesium chloride (0.316 g, 3.32 mmol), triethylamine (1.16 mL, 8.29 mmol) and paraformaldehyde (0.448 g, 14.9 mmol) added in one portion. The reaction mixture was then heated at 90° C. for 24 hrs. The reaction was allowed to cool, poured into hydrochloric acid (5% v/v water) and extracted with diethyl ether (40 mL). The organic layer was washed with water (20 mL), brine (20 mL) dried (Na$_2$SO$_4$), filtered and concentrated in vacuo. The residue was purified by column chromatography (silica; 15% ethyl acetate/iso-hexane) to yield the desired aldehyde N-BOC-(R)-2-(3-formyl-4-hydroxybenzyl)morpholine, intermediate (b), as a pale yellow oil (0.239 g, 34%).

LC (20% to 50% gradient 220 nm XTERRA 2 ml/min) 99.8% @ 3.00 min.

Mass spec: [M–H]–320.

Example 26

(R)-2-(3-(2-phenoxyethyloxymethyl)benzyl)morpholine

N-Boc-(R)-2-(3-(hydroxymethyl)benzyl)morpholine (example 95, intermediate (b)) was reacted with NaH, and betabromophenetole using the procedure described for example 97. This material was then deprotected using TFA (20% v/v in dichloromethane) to yield the desire morpholine example 26 as a colorless oil (60 mg, 98%).

LC (50% to 80% gradient 210 nm XTERRA 2 ml/min) 92.4% @ 2.23 min.

Mass spec: found [MH]$^+$ 328.

Example 27

(R)-2-(3-chloro-4-cyclopropylmethoxybenzyl)morpholine

Sodium hydride (50 mg, 1.25 mmol) was washed twice with isohexane and then suspended in anhydrous N,N-dimethyl formamide (0.5 mL), under an atmosphere of nitrogen and cooled to 0° C. Then cyclopropylmethanol (90 mg, 1.25 mmol) was added. When effervescence had finished intermediate (a), N-Benzyl-(R)-2-(3-chloro-4-fluorobenzyl)morpholine (0.10 g, 0.31 mmol) was added as a solution in N,N-dimethyl formamide (1.0 mL). The reaction was then warmed to 100° C. (bath temperature) for 6 hrs and cooled to room temperature. The mixture was poured into water (25 mL) and extracted with ethyl acetate (25 mL). The organic layer was washed with brine (10 mL×2), dried (MgSO$_4$), filtered and concentrated in vacuo. The residue was purified by column chromatography (silica; 20% ethyl acetate/isohexane) to give a residue that was added to an SCX-2 column (10 g) as a solution in dichloromethane, washed with dichloromethane (6 mL×2) and methanol (6 mL×2). The SCX-2 column was then washed with ammonia (2N in methanol, 3×6 mL). Combined ammonia washes were concentrated in vacuo to yield the desired product as colorless oil (85 mg). N-Benzyl-(R)-2-(4-cyclopropylmethoxy-3-chlorobenzyl)morpholine (82 mg, 0.22 mmol) was then dissolved in 1,2-dichloroethane (3 mL) and treated with 1-chloro-ethyl-chloroformate (94 mg, 0.66 mmol) and heated at 85° C. for 3 hrs. The reaction mixture was then concentrated in vacuo. The residue was dissolved in methanol (7 mL) and heated at 75° C. for 2.5 hrs. The reaction mixture was then concentrated in vacuo. The crude residue was dissolved in dichloromethane (1 mL) and the solution poured onto a SCX-2 column (2 g), eluting with dichloromethane (2 ml×2) and methanol (2 mL×2). The column was then washed with ammonia (2N in methanol, 2 mL×2). The ammonia washes were concentrated in vacuo. The crude residue was purified by preparative chiral HPLC to yield the desired morpholine example 27 as a yellow oil (10 mg).

LC (50% to 80% gradient 210 nm XTERRA 2 ml/min) 97.5% @ 1.67 min.

Mass spec: [MH]$^+$ 282.

Intermediates

A) N-Benzyl-(R)-2-(3-chloro-4-fluorobenzyl)morpholine 1-chloro-3-(3-chloro-4-fluorophenyl)-2-propanol, was prepared using the procedure as described for example 2, intermediate (d), but starting from 5-bromo-2-fluoro-chlorobenzene and (R)-epichlorohydrin. In turn 3-chloro-4-fluorobenzylmorpholine was made using the procedure described for example 1, intermediate (d), but using 1-chloro-3-(3-chloro-4-fluorophenyl)-2-propanol.

3-chloro-4-fluorobenzylmorpholine (4.25 mmol) was dissolved in dichloromethane (50 mL) and treated with benzaldehyde (0.531 g, 5 mmol) and sodium triacetoxyborohydride (1.06 g, 5 mmol). The reaction was stirred at room temperature for 18 hrs and then diluted with sodium hydrogen carbonate (saturated aqueous solution, 50 mL) shaken and layers separated. The aqueous layer was then extracted with dichloromethane (30 mL) and combined organic layers washed with brine (30 mL), dried (MgSO4), filtered. The solution was stirred with polymer supported trisamine (1.0 g, 4.61 mmol/g) at room temperature for 1 hr. The mixture was filtered, washed with dichloromethane (10 mL×2) and combined washes concentrated in vacuo to yield the desired intermediate 26, N-Benzyl-(R)-2-(3-chloro-4-fluorobenzyl) morpholine.

LC (5%IPA/95%hexane isocratic 220 nm ChiralPak AD column 1 ml/min) 94.33% @ 5.28 min.

Mass spec: found [MH]$^+$ 320.

Example 28

(R)-2-(3-chloro-4-ethoxybenzyl)morpholine

N-BOC-(R)-2-(3-chloro-4-hydroxybenzyl)morpholine, example 7, intermediate (a) (52 mg, 0.16 mmol), was dissolved in acetone (1.5 mL) with potassium carbonate (44 mg, 0.32 mmol) and iodoethane (38 uL, 0.47 mmol) added in one portion. The reaction was then heated to 55° C. and shaken at that temperature for 16 hrs. The reaction mixture was filtered, washing with acetone (1 mL×2) and the liquor evaporated under a high flow of nitrogen. The residue was dissolved in tetrahydrofuran: ethanol (1:1, 4 mL) and polymer supported thiophenol (0.43 g, 0.64 mmol), MP-carbonate (0.24 g, 0.64 mmol) and diisopropylethylamine (119 uL, 0.68 mmol) added. The reaction was shaken for 24 hrs, then filtered and concentrated under a high flow of nitrogen. The crude residue was dissolved in TFA (20% v/v solution in dichloromethane, 2.0 mL) and shaken for 3 hrs at room temperature. The reaction mixture was added directly to an SCX-2 column (2 g) and washed with dichloromethane (2 mL×2) and methanol (2 mL×2). The SCX-2 column was then washed with ammonia (2N in methanol, 3×2 mL). Combined ammonia washes were concentrated in vacuo. The residue was then purified by preparative HPLC to yield the desired morpholine example 28 as a colorless oil (17 mg).

LC (50% to 80% gradient 210 nm XTERRA 2 ml/min) 96.4% @ 1.06 min.

Mass spec: found [MH]$^+$ 257.

Example 29

(R)-2-(2-hydroxybenzyl)morpholine

Example 1, intermediate (c), was deprotected in 2% trifluoroacetic acid in dichloromethane (15 mL) over 18 hrs at room temperature to afford the morpholine example 29 as a colorless liquid (9 mg, 12%).

LC (20% to 50% gradient 210 nm XTERRA 2 ml/min) 97.2% @ 0.97 min.

Mass spec: [MH]$^+$ 194

Example 30

(R)-2-(4-Chloro-3-methyl-benzyl)-morpholine

The title compound was synthesized in analogy to example 83 from (R)-1-chloro-3-(4-chloro-3-methyl-phenyl)-propan-2-ol to give the title compound as a colorless oil (13%).

MS (ISP): 226.2 (M+H$^+$)

Intermediates (R)-1-Chloro-3-(4-chloro-3-methyl-phenyl)-propan-2-ol

The solution of 1.0 g (4.9 mmol) 5-bromo-2-chlorotoluene in 10 mL toluene was cooled down to −70° C. and treated dropwise with 3.6 mL (5.4 mmol; 1.5M solution in toluene) tert-butyllithium. After 30 min. 0.42 mL (5.3 mmol) (R)-(−)-epichlorohydrin was added and the temperature was allowed to rise to 0° C. After 1 h the reaction mixture was diluted with ethyl acetate and extracted with 10% aqueous sodium bicarbonate solution followed by brine. The organic layer was dried over magnesium sulfate, filtered and evaporated and the residue was purified by column chromatography on silica gel with n-hexane:ethyl acetate (1:1) as eluant to give the title compound as a colorless oil (44.8%).

MS (EI): 217.9, 219.9 (M)

Example 31

(R)-2-(3-(2-(4-pyridinyl)ethyl)benzyl)morpholine

Intermediate (a) N-Boc-(R)-2-(3-(2-(4-pyridinyl)vinyl)-benzyl)morpholine (43 mg) was dissolved in ethanol (10 mL) with palladium (10% w/w on charcoal, 5 mg) and stirred at room temperature under a hydrogen atmosphere for 4.5 hrs. The reaction mixture was filtered and concentrated in vacuo. The residue (39 mg) was stirred in TFA (20% v/v in dichloromethane, 1.25 mL) at room temperature for 4 hrs. The reaction was poured onto an SCX-2 column (2 g) and washed with dichloromethane (2 mL×2) and methanol (2 mL×2). The SCX-2 column was then washed with ammonia (2N in methanol, 3×2 mL). Combined ammonia washes were concentrated in vacuo to yield the desired morpholine example 31 as a yellow oil (23.5 mg).

LC (50% to 80% gradient 210 nm XTERRA 2 ml/min) 99.0% @ 0.83 min.

Mass spec: found [MH]$^+$ 283.

Intermediates

N-Boc-(R)-2-(3-(2-(4-pyridinyl)vinyl)-benzyl)morpholine

Intermediate (b) N-Boc-(R)-2-(3-bromobenzyl)morpholine (103 mg, 0.29 mmol), was dissolved in CH$_3$CN (2 mL) with palladium acetate (3.2 mg, 14 umol), tris(ortho-tolyl)phosphine (8.8 mg, 29 umol), 4-vinylpyridine (61 mg, 0.58 mmol) and triethyl amine (58 mg, 0.58 mmol). The reaction was then subjected to microwave heating at 140° C. for 5 minutes. The reaction was cooled to room temperature, partitioned between ethyl acetate (20 mL) and water (20 mL) and separated. The organic layer was washed with brine (10 mL), dried (MgSO$_4$), filtered and concentrated in vacuo. The residue was purified by column chromatography (silica; 20-30% ethyl acetate/isohexane) to yield the desired intermediate (a), N-Boc-(R)-2-(3-(2-(4-pyridinyl)vinyl-benzyl) morpholine as a colorless gum (63 mg, 57%).

LC (50% to 80% gradient 210 nm XTERRA 2 ml/min) 98.0% @ 7.69 min.

Mass spec: [MH]⁺ 381

N-Boc-(R)-2-(3-Bromobenzyl)morpholine

Example 15 (0.502 g, 1.95 mmol) was dissolved in dichloromethane (5 mL), cooled to 0° C. and di-tertiary-butyl-dicarbonate (0.49 mL, 2.15 mmol) added in one portion. The reaction was allowed to stir at room temperature for 72 hrs. The reaction was then concentrated in vacuo and purified by column chromatography (silica; 10% ethyl acetate/iso-hexane) to yield the desired, intermediate (b), N-Boc-(R)-2-(3-Bromobenzyl)morpholine, as a colorless oil (0.58 g, 83%).

LC (50% to 80% gradient 210 nm XTERRA 2 ml/min) 97.4% @ 5.62 min.

Mass spec: [MH]+356/358.

Example 32

(R)-2-(4-(morpholin-2-yl)methyl-3-bromo)phenoxy-acetonitrile

N-BOC-(R)-2-(3-bromo-4-hydroxybenzyl)morpholine, example 4, intermediate (a) (60 mg, 0.16 mmol) was dissolved in acetone (1.5 mL) and treated with potassium carbonate (45 mg, 0.32 mmol) and 2-bromoacetonitrile (27 uL, 0.39 mmol) was added and the resulting reaction was shaken at 55° C. for 16 hrs. The reaction was filtered and concentrated under a flow of nitrogen. The crude residue was dissolved in tetrahydrofuran (8 mL) with polymer supported diphenylphosphine (0.5 g) and shaken for 7 hrs. The reaction was then filtered and concentrated in vacuo. The crude residue was dissolved in TFA (20% v/v solution in dichloromethane, 2.0 mL) and shaken for 4 hrs at room temperature. The reaction mixture was added directly to an SCX-2 column (2 g) and washed with dichloromethane (2 mL×2) and methanol (2 mL×2). The SCX-2 column was then washed with ammonia (2N in methanol, 3×2 mL). Combined ammonia washes were concentrated in vacuo. The residue was purified by preparative HPLC to yield the desired morpholine example 32 as a colorless gum (10 mg).

LC (50% to 80% gradient 210 nm XTERRA 2 ml/min) 74% @ 0.80 min.

Mass spec: found [MH]⁺ 311/313.

Example 33

(R)-2-(3-Methylbenzyl)morpholine (R)-1-chloro-3-(3-methylphenyl)-2-propanol, was prepared, using the same procedure as described for example 2, intermediate (d), but from 3-bromo-toluene and (R)-epichlorohydrin. Example 33 was prepared as described for example 1, intermediate (d), but using (R)-1-chloro-3-(3-methylphenyl)-2-propanol, to obtain the desired morpholine, example 33 as a colorless oil (0.54 g, 37.5%).

LC (20% to 50% gradient 210 nm XTERRA 2 ml/min) 95.4% @ 2.16 min.

Mass spec: [MH]+192.

Example 34

(R)-2-(2-Difluoromethoxybenzyl)morpholine

Deprotection of intermediate (a), N-Boc-(R)-2-(2-difluoromethoxybenzyl)morpholine using hydrogen chloride (4M, in methanol), afforded the morpholine example 34 as a colorless oil (37 mg, 65%).

LC (50% to 80% gradient 220 nm XTERRA 2 ml/min) 98.6% @ 0.71 min.

Mass spec: found [MH]⁺ 244

Intermediates

N-Boc-(R)-2-(2-difluoromethoxybenzyl)morpholine

To a solution of powdered KOH (450 mg, 8.02 mmol) in IPA (7 ml) was added, dropwise, a solution of example 1, intermediate (c), (392 mg, 1.336 mmol) in IPA-ethanol (1:1 ratio, 10 ml). The solution was stirred at 24° C. for 30 mins then cooled to –14° C. whilst passing difluorochloromethane gas through the solution for 20 mins. Stirring was continued for 30 mins before warming to 24° C. over 15 hrs. The reaction mixture was partitioned between water and ethyl acetate. The organic phase was separated, dried and concentrated. Purification by silica chromatography (10% ethyl acetate/iso-hexane) afforded the desired product intermediate (a), N-Boc-(R)-2-(2-difluoromethoxybenzyl)morpholine (82 mg, 18%).

LC (50% to 80% gradient 220 nm XTERRA 2 ml/min) 95.2% @ 4.53 min.

Mass spec: found [MH]⁺ 344

Example 35

(S)-2-(3-Bromo-4-methoxybenzyl)morpholine

Example 35 was prepared using the same procedure as described for example 9 but starting from (S)-epichlorohydrin.

LC (50% to 80% gradient 210 nm XTERRA 2 ml/min) 100% @ 0.87 min.

Mass spec: [MH]⁺ 286/288.

Example 36

(R)-2-(3-bromo-4-(2-methoxyethyloxy)benzyl)morpholine

N-BOC-(R)-2-(3-bromo-4-hydroxybenzyl)morpholine, example 4, intermediate (a), (70 mg, 0.19 mmo) was dissolved in acetone (1.5 mL) and treated with potassium carbonate (78 mg, 0.56 mmol) and 2-bromoethylmethyl ether (78 mg, 0.56 mmol) was added and the resulting reaction was shaken at 55° C. for 16 hrs. The reaction was filtered and concentrated under a flow of nitrogen. The crude residue was dissolved in tetrahydrofuran (8 mL) with polymer supported diphenylphosphine (0.5 g) and shaken for 4 hrs. The reaction was then filtered and concentrated under a high flow of nitrogen. The crude residue was dissolved in TFA (20% v/v solution in dichloromethane, 2.5 mL) and shaken for 3 hrs at room temperature. The reaction mixture was added directly to an SCX-2 column (2 g) and washed with dichloromethane (2 mL×2) and methanol (2 mL×2). The SCX-2 column was then washed with ammonia (2N in methanol, 3×2 mL). Combined ammonia washes were concentrated in vacuo to yield the desired morpholine example 36 as a colorless oil (31 mg).

LC (50% to 80% gradient 210 nm XTERRA 2 ml/min) 97.9% @ 0.79 min.

Mass spec: found [MH]⁺ 330/332.

Example 37

(R)-2-(4-(2,2,2-trifluoroethoxy)-3-trifluoromethyl-benzyl)morpholine

To a suspension of sodium hydride (43 mg, 1.08 mmol) in N,N-dimethyl formamide (3 mL) at 0° C. was added 2,2,2- trifluroethanol (108 mg, 1.08 mmol), and the resultant mixture stirred for 5 mins. N-Boc-(R)-2-(4-fluoro-3-trifluoromethylbenzyl)morpholine, example 2, intermediate (b) (98 mg, 0.27 mmol) was added in one portion as a solution in N,N-dimethyl formamide (1.5 mL) and the reaction mixture warmed to 105° C. and stirred at that temperature for 6 hrs. The reaction was cooled to room temperature and poured into water (20 ml). The suspension was extracted with ethyl acetate (20 mL×2). Combined organic extracts were washed with water (25 mL×2) and brine (25 mL), dried (MgSO$_4$), filtered and concentrated in vacuo. The residue was purified by column chromatography (silica; 20% ethyl acetate/isohexane) to yield the desired product as a colorless oil (87 mg) and used directly in the next reaction. The crude material was deprotected using TFA (20% v/v in dichloromethane, 2 mL) over 3 hrs, poured onto an SCX-2 column (2 g) and washed with dichloromethane (2 mL×2) and dichloromethane: methanol (1:1, 2 mL×2). The column was then washed with ammonia (2N solution in methanol, 2 mL×3) and the ammonia washes were concentrated in vacuo to yield the desired morpholine example 37 a colorless oil (59 mg).

LC (50% to 80% gradient 210 nm XTERRA 2 ml/min) 97.9% @ 1.89 min.

Mass spec: [MH]$^+$ 344.

Example 38

(R)-2-(3-bromo-4-(propyl-2-yn-1-oxy)benzyl)morpholine

N-BOC-(R)-2-(3-bromo-4-hydroxybenzyl)morpholine, example 4, intermediate (a) (60 mg, 0.16 mmo) was dissolved in acetone (1.5 mL) and treated with potassium carbonate (45 mg, 0.32 mmol) and propargyl bromide (47 uL, 0.47 mmol) was added and the resulting reaction was shaken at 55° C. for 16 hrs. The reaction was filtered and concentrated under a flow of nitrogen. The crude residue was dissolved in tetrahydrofuran (8 mL) with polymer supported diphenylphosphine (0.5 g) and shaken for 7 hrs. The reaction was then filtered and concentrated in vacuo. The crude residue was dissolved in TFA (20% v/v solution in dichloromethane, 2.0 mL) and shaken for 4 hrs at room temperature. The reaction mixture was added directly to an SCX-2 column (2 g) and washed with dichloromethane (2 mL×2) and methanol (2 mL×2). The SCX-2 column was then washed with ammonia (2N in methanol, 3×2 mL). Combined ammonia washes were concentrated in vacuo. The residue was purified by preparative HPLC to yield the desired morpholine example 38 as a colorless oil (26 mg).

LC (50% to 80% gradient 210 nm XTERRA 2 ml/min) 85%% @ 1.00 min.

Mass spec: found [MH]$^+$ 310/312.

Example 39

(R)-2-(3-chloro-4-(prop-2-yn-1-yloxy)benzyl)morpholine

N-BOC-(R)-2-(3-chloro-4-hydroxybenzyl)morpholine, example 7, intermediate (a) (52 mg, 0.16 mmol), was dissolved in acetone (1.5 mL) with potassium carbonate (44 mg, 0.32 mmol) and propargyl bromide (53 uL, 0.47 mmol) added in one portion. The reaction was then heated to 55° C. and shaken at that temperature for 16 hrs. The reaction mixture was filtered, washing with acetone (1 mL×2) and the liquor evaporated under a high flow of nitrogen. The residue was dissolved in tetrahydrofuran: ethanol (1:1, 4 mL) and polymer supported thiophenol (0.43 g, 0.64 mmol), MP-carbonate (0.24 g, 0.64 mmol) and diisopropylethylamine (119 uL, 0.68 mmol) added. The reaction was shaken for 24 hrs, then filtered and concentrated under a high flow of nitrogen. The crude residue was dissolved in TFA (20% v/v solution in dichloromethane, 2.0 mL) and shaken for 3 hrs at room temperature. The reaction mixture was added directly to an SCX-2 column (2 g) and washed with dichloromethane (2 mL×2) and methanol (2 mL×2). The SCX-2 column was then washed with ammonia (2N in methanol, 3×2 mL). Combined ammonia washes were concentrated in vacuo to yield the desired morpholine example 39 as a colorless oil (20 mg).

LC (50% to 80% gradient 210 nm XTERRA 2 ml/min) 94.5% @ 0.88 min.

Mass spec: found [MH]$^+$ 266.

Example 40

(R)-2-(4-(2,2,2-trifluoroethoxy)-3-chlorobenzyl) morpholine

To a suspension of sodium hydride (50 mg, 1.25 mmol) in N,N-dimethyl formamide (0.5 mL) at 0° C. was added 2,2,2-trifluroethanol (125 mg, 1.25 mmol), and the resultant mixture stirred for 5 mins. N-Benzyl-(R)-2-(4-fluoro-3-chlorobenzyl)morpholine, example 27, intermediate (a) (100 mg, 0.31 mmol) was added in one portion as a solution in N,N-dimethyl formamide (1.0 mL) via syringe and the reaction mixture warmed to 10° C. and shaken at that temperature for 18 hrs. The reaction was cooled to room temperature and poured into water (20 ml). The suspension was extracted with ethyl acetate (20 mL×2). Combined organic extracts were washed with water (20 mL×2) and brine (25 mL), dried (MgSO$_4$), filtered and concentrated in vacuo. The residue was purified by column chromatography (silica; 20% ethyl acetate/isohexane) to yield the desired product as a light yellow oil (38 mg) and used directly in the next reaction. The material was dissolved in 1,2-dichloroethane (2 mL), and 1-chloro-ethyl-chloroformate (33 mg, 0.23 mmol) added in one portion. The resulting mixture was heated at 90° C. for 24 hrs. The reaction was then concentrated in vacuo. The residue was dissolved in methanol (10 mL), and heated at 80° C. for 5 hrs. The reaction was cooled to room temperature and concentrated in vacuo. The residue was dissolved in dichloromethane and poured onto an SCX-2 column (2 g) and washed with dichloromethane (2 mL×2) and methanol (2 mL×2). The column was then washed with ammonia (2N solution in methanol, 2 mL×3) and the ammonia washes were concentrated in vacuo to yield example 40 as a yellow oil (20 mg).

LC (50% to 80% gradient 210 nm XTERRA 2 ml/min) 94.7% @ 1.49 min.

Mass spec: [MH]$^+$ 310.

Example 41

(R)-2-(3-vinylbenzyl)morpholine (R)-1-chloro-3-(3-vinylphenyl)-2-propanol, was prepared, using the same procedure as described for example 2, intermediate (d), but from 3-bromostyrene and (R)-epichlorohydrin. Example 41 was prepared as described for example 1, intermediate (d), but using (R)-1-chloro-3-(3-vinylphenyl)-2-propanol, to obtain the desired morpholine, example 41 as a colorless oil (440 mg, 17%).

LC (20% to 50% gradient 220 nm XTERRA 2 ml/min) 98.2% @ 3.49 min.
Mass spec: [MH]+204.

Example 42

(R)-2-(3-chloro-6-fluorobenzyl)morpholine (R)-1-chloro-3-(3-chloro-6-fluorophenyl)-2-propanol was prepared, using the same procedure as described for example 2, intermediate (d), but from 2-bromo-4-chlorofluorobenzene and (R)-epichlorohydrin. Example 42 was prepared as described for example 1, intermediate (d), but using (R)-1-chloro-3-(3-chloro-6-fluorophenyl)-2-propanol, to obtain the desired morpholine, example 42 as a yellow oil (9.7 mg).
LC (50% to 80% gradient 210 nm XTERRA 2 ml/min) 97.3% @ 0.97 min.
Mass spec: [MH]+230.

Example 43

(R)-2-(3-chloro-4-(2-methoxyethyloxy)benzyl)morpholine

N-BOC-(R)-2-(3-chloro-4-hydroxybenzyl)morpholine, example 7, intermediate (a) (52 mg, 0.16 mmol), was dissolved in acetone (1.5 mL) with potassium carbonate (44 mg, 0.32 mmol) and 2-bromoethylmethyl ether (44 uL, 0.47 mmol) added in one portion. The reaction was then heated to 55° C. and shaken at that temperature for 16 hrs. The reaction mixture was filtered, washing with acetone (1 mL×2) and the liquor evaporated under a high flow of nitrogen. The residue was dissolved in tetrahydrofuran:ethanol (1:1, 4 mL) and polymer supported thiophenol (0.43 g, 0.64 mmol), MP-carbonate (0.24 g, 0.64 mmol) and diisopropylethylamine (119 uL, 0.68 mmol) added. The reaction was shaken for 24 hrs, then filtered and concentrated under a high flow of nitrogen. The crude residue was dissolved in TFA (20% v/v solution in dichloromethane, 2.0 mL) and shaken for 3 hrs at room temperature. The reaction mixture was added directly to an SCX-2 column (2 g) and washed with dichloromethane (2 mL×2) and methanol (2 mL×2). The SCX-2 column was then washed with ammonia (2N in methanol, 3×2 mL). Combined ammonia washes were concentrated in vacuo to yield the desired morpholine example 43 as a colorless oil (19 mg).
LC (50% to 80% gradient 210 nm XTERRA 2 ml/min) 99.7% @ 0.70 min.
Mass spec: found [MH]$^+$ 286.

Example 44

(R)-2-(3-chloro-4-(3-pyridinylmethoxy)benzyl)morpholine

N-BOC-(R)-2-(3-chloro-4-hydroxybenzyl)morpholine, example 7, intermediate (a) (53 mg, 0.16 mmol), was dissolved in dichloromethane (4 mL) with 3-pyridinyl carbinol (35 mg, 0.32 mmol) shaken at room temperature for 20 mins and diisopropylazodicarboxylate (65 mg, 0.32 mmol) added in one portion. dichloromethane (6 mL) was added to solvate the polymer. The reaction mixture was shaken for 24 hrs then filtered. Polymer supported toluenesulfonyl chloride (0.18 g, 2.82 mmol/g) and MP-carbonate (0.39 g, 2.62 mmol/g) were added to the liquor and the mixture shaken for 6 hrs. The reaction was filtered and evaporated under a high flow of nitrogen. The crude residue was dissolved in TFA (20% v/v solution in dichloromethane, 2.0 mL) and shaken for 3 hrs at room temperature. The reaction mixture was added directly to an SCX-2 column (2 g) and washed with dichloromethane (2 mL×2) and methanol (2 mL×2). The SCX-2 column was then washed with ammonia (2N in methanol, 3×2 mL). Combined ammonia washes were concentrated in vacuo and the residue purified by preparative HPLC to yield the desired morpholine example 44 as a colorless oil (9 mg).
LC (50% to 80% gradient 210 nm XTERRA 2 ml/min) 99% @ 0.89 min.
Mass spec: found [MH]$^+$ 319.

Example 45

(R)-2-[3-(6-Chloro-pyridin-3-yl)-benzyl]-morpholine

The title compound was synthesized in analogy to example 83 from(R)-2-[3-(6-chloro-pyridin-3-yl)-benzyl]-morpholine-4-carboxylic acid tert-butyl ester to give the desired product as colorless oil (61%).
MS (ISP): 289.1 (M+H$^+$)

Intermediates (R)-2-[3-(6-Chloro-pyridin-3-yl)-benzyl]-morpholine-4-carboxylic acid tert-butyl ester
To the solution of 0.30 g (0.84 mmol) (R)-2-(3-bromo-benzyl)-morpholine-4-carboxylic acid tert-butyl ester (example 97, intermediate (d)) in 12 mL 1,2-dimethoxyethane 97 mg (84 μmol) tetrakis(triphenylphosphine)palladium(0) were added. After 30 min. 0.48 g (3.0 mmol) 2-chloropyridine-5-boronic acid and 0.22 g (2.1 mmol) sodium bicarbonate dissolved in 6 mL water were added successively and the reaction stirred for 2.5 h under reflux. After cooling down to room temperature the reaction mixture was poured on saturated aqueous potassium carbonate solution and extracted three times with ethyl acetate. The organic layers were washed with brine, dried over magnesium sulfate, filtered and evaporated. The residue was purified by column chromatography using MPLC on silica gel with ethyl acetate: n-heptane (1:1) as eluant to give the compound as colorless oil (35%).
MS (EI): 388.1 (M)

Example 46

(R)-2-(3-bromo-4-methoxy-5-methyl-benzyl)morpholine

Intermediate (a), N-Boc-(R)-2-(3-bromo-4-methoxy-5-methyl-benzyl)morpholine was deprotected, using the same procedure as described for example 1 to obtain the desired morpholine, example 46 as a colorless oil (40 mg, 68%).
LC (50% to 80% gradient 210 nm XTERRA 2 ml/min) 88.8% @ 1.02 min.
Mass spec: [MH]+300/302.

Intermediates

N-Boc-(R)-2-(3-bromo-4-methoxy-5-methyl-benzyl)morpholine
N-Boc-(R)-2-(3-bromo-4-methoxy-5-methyl-benzyl)morpholine, intermediate (b), was brominated using the same procedure as described for example 1, intermediate (b), N-Boc-(R)-2-(5-Bromo-2-hydroxybenzyl)morpholine.

N-Boc-(R)-2-(4-methoxy-3-methyl-benzyl)morpholine (R)-2-(3-methyl-4-methoxybenzyl)morpholine, Example 13 was protected with tertiary-butoxycarbonyl as described for example 9, intermediate (b).

Example 47

(R)-2-(3-fluoro-4-methoxybenzyl)morpholine (R)-1-chloro-3-(3-fluoro-4-methoxy)-2-propanol was prepared, using the same procedure as described for example 2, intermediate (d), but from 4-bromo-2-fluoroanisole and (R)-epichlorohydrin. Example 47 was prepared as described for example 1, intermediate (d), but using (R)-1-chloro-3-(3-fluoro-4-methoxy)-2-propanol, to obtain the desired morpholine, example 47 as a pale yellow oil (0.12 g, 19%).

LC (20% to 50% gradient 210 nm XTERRA 2 ml/min) 93.5% @ 1.86 min.

Mass spec: [MH]+226.

Example 48

(R)-2-(3-(2-(3-pyridinyl)ethyl)benzyl)morpholine

N-Boc-(R)-2-(3-(2-(3-pyridinyl)vinyl)-benzyl)morpholine intermediate (a) was dissolved in ethanol (8 mL), with palladium on charcoal (10% w/w, 5 mg) and stirred at room temperature under an atmosphere of hydrogen (1 balloon containing hydrogen) for 18 hours. The reaction was filtered through a pad of celite, washing with ethanol, and the solution was concentrated in vacuo. The crude material was used in the next step without further purification. N-Boc-(R)-2-(3-(2-(3-pyridinyl)ethyl)-benzyl)morpholine (25 mg), was dissolved in a solution of TFA in dichloromethane (20% v/v, 1 mL total) and stirred at room temperature for 3 hrs. The reaction was then poured through an SCX-2 column and washed with dichloromethane. The column was then washed with ammonia (2N, methanol) and the ammonia washes concentrated in vacuo. The residue was purified by column chromatography (prepacked silica, 1 g; dichloromethane/ methanol/ammonium hydroxide, 100:10:1) to obtain the desired product example 48 (R)-2-(3-(2-(3-pyridinyl)ethyl) benzyl)morpholine as a yellow oil (10 mg).

LC (20% to 50% gradient 210 nm XTERRA 2 ml/min) 90.2% @ 4.88 min.

Mass spec: [MH]+283.

Intermediates

N-Boc-(R)-2-(3-(2-(3-pyridinyl)vinyl)-benzyl)morpholine

To a small reaction vessel was added palladium acetate (1.5 mg, 7micromol), tris-(ortho-toluyl)phospine (4.2 mg, 14micromol) and 3-bromopyridine (22 mg, 0.13 mmol) as a solution in acetonitrile (1.5 mL) in one portion. The mixture was stirred for 5 minutes at room temperature under an atmosphere of nitrogen gas and then intermediate (b), N-Boc-(R)-2-(3-vinylbenzyl)morpholine (0.083 g, 0.27 mmol) was added as a solution in acetonitrile (1.5 mL). The reaction vessel was then subjected to microwave power to heat the reaction to 140° C. for 5 minutes and then cooled to room temperature. The crude reaction was added directly to a silica column and the mixture washed with solvent (10-60% ethyl acetate:isohexane). The desired material was concentrated in vacuo and purified by column chromatography (silica; 50% ethyl acetate: isohexane) to obtain the desired coupling product intermediate (a), N-Boc-(R)-2-(3-(2-(3-pyridinyl)vinyl)-benzyl)morpholine as a colorless oil (30 mg, 57%).

δH (400 MHz, CDCl$_3$) 8.72 (1H, d, J 1.6 Hz), 8.48 (1H, dd, J 5.2, 1.6 Hz), 7.82 (1H, br d, J 6.6 Hz), 7.40-7.36 (2H, m), 7.33-7.26 (3H, m), 7.17-7.13 (2H, m), 7.08 (1H, br s), 3.99-3.70 (3H, m, incl. 3.87 ppm, 1H, br dd, J 14.2, 11.0 Hz), 3.68-3.54 (1H, m), 3.50 (1H, dt, J 23.1, 11.5, 2.4 Hz), 2.95 (1H, dt, J 12.5, 2.6 Hz), 2.86 (1H, dd, J 14.0, 7.0 Hz), 2.74 (1H, dd, J 14.1, 5.4 Hz), 2.74-2.62 (1H, m), 1.44 (9H, s).

Mass spec: [MH]+381.

N-Boc-(R)-2-(3-vinylbenzyl)morpholine

Example 42 (0.51 g, 2.51 mmol) was dissolved in dichloromethane (10 mL) and cooled to 0° C. under an atmosphere of nitrogen gas. Di-tert-butyl-dicarbonate (0.6 g, 2.76 mmol) was then added dropwise over 5 minutes as a solution in dichloromethane (3 mL), and allowed to stir at room temperature for 72 hrs. The reaction was then concentrated in vacuo and the resiude purified by column chromatography (silica; 10-25% ethyl acetate: isohexane) to obtain the desired N-Boc-(R)-3-vinyl-benzylmorpholine, intermediate (b), N-Boc-(R)-2-(3-vinylbenzyl)morpholine as a colorless oil (0.6 g, 78% yield).

LC (50% to 80% gradient 210 nm XTERRA 2 ml/min) 99.7% @ 5.33 min.

Mass spec: [MH]$^+$ 304; [M−tBu+H]$^+$ 248.

Example 49

(R)-2-(3-(1-Hydroxyethyl)-4-methoxybenzyl)morpholine

Sodium borohydride (4 mg, 0.096 mmol) was added to a solution of example 56 (R)-2-(3-acetyl-4-methoxybenzyl) morpholine (20 mg, 0.08 mmol) in ethanol (10 mL). The mixture was stirred for 17 h, concentrated and the residue partitioned between ethyl acetate and water. The organic phase was separated, dried (Na$_2$SO$_4$) and concentrated affording the example 49 as a colorless solid (4.4 mg, 21.9%).

LC (50% to 80% gradient 220 nm XTERRA 2 ml/min) 87.1% @ 0.53 min.

Mass spec: [MH]+252.

Example 50

(R)-2-(7-bromo-5-(2,3-dihydrobenzofuryl) )morpholine (R)-1-chloro-3-(5-(2,3-dihydrobenzofuryl))-2-propanol was prepared using the same method as described for example 2, intermediate (d), but using 5-bromo-2,3-dihydrobenzofuran and (R)-epichlorohydrin. (R)-2-(5-(2,3-dihydrobenzofuryl))morpholine was prepared using the procedure as described for example 1, intermediate (d), but using (R)-1-chloro-3-(5-(2,3-dihydrobenzofuryl))-2-propanol. To a solution of (R)-2-(5-(2,3-dihydrobenzofuryl))morpholine (50 mg, 0.23 mmol) in methanol (5 mL) was added hydrogen chloride (4M in dioxane, 0.063 mL, 0.25 mmol). After 1 hour the solvents were evaporated and the residue diluted with N,N-dimethyl formamide (5 mL). N-bromosuccinimide (45 mg, 0.253 mmol) was added and the mixture stirred for 18 h. Purification using SCX-2 cartridge followed by preparative HPLC afforded example 50 as an off-white gum (2.6 mg, 3.8%).

LC (50% to 80% gradient 220 nm XTERRA 2 ml/min) 92.0% @ 0.93 min.

Mass spec: [MH]+298/300.

Example 51

(R)-2-(3,5-Dibromo-2-hydroxybenzyl)morpholine

Deprotection of example 1, intermediate (b), using hydrogen chloride (4M, in methanol), afforded the morpholine example 51 as a white solid (13 mg, 8%).

LC (50% to 80% gradient 220 nm XTERRA 2 ml/min) 99.7% @ 1.71 min.

Mass spec: found [M–H]$^-$ 348/350/352

Example 52

(R)-2-[3-Chloro-4-(tetrahydro-furan-2-ylmethoxy)-benzyl]-morpholine

Example 52 was prepared using the same procedure as described for example 7 starting from example 7, intermediate (a), N-BOC-(R)-2-(3-chloro-4-hydroxybenzyl)morpholine and tetrahydrofurfuryl alcohol. The resulting intermediate was deprotected with TFA as described for example 7 to yield the desired morpholine example 52 as a colorless oil (26 mg, 52% over 2 steps) after purification by HPLC.

LC (50% to 80% gradient 220 nm XTERRA 2 ml/min) 99.3% @ 1.05 min.

Mass spec: found [MH]$^+$ 312

Example 53

(R)-2-(3-Ethyl-4-methoxy-benzyl)-morpholine

Tetrakis(triphenylphosphine)palladium(0) (21 mg, 0.017 mmol) was added to a solution of N-Boc-(R)-2-(3-iodo-4-methoxybenzyl)morpholine, example 17, intermediate (b) (150 mg, 0.35 mmol), and diethylzinc (1M in hexanes, 0.69 mL, 0.693 mmol) in tetrahydrofuran (10 mL) and heated to reflux for 18 h. The cooled reaction mixture was filtered and the liquors partitioned between ethyl acetate and water. The organic phase was separated, dried (Na$_2$SO$_4$) and concentrated and the residue purified by preparative HPLC to give the N-Boc protected material that was deprotected using hydrogen chloride (dioxane-methanol) to affored example 53 as a colorless oil (13.4 mg, 16.5%).

LC (20% to 50% gradient 220 nm XTERRA 2 ml/min) 95.5% @ 4.43 min.

Mass spec: [MH]$^+$ 236.

Example 54

(R)-2-[3-(3,5-dimethyl-isoxazol-4-yl)-4-methoxy-benzyl]-morpholine

Tetrakis(triphenylphosphine)palladium(0) (19 mg, 0.016 mmol) was added to a solution of N-Boc-(R)-2-(3-iodo-4-methoxybenzyl)morpholine, example 17, intermediate (b) (140 mg, 0.32 mmol), potassium carbonate (133 mg, 0.96 mmol) and 3,5-dimethyl-isoxazol-4-yl boronic acid (68 mg, 0.48 mmol) in DME/water (13 mL, 12:1 ratio) and heated to 100° C. for 18 h. The cooled reaction mixture was filtered and the liquors partitioned between ethyl acetate and water. The organic phase was separated and dried (Na$_2$SO$_4$) and concentrated to give the crude product which was purified by silica gel chromatography (5% ethyl acetate:dichloromethane) affording the N-Boc protected material as a brown oil (58 mg, 45%). Deprotection using hydrogen chloride (4M in dioxane, 0.36 mL, 1.46 mmol) in methanol (10 mL) followed by purification using an SCX-2 cartridge eluting with methanol-ammonia afforded example 54 as a colorless gum (45 mg, 99%).

LC (20% to 50% gradient 220 nm XTERRA 2 ml/min) 97.8% @ 2.96 min.

Mass spec: [MH]$^+$ 303.

Example 55

1-(2-Methoxy-5-(R)-1-morpholin-2-ylmethyl-phenyl)-ethanone

Deprotection of N-Boc-(R)-2-(3-acetyl-4-methoxybenzyl)morpholine, example 17, intermediate (a), using hydrogen chloride (4M in dioxane, 1.6 mL, 6.35 mmol) in methanol (10 mL) followed by purification using an SCX-2 cartridge as described for example 2 afforded example 55 as a yellow oil (42 mg, 32%).

LC (20% to 50% gradient 220 nm XTERRA 2 ml/min) 98.7% @ 1.40 min.

Mass spec: [MH]+250.

Example 56

(R)-2-(3-Iodo-4-methoxy-benzyl)-morpholine

To a solution of N-Boc-(R)-2-(4-methoxy-benzyl)-morpholine, example 9, intermediate (a) (255 mg, 0.83 mmol), in methanol (10 mL) was added silver tetrafluoroborate (177 mg, 0.91 mmol) and iodine (231 mg, 0.91 mmol). The mixture was shaken for 17 h and partitioned between ethyl acetate and water. The organic phase was separated, dried and concentrated to give the crude product, which was purified using an SCX-2 cartridge affording example 56 as a colorless oil (45.9 mg, 13%).

LC (20% to 50% gradient 220 nm XTERRA 2 ml/min) 88.4% @ 4.51 min.

Mass spec: [MH]$^+$ 334.

Example 57

(R)-2-(5-Bromo-2,4-dimethoxy-benzyl)-morpholine (R)-1-Chloro-3-(2,4-dimethoxyphenyl)-2-propanol was prepared using the same procedure as described for example 2, intermediate (d), but from 2,4-dimethoxybromobenzene and (R)-epichlorohydrin.

(R)-1-chloro-3-(2,4-dimethoxyphenyl)-2-propanol was then exposed to the procedure as described for example 1, intermediate (d), to obtain the desired morpholine, as a colorless oil which was immediately N-Boc protected using Boc$_2$O. Purification by silica gel chromatography afforded N-Boc-(R)-2-(2,4-dimethoxy-benzyl)-morpholine.

N-bromosuccinimide (29 mg, 0.16 mmol) was added to a solution of N-Boc-(R)-2-(2,4-dimethoxy-benzyl)-morpholine (54 mg, 0.16 mmol) in acetonitrile (6.0 mL). The mixture was shaken for 66 h, concentrated and the residue partitioned between ethyl acetate and water. The organic phase was separated, dried and concentrated to give N-Boc-(R)-2-(5-bromo-2,4-dimethoxy-benzyl)-morpholine which was immediately deprotected using hydrogen chloride (4M in dioxane) in methanol affording example 57 as a brown oil (55 mg, 100%).

LC (20% to 50% gradient 220 nm XTERRA 2 ml/min) 96.5% @ 4.64 min.

Mass spec: [MH]$^+$ 316/318.

Example 58

(R)-2-(3-Chloro-4-propyloxy-benzyl)-morpholine

Example 58 was prepared using the same procedure as described for example 20, starting from N-BOC-(R)-2-(3-chloro-4-hydroxybenzyl)morpholine, example 7, intermediate (a), and 1-iodopropane. The resulting intermediate was deprotected with TFA as described for example 20 to yield the desired morpholine example 58 as a colorless oil (16 mg) after purification by HPLC.

LC (50% to 80% gradient 220 nm XTERRA 2 ml/min) 99.1% @ 1.63 min.

Mass spec: found [MH]$^+$ 270

Example 59

(R)-2-(3-Bromo-4-cyclopentyloxy-benzyl)-morpholine

Example 59 was prepared using the same procedure as described for example 4, starting from N-BOC-(R)-2-(3-bromo-4-hydroxybenzyl)morpholine, example 4, intermediate (a) and cyclopentylbromide. The resulting intermediate was deprotected with TFA as described for example 4 to yield the desired morpholine example 59 as a colorless oil (37 mg, 67% over 2 steps).

LC (50% to 80% gradient 220 nm XTERRA 2 ml/min) 99.4% @ 3.43 min.

Mass spec: found [MH]$^+$ 340/342.

Example 60

(R)-2-(5-Bromo-2-difluoromethoxy-benzyl)-morpholine

To a solution of sodium hydroxide (186 mg, 4.64 mmol) in water (1.0 mL) was added tetra n-butylammonium bromide (50 mg, 0.155 mmol) followed by N-Boc-(R)-2-(5-bromo-2-hydroxybenzyl)morpholine (576 mg, 1.55 mmol), example 1, intermediate (a) in dioxane (8.0 mL). The reaction mixture was cooled to 10° C. and chlorodifluoromethane gas passed into the reaction mixture whilst the vessel was stoppered. After 15 mins, the solution was warmed to 23° C. whilst continuing to pass the gas into the solution. After 30 mins, the gas flow was ceased and the reaction stirred for 17 hrs before concentration and partition of the residue between ethyl acetate and water. The crude product was purified by silica gel chromatography, eluting with 10% ethyl acetate/iso-hexane, affording N-Boc-(R)-2-(5-bromo-2-difluoromethoxy-benzyl)-morpholine as an oil (357 mg, 55%).

N-Boc-(R)-2-(5-bromo-2-difluoromethoxy-benzyl)-morpholine, was deprotected using hydrogen chloride (4M, in methanol) and isolated using SCX-2 columns as described for example 4 followed by treatment with fumaric acid in IPA-diethyl ether afforded the morpholine example 61 as the fumarate salt as a white solid (108 mg, 30%).

LC (50% to 80% gradient 220 nm XTERRA 2 ml/min) 99.2% @ 1.28 min.

Mass spec: found [MH]$^+$ 322/324.

Example 61

(R)-2-(3-Bromo-4-butoxy-benzyl)-morpholine

Example 61 was prepared using the same procedure as described for example 4, starting from N-BOC-(R)-2-(3-bromo-4-hydroxybenzyl)morpholine, example 4, intermediate (a), and 1-bromobutane. The resulting intermediate was deprotected with TFA as described for example 4 to yield the desired morpholine example 61 as a colorless oil (28 mg, 63% over 2 steps) after purification by HPLC.

LC (50% to 80% gradient 220 nm XTERRA 2 ml/min) 99.8% @ 3.83 min.

Mass spec: found [MH]$^+$ 328/330.

Example 62

(R)-2-(3-Bromo-4-isopropoxy-benzyl)-morpholine

Example 62 was prepared using the same procedure as described for example 4, starting from N-BOC-(R)-2-(3-bromo-4-hydroxybenzyl)morpholine, example 4, intermediate (a), and 2-bromopropane. The resulting intermediate was deprotected with TFA as described for example 4 to yield the desired morpholine example 62 as a colorless oil (22 mg, 52% over 2 steps) after purification by HPLC.

LC (50% to 80% gradient 220 nm XTERRA 2 ml/min) 99.9% @ 1.63 min.

Mass spec: found [MH]$^+$ 314/316.

Example 63

(R)-2-(3-Bromo-4-propoxy-benzyl)-morpholine

Example 63 was prepared using the same procedure as described for example 4, starting from N-BOC-(R)-2-(3-bromo-4-hydroxybenzyl)morpholine, example 4, intermediate (a), and 1-iodopropane. The resulting intermediate was deprotected with TFA as described for example 4 to yield the desired morpholine example 63 as a colorless oil (27 mg, 64% over 2 steps) after purification by HPLC.

LC (50% to 80% gradient 220 nm XTERRA 2 ml/min) 99.9% @ 1.99 min.

Mass spec: found [MH]$^+$ 314/316.

Example 64

(R)-2-(3-Chloro-4-methoxy-benzyl)-morpholine

Example 64 was prepared using the same procedure as described for example 27 but starting with N-benzyl-(R)-2-(3-Chloro-4-fluorobenzyl)-morpholine, example 27, intermediate (a), methanol and cesium carbonate. After deprotection with 1-chloro-ethyl-chloroformate, as described for example 27, yielded the desire morpholine example 64 as an off-white gum (16 mg).

δH (400MHz, CDCl$_3$) 7.22 (1H, d, J 2.6 Hz), 7.04 (1H, dd, J 8.3, 2.2 Hz), 6.84 (1H, d, J 8.7 Hz), 3.88 (4H, br s), 3.62-3.56 (2H, m), 2.89-2.81 (3H, m), 2.74 (1H, dd, J 14.1, 7.1 Hz), 2.57 (2H, dd, J 14.0, 6.1 Hz), 2.51-2.30 (1H, br s).

LC (10% IPA/hexane isocratic 220 nm ChiralPak AD 1 ml/min) 89.9% @ 11.04 min.

Example 65

(R)-2-(5-Chloro-2-fluoro-4-methoxy-benzyl)-morpholine (R)-1-chloro-3-(5-chloro-2-fluoro-4-methoxyphenyl)-2-propanol was prepared using the same procedure as described for example 2, intermediate (d) starting from 4-bromo-5-fluoro-2-chloroanisole and (R)-epichlorohydrin. The resulting (R)-1-chloro-3-(5-chloro-2-fluoro-4-methoxyphenyl)-2-propanol was then transformed into the desired (R)-2-(5-Chloro-2-fluoro-4-methoxy-benzyl)-morpholine, using the procedure as described for example 1, intermediate (d). The morpholine (0.6 mmol) was dissolved in diethyl ether (4 mL) and added to a solution of fumaric acid (70 mg, 0.61 mmol) in IPA (1 mL) at 40° C. and the resulting solution allowed to cool to room temperature. The precipitate was filtered and washed with diethyl ether (2 mL, ×2), to yield the desired morpholine example 65 as the fumarate salt as a white powder (202 mg).

LC (20% to 50% gradient 220 nm XTERRA 2 ml/min) 84.9% @ 3.98 min.

Mass spec: found [MH]$^+$ 260.

Example 66

(R)-2-(2,2-Difluoro-benzo [1,3]dioxol-4-ylmethyl)-morpholine (R)-1-chloro-3-(2,2-difluoro-benzo[1,3]dioxol-4-yl)-2-propanol was prepared using the same procedure as described for example 2, intermediate (d), but from 4-bromo-2,2-difluoro-benzo[1,3]dioxole and (R)-epichlorohydrin. Example 66 was prepared as described for example 1, intermediate (d), but using (R)-1-chloro-3-(2,2-Difluoro-benzo[1,3]dioxol-4-yl)-2-propanol, to obtain the desired morpholine example 66, as a colorless liquid, (0.214 g, 13.6%).

LC (50% to 80% gradient 220 nm XTERRA 2 ml/min) 90.7% @ 1.26 min.

Mass spec: [MH]$^+$ 258.

Example 67

(R)-2-(2-Fluoro-3-trifluoromethyl-benzyl)-morpholine (R)-1-chloro-3-(2-fluoro-3-trifluoromethylphenyl)-2-propanol was prepared using the same procedure as described for example 2, intermediate (d), starting from 3-bromo-2-fluorobenzotrifluoride and (R)-epichlorohydrin. The resultant (R)-1-chloro-3-(2-fluoro-3-trifluoromethylphenyl)-2-propanol was transformed using the procedure as described for example 1, intermediate (d), into the desired morpholine example 67 as a colorless oil (14 mg).

LC (50% to 80% gradient 220 nm XTERRA 2 ml/min) 91.7% @ 1.26 min.

Mass spec: found [MH]$^+$ 264.

Example 68

(R)-2-[3-(2-Pyridin-2-yl-ethyl)-benzyl]-morpholine

Example 69 was prepared using the procedure as described for example 31, but starting with N-Boc-(R)-2-(3-bromobenzyl)morpholine, example 31, intermediate (b), and 2-vinylpyridine. The resulting intermediate was deprotected with TFA as described for example 4 to yield the desired morpholine example 68 as a yellow oil (16 mg).

LC (50% to 80% gradient 220 nm XTERRA 2 ml/min) 96.4% @ 0.81 min.

Mass spec: found [MH]$^+$ 283.

Example 69

2-(3-Ethyl-benzyl)-morpholine

N-Boc-2-(3-hydroxy)benzylmorpholine, trifluoromethylsulfonate ester intermediate (a) (62 mg, 0.16 mmol) was dissolved in tetrahydrofuran (3 mL) and NMP (0.3 mL) under an atmosphere of nitrogen, at room temperature then iron (III) ac ethyl acetateetate (3 mg, 7.3 umol) was added in one portion to give an orange solution. To the reaction mixture was added ethylmagnesium chloride (2.0M solution in tetrahydrofuran, 0.11 mL, 0.22 mmol) dropwise over 2 minutes and the reaction stirred at room temperature for 30 minutes. Then more iron (III) ac ethyl acetateetate (6 mg, 14.6 umol) was added in one portion followed by ethylmagnesium chloride (2.0M solution in tetrahydrofuran, 0.24 mL, 0.48 mmol) dropwise over 3 minutes. After 30 minutes citric acid (10% w/w aqueous solution, 10 mL) and ethyl acetate (10 mL) was added and the mixture stirred vigorously for 5 minutes and left to stand for 18 hrs. The layers were separated and the aqueous layer extracted with ethyl acetate (10 mL). Combined organic layers were washed with water (10 mL), then brine (10 mL), dried (MgSO$_4$), filtered and concentrated in vacuo. The residue was dissolved in dichloromethane (2.5 mL) and treated with TFA (1 mL) and stirred at room temperature for 3 hrs. The reaction was then poured through an SCX-2 column and washed with dichloromethane. The column was then washed with ammonia (2N, methanol) and the ammonia washes concentrated in vacuo. The residue was purified by preparative HPLC to yield the desired morpholine example 69 as an off-white solid (6 mg).

LC (20% to 50% gradient 220 nm XTERRA 2 ml/min) 99.6% @ 4.19 min.

Mass spec: found [MH]$^+$ 206.

Intermediates

N-Boc-2-(3-hydroxy)benzylmorpholine, trifluoromethylsulfonate ester

N-Boc-2-(3-hydroxy)benzylmorpholine was prepared using the same procedure as described for N-BOC (R)-2-(2-hydroxybenzyl)morpholine, example 1, intermediate (c), but starting from 3-bromo-anisole. N-Boc-2-(3-hydroxy)benzylmorpholine (1.4 mmol crude) was dissolved in dichloromethane (5 mL) with diisopropylethylamine (0.36 g, 2.8 mmol) and N-phenyltrifluoromethylsulfonimide (0.5 g, 1.4 mmol) added in one portion. The reaction mixture was stirred at room temperature for 72 hrs, then poured into water (20 mL) and extracted with dichloromethane (20 mL×2). The combined organic layers were washed with brine (10 mL), dried (MgSO$_4$), filtered and concentrated in vacuo to yield the desired intermediate (a) N-Boc-2-(3-hydroxy)benzylmorpholine, trifluoromethylsulfonate ester.

δH (400MHz, CDCl$_3$) 7.36 (1H, t, J 7.7 Hz), 7.26-7.23 (1H, m), 7.17 (1H, br s), 7.14 (1H, dd, J 7.7, 2.3 Hz), 3.90-3.74 (3H, m), 3.60-3.53 (1H, m), 3.46 (1H, dt, J 11.7, 2.8 Hz), 2.93 (1H, br t, J 12.6 Hz), 2.84 (1H, dd, J 14.2, 7.8 Hz), 2.74 (1H, dd, J 14.0, 5.1 Hz), 1.45 (9H, s).

Mass spec: found [M+Na]$^+$ 448; [M−tBuOCO+H]+326.

Example 70

2-(2-Fluoro-3-methyl-benzyl)-morpholine

To a solution of intermediate (a), N-Benzyl-2-(2-fluoro-3-methyl-benzyl)-morpholine (190 mg, 0.633 mmol) in dichloroethane (10 mL) was added 1-chloroethyl chloroformate (0.14 mL, 1.27 mmol). The mixture was heated to 110° C. for 1 h, concentrated, diluted with methanol and heated to reflux for 2 h. The solution was concentrated and the residue purified by silica gel chromatography, eluting with dichloromethane -methanol-ammonium hydroxide (94/4/2) affording example 70 as a colorless oil (60.0 mg, 45%).

LC (20% to 50% gradient 220 nm XTERRA 2 ml/min) 98.1% @ 3.21 min.

Mass spec: [MH]$^+$ 211.

Intermediates

N-Benzyl-2-(2-fluoro-3-methyl-benzyl)-morpholine

To a solution of intermediate (b), N-benzyl-2-(2-Fluoro-3-methyl-benzyl)-morpholin-3-one (275 mg, 0.876 mmol) in tetrahydrofuran (10 mL) at 0° C. was added BH$_3$ (1M in tetrahydrofuran, 2.63 mL, 2.63 mmol). The mixture was stirred at 23° C. for 1 h then heated to reflux for 18 h, cooled to 23° C. and stirred vigorously with Rochelle's salt solution (15 mL) for 1.5 h. Ethyl acetate (30 mL) was added and stirring continued for 1.5 h. The organic phase was separated, dried (Na$_2$SO$_4$) and concentrated affording intermediate (a), N-benzyl-2-(2-fluoro-3-methyl-benzyl)-morpholine, as a pale yellow oil (190 mg, 73%).

N-Benzyl-2-(2-fluoro-3-methyl-benzyl)-morpholin-3-one

To a solution of di-iso-propylamine (0.76 mL, 5.42 mmol) in tetrahydrofuran (10 mL) at 0° C. was added n-butyl-lithium (2.5M in hexanes, 2.17 mL, 5.42 mmol). The mixture was stirred for 20 mins before cooling to −78° C. and dropwise addition of 4-benzylmorpholine-3-one (0.941 g, 4.92 mmol) in tetrahydrofuran (5 mL). The solution was stirred for 45 mins before addition of 2-fluoro-3-methylbenzyl bromide (1.0 g, 4.92 mmol) in tetrahydrofuran (5 mL). The solution was stirred at −78° C. for 1.5 h then warmed to 0° C. and stirred for a further 1 h before warming to 23° C. Saturated ammonium chloride solution (5 mL) was added and the mixture extracted with ethyl acetate (20 mL). The organic phase was separated, dried (Na$_2$SO$_4$) and concentrated and the residue purified by silica gel chromatography, eluting with iso-hexane/ethyl acetate (4:1), affording intermediate (b), N-benzyl-2-(2-fluoro-3-methyl-benzyl)-morpholin-3-one as a pale yellow oil (275 mg, 18%).

Example 71

2-(4-fluoro-3-methylbenzyl)-morpholine

Example 71 was prepared as described for example 27, but using N-benzyl-2-(4-fluoro-3-methylbenzyl)-morpholine, intermediate (a) and 1-chloroethyl chloroformate. Example 71 was isolated as a colorless oil (13.7 mg).

LC (20% to 50% gradient 220 nm XTERRA 2 ml/min) 92.5% @ 4.49 min.

Mass spec: [MH]$^+$ 210.

Intermediates

N-Benzyl-2-(4-fluoro-3-methylbenzyl)-morpholine

N-Benzyl-2-(4-fluoro-3-methylbenzyl)-morpholine was prepared as described for example 70, intermediate (a), but using N-benzyl-2-(4-fluoro-3-methylbenzyl)-morpholin-3-one and borane and was isolated as a pale yellow oil.

N-Benzyl-2-(4-fluoro-3-methylbenzyl)-morpholin-3-one

N-Benzyl-2-(4-fluoro-3-methylbenzyl)-morpholin-3-one was prepared as described for example 70, intermediate (b), but using 4-benzylmorpholine-3-one and 4-fluoro-3-methylbenzyl bromide and was isolated as a pale yellow oil.

Example 72

2-(3-Bromo-4-methoxy-benzyl)-morpholine

N-Boc-2-(4-methoxybenzyl)morpholine was prepared using the same procedure as described for example 9, intermediate (a), but starting with racemic epichlorohydrin. N-Boc-2-(4-methoxybenzyl) (0.16 mmol) was dissolved in dichloromethane (1.5 mmol) and N-bromosuccinimide (28 mg, 0.16 mmol) added. The reaction was shaken for 18 hrs at room temperature and then further N-bromosuccinimide (11 mg, 0.06 mmol) added. The reaction was shaken for a further 2 hrs, Na$_2$S$_2$O$_3$ (10% w/v aqueous solution, 1 mL) added and the mixture shaken for 40 minutes. The mixture was poured on to an HMN column (25 g) and washed with dichloromethane (10 mL) and the liquors concentrated in vacuo. The residue was dissolved in dichloromethane (1.5 mL), treated with TFA (1 mL) and shaken for 90 minutes at room temperature. The reaction mixture was added directly to an SCX-2 column (5 g) and washed with dichloromethane (2 mL×2) and methanol (2 mL). The SCX-2 column was then washed with ammonia (2N in methanol, 3×2 mL and 2×2.5 mL). Combined ammonia washes were concentrated in vacuo. The residue was dissolved in IPA (2 mL) and diethyl ether (2 mL) and treated with MP-carbonate (3.1 mmol/g, 300 mg) and shaken for 30 minutes. The suspensions were filtered and the concentrated in vacuo to yield the desired 2-(3-Bromo-4-methoxy-benzyl)-morpholine example 72, as a beige gum (18 mg).

LC (50% to 80% gradient 220 nm XTERRA 2 ml/min) 89.2% @ 3.6 min.

Mass spec: found [MH]$^+$ 286/288.

Example 73

2-(3-Bromobenzyl)-morpholine

Example 73 was prepared as described for example 27, but using N-benzyl-2-(3-bromobenzyl)-morpholine intermediate (a) and 1-chloroethyl chloroformate and was isolated as a colorless oil (13.7 mg).

LC (20% to 50% gradient 220 nm XTERRA 2 ml/min) 92.5% @ 4.49 min.

Mass spec: [MH]$^+$ 257.

Intermediates

N-Benzyl-2-(3-bromobenzyl)-morpholine

N-Benzyl-2-(3-bromobenzyl)-morpholine was prepared as described for example 71, intermediate (a), but using N-benzyl-2-(3-bromobenzyl)-morpholin-3-one and borane and was isolated as a pale yellow oil.

N-Benzyl-2-(3-bromobenzyl)-morpholin-3-one

N-Benzyl-2-(3-bromobenzyl)-morpholin-3-one was prepared as described for example 71, intermediate (b), but using 4-benzylmorpholine-3-one and 3-bromobenzyl bromide and was isolated as a pale yellow oil.

Example 74

(S)-2-(3-Trifluoromethyl-benzyl)-morpholine

3-Bromobenzotrifluoride (1.46 g, 6.5 mmol) was added over 5-10 minutes as a solution in diethyl ether (5 mL) dropwise to magnesium turnings (0.145 g, 5.9 mmol) in diethyl ether (2 mL), under an atmosphere of nitrogen with iodine (1 crystal) to initial reaction. The dropping funnel was washed with diethyl ether (3 mL total). The reaction was allowed to reach reflux during the addition of the bromide and then allowed to cool to room temperature and stirred for a further 1 hr. Copper (I) iodide (103 mg, 0.54 mmol) was added in one portion and the reaction mixture cooled to 0° C. over 10 minutes. (S)-epichlorohydrin (0.5 g, 5.4 mmol)

was added as a solution in diethyl ether (3 mL) over 10 minutes and the reaction allowed to warm to room temperature. After 2 hrs methanol (10 mL) was added and the resulting suspension stirred vigorously. Then sodium hydroxide (1.73 g, 43 mmol) was added as a solution in water (2.7 mL), followed by more methanol (4 mL) to try to loosen the precipitate formed, and 2-aminoethane hydrogen sulfate (3.05 g, 21.6 mmol) was added. The mixture was warmed to 42° C. (bath temperature) for 2 hrs, then toluene (10 mL) and sodium hydroxide (1.35 g, crushed, 33.8 mmol) added and the resulting green paste heated at 70° C. (bath temperature) for 18 hrs. The reaction was allowed to cool to room temperature, poured into water (40 mL) and extracted with toluene (20 mL) and ethyl acetate (20 mL×2). The combined organic layers were washed with brine (10 mL), dried ($MgSO_4$), filtered and concentrated in vacuo. The residue was purified by column chromatography (silica; triethylamine/ethanol/ethyl acetate, 1/20/79 ratio) to yield the desired morpholine. The morpholine (0.27 g) was dissolved in diethyl ether (3 mL total) and added to a solution of fumaric acid (0.119 g, 1.03 mmol) in IPA (2 mL) at 40° C. and the solution allowed to cool to room temperature. The precipitate was filtered out and washed with diethyl ether and dried in vacuo to yield the desired morpholine 74 as a fumarate salt as a white powder (0.284 g).

LC (20% to 50% gradient 220 nm XTERRA 2 ml/min) 98.9% @ 5.42 min.

Mass spec: found $[MH]^+$ 246.

Example 75

2-(2-Difluoromethoxy-benzyl)-morpholine

Example 75 was prepared as described for example 27, but using N-benzyl-2-(2-difluoromethoxy-benzyl)-morpholine, intermediate (a) and 1-chloroethyl chloroformate and example 75 was isolated as a colorless oil (7.9 mg).

LC (20% to 50% gradient 220 nm XTERRA 2 ml/min) 96.0% @ 2.62 min.

Mass spec: $[MH]^+$ 245.

Intermediates

N-Benzyl-2-(2-difluoromethoxy-benzyl)-morpholine

N-Benzyl-2-(2-difluoromethoxy-benzyl)-morpholine was prepared as described for example 70, intermediate (a), but using N-benzyl-2-(2-difluoromethoxy-benzyl)-morpholin-3-one and borane and was isolated as a pale yellow oil.

N-Benzyl-2-(2-difluoromethoxy-benzyl)-morpholin-3-one

N-Benzyl-2-(2-difluoromethoxy-benzyl)-morpholin-3-one was prepared as described for example 70, intermediate (b), but using 4-benzylmorpholine-3-one and 2-difluoromethoxybenzyl bromide and was isolated as a pale yellow oil.

Example 76

2-(3-Methyl-benzyl)-morpholine

Example 76 was prepared as described for example 27, but using N-benzyl-2-(3-methylbenzyl)-morpholine, intermediate (a) and 1-chloroethyl chloroformate and was isolated as a colorless oil (38.6 mg).

LC (20% to 50% gradient 220 nm XTERRA 2 ml/min) 96.3% @ 2.48 min.

Mass spec: $[MH]^+$ 193.

Intermediates

N-Benzyl-2-(3-methylbenzyl)-morpholine

N-Benzyl-2-(3-methylbenzyl)-morpholine was prepared as described for example 70, intermediate (a), but using N-benzyl-2-(3-methylbenzyl)-morpholin-3-one and borane and was isolated as a pale yellow oil.

N-Benzyl-2-(3-methylbenzyl)-morpholin-3-one

N-Benzyl-2-(3-methylbenzyl)-morpholin-3-one was prepared as described for example 70, intermediate (b), but using 4-benzylmorpholine-3-one and 3-methylbenzyl bromide and was isolated as a pale yellow oil.

Example 77

2-(3-Trifluoromethyl-benzyl)-morpholine

Example 77 could be prepared using the procedure as described for example 75 but starting from 3-bromo-benzotrifluoride and epichlorohydrin to yield the desired morpholine example 78 as a white powder (0.47 g) as the fumarate salt.

LC (20% to 50% gradient 220 nm XTERRA 2 ml/min) 97.3% @ 4.99 min.

Mass spec: found $[MH]^+$ 246.

Example 78

(R)-4-(2,5-Difluoro-4-(R)-1-morpholin-2-ylmethyl-phenoxy)-1,1,1-trifluoro-butan-2-ol To a solution of 65 mg of (R)-2-[2,5-difluoro-4-(4,4,4-trifluoro-3-(R)-hydroxy-butoxy)-benzyl]-morpholine-4-carboxylic acid tert-butyl ester in dichloromethane (2 ml) was added trifluoroacetic acid (0.5 mL) and the reaction mixture was stirred for 1 hour at room temperature. The mixture was than poured into sodium hydroxide solution (8 mL, 1N) and partitioned into dichloromethane. Organic phases were pooled, dried with $Na_2SO_4$ and concentrated in vacuo to give 51 mg of the title compound.

MS (ISP): 356.1 ($M+H^+$)

Intermediates a) (R)-2-[2,5-Difluoro-4-(4,4,4-trifluoro-3-(R)-hydroxy-butoxy)-benzyl]-morpholine-4-carboxylic acid tert-butyl ester To a solution of 50 mg of (R)-2-(2,5-difluoro-4-hydroxy-benzyl)-morpholine-4-carboxylic acid tert-butyl ester in 2-butanone (3 ml) was added potassium carbonate (42 mg) and (R)-4,4,4-trifluoro-1,3-butanediol-1-(4-methylbenzene-sulfonate) (50 mg). This reaction mixture was boiled with stirring for 4 hours. After cooling the mixture partitioned between ethyl acetate and ice water. Organic phases were pooled, dried with $MgSO_4$ and concentrated in vacuo. The residue was then purified by column chromatography (heptane ethyl acetate/ silica gel) to give 65 mg of the title compound.

MS (ISN): 514.3 ($M+OAc^-$)

b) (R)-2-(2,5-Difluoro-4-hydroxy-benzyl)-morpholine-4-carboxylic acid tert-butyl ester A suspension of palladium on carbon (10%, 0.47 g) in a solution of 4.7 g of (S)-2-[(4-benzyloxy-2,5-difluoro-phenyl)-bromo-methyl]-morpholine-4-carboxylic acid tert-butyl ester in ethanol (400 ml) was hydrogenated at room temperature and normal pressure till the theoretical amount of hydrogen had been consumed. Solids were removed by filtration and the filtrate was concentrated in vacuo. The residue was partitioned with ethyl acetate and saturated sodium bicarbonate solution. Organic phases were pooled, washed with brine and dried with $Na_2SO_4$ before being concentrated in vacuo. The residue was then purified by column chromatography (dichloromethane-diethyl ether (19:1)/silica gel) to give 0.5 g of the title compound.

MS (ISN): 328.4 (M–H$^-$)

c) (S)-2-[(4-Benzyloxy-2,5-difluoro-phenyl)-bromo-methyl]-morpholine-4-carboxylic acid tert-butyl ester To a solution of 7.5 g of ((S)-2-[(4-benzyloxy-2,5-difluoro-phenyl)-hydroxy-methyl]-morpholine-4-carboxylic acid tert-butyl ester in dichloromethane (90 ml) was added with cooling (0-5° C.) tetrabromomethane (12.5 g) and afterwards triphenylphosphine (13.5 g) in small portions. Stirring continued for 1 hour at room temperature before the mixture was added dropwise to diethyl ether (600 mL). Solids were removed by filtration and the filtrate was concentrated in vacuo. The residue was then purified by column chromatography (heptane-ethyl acetate (3:1)/silica gel) to give 5.6 g of the title compound.

MS (EI) 498.2, 500.2 (M)

d) (S)-2-[(4-Benzyloxy-2,5-difluoro-phenyl)-hydroxy-methyl]-morpholine-4-carboxylic acid tert-butyl ester To a solution of 7.5 g of (S)-2-(4-benzyloxy-2,5-difluoro-benzoyl)-morpholine-4-carboxylic acid tert-butyl ester in methanol (90 ml) was added with cooling (0-5° C.) sodium borohydride (660 mg) in small portions. Stirring continued for 15 minutes with cooling before sodium bicarbonate (150 mL, saturated) was added. Organic material was partitioned into ethyl acetate (3×), organic phases were pooled, washed with brine and dried with $Na_2SO_4$ before being concentrated in vacuo to give 7.5 g of the title compound.

MS (ISP): 436.5 (M+H$^+$)

e) (S)-2-(4-Benzyloxy-2,5-difluoro-benzoyl)-morpholine-4-carboxylic acid tert-butyl ester To a solution of 33 mL of isopropylmagnesium bromide (1M in tetrahydrofuran) in tetrahydrofuran (120 mL) was added with cooling (max+3° C.) n-butyllithium (41 mL, 1.6M in hexane). The mixture was cooled to −78° C., 1-benzyloxy-4-bromo-2,5-difluoro-benzene (8.2 g, 27 mmol) was added and stirred for 1.5 hours at this temperature. (S)-2-(Methoxy-methyl-carbamoyl)-morpholine-4-carboxylic acid tert-butyl ester (7.5 g, 27 mmol) was added dropwise within 10 min at −75° C. Stirring at −78° C. continued for 1 h and the reaction mixture was than poured into water (600 mL). Organic material was partitioned into ethyl acetate (3×), organic phases were pooled, washed with brine and dried with $MgSO_4$ before being concentrated in vacuo. The residue was then purified by column chromatography (heptane-ethyl acetate (2:1)/silica gel) to give 7.5 g of the title compound.

MS (ISP) 434.5 (M+H$^+$)

f) 1-Benzyloxy-4-bromo-2,5-difluoro-benzene

To a solution of 21 g of 1-hydroxy-4-bromo-2,5-difluoro-benzene in 2-butanone (300 ml) and was added potassium carbonate (20.8 g) and benzylbromide (24 mL). The reaction mixture was boiled while stirring for 1.5 hours. After cooling to room temperature the mixture was partitioned between ethyl acetate and water. Organic phases were pooled, dried with $MgSO_4$ and concentrated in vacuo. The residue was then purified by column chromatography (heptane/silica gel) to give 25.3 g of the title compound.

MS (EI): 300.0 (M)

Example 79

(R)-2-[2,5-Difluoro-4-(5-methyl-isoxazol-3-yl-methoxy)-benzyl]-morpholine

The title compound was synthesized in analogy to Example 78, intermediate (a), using 3-(bromomethyl)-5-methylisoxazol and (R)-2-(2,5-difluoro-4-hydroxy-benzyl)-morpholine-4-carboxylic acid tert-butyl ester as starting materials.

MS (ISP): 325.1 (M+H$^+$)

Example 80

(R)-2-(2-Chloro-4'-methanesulfonyl-biphenyl-4-ylmethyl)-morpholine

The title compound was synthesized in analogy to example 83 from (R)-2-(2-chloro-4'-methanesulfonyl-biphenyl-4-ylmethyl)-morpholine-4-carboxylic acid tert-butyl ester to give the title compound as a light yellow foam (82%).

MS (ISP): 366.1 (M+H$^+$)

Intermediates a) (R)-2-(2-Chloro-4'-methanesulfonyl-biphenyl-4-ylmethyl)-morpholine-4-carboxylic acid tert-butyl ester To the solution of 0.20 g (0.43 mmol) (R)-2-(3-chloro-4-trifluoromethanesulfonyloxy-benzyl)-morpholine-4-carboxylic acid tert-butyl ester in 8 mL 1,2-dimethoxyethane 50 mg (43 μmol) tetrakis(triphenylphosphine)palladium(0) were added. After 30 min. 0.31 g (1.56 mmol) 4-methanesulphonyl)benzeneboronic acid and 0.11 g (1.08 mmol) sodium bicarbonate dissolved in 4 mL water were added successively and the reaction stirred for 1 h under reflux. After cooling down to room temperature the reaction mixture was diluted with ethyl acetate and extracted with 10% aqueous sodium bicarbonate solution and brine. The organic phase was dried over magnesium sulfate, filtered and evaporated. The residue was purified by column chromatography on silica gel using ethyl acetate as eluant to give the compound as colorless oil (98%).

MS (ISP): 483.4 (M+NH$_4^+$)

b) (R)-2-(3-Chloro-4-trifluoromethanesulfonyloxy-benzyl)-morpholine-4-carboxylic acid tert-butyl ester To the solution of 1.80 g (5.5 mmol) (R)-2-(3-chloro-4-hydroxy-benzyl)-morpholine-4-carboxylic acid tert-butyl ester (example 7, intermediate (a)) in 25 mL dichloromethane 1.53 mL (11.0 mmol) triethylamine were added. After cooling down to 0° C. 1.0 mL (6.0 mmol) trifluoromethanesulfonic anhydride were added and the cooling bath was removed. After 1 h stirring at room temperature the reaction mixture was extracted with 10% aqueous sodium bicarbonate solution and brine and the organic layer was dried over magnesium sulfate, filtered and evaporated. The residue was purified by column chromatography on silica gel using n-hexane:ethyl acetate (2:1 v/v) as eluant to give the compound in form of a light yellow oil (98%).

MS (ISP): 477.2 (M+NH$_4^+$)

Example 81

(R)-2-(3-Chloro-4-methylsulfanyl-benzyl)-morpholine

The solution of 0.4 g (1.6 mmol) (R)-1-chloro-3-(3-chloro-4-methylsulfanyl-phenyl)-propan-2-ol in 1.4 mL methanol was treated with a solution of 0.39 g (1.0 mmol)

sodium hydroxide in 0.7 mL water and 0.92 g (6.5 mmol) 2-aminoethyl hydrogen sulfate. The reaction was warmed to 45° C. and stirred for 2.5 h. After the addition of 0.42 g (10.5 mmol) solid sodium hydroxide and 7 mL toluene the reaction temperature was raised to 65° C. After 4 h the reaction mixture was poured on water and extracted three times with ethyl acetate. The combined organic layers were washed with brine, dried over magnesium sulfate, filtered and evaporated. The residue was chromatographed using MPLC and dichloromethane: methanol: ammonia (9:1:0.1 v/v) as eluant to give the compound as a light brown oil (38%).

MS (ISP): 258.1 (M+H$^+$)

Intermediates (R)-1-Chloro-3-(3-chloro-4-methylsulfanyl-phenyl)-propan-2-ol

The solution of 1.1 g (4.6 mmol) 4-bromo-2-chloro-1-methylsulfanyl-benzene (e.g. Joshi, R. S et. al.; J. Karnatak University (1959), 4, 38-42) in 40 mL diethyl ether was cooled down to −115° C. Then, 3.0 mL tert-butyllithium (4.5 mmol; 1.5M solution in n-pentane) was added dropwise and after stirring for 50 min. at −100° C. 0.54 mL (6.9 mmol) (R)-(−)-epichlorohydrin was added. After 45 min. the reaction was allowed to warm to 0° C. and after another 1.5 h was quenched with water and extracted three times with ethyl acetate. The combined organic layers were washed with brine, dried over magnesium sulfate, filtered and evaporated. The residue was chromatographed using MPLC and tert-butyl methyl ether: n-heptane (1:2 v/v) as eluant to give the compound as a colorless oil (35%).

MS (EI): 250.1 (M)

Example 82

(R)-2-(3-Cyclopropyl-4-methoxy-benzyl)-morpholine

The solution of 0.98 mL (1.1 mmol; 1.1M solution in toluene) diethyl zinc in 2 mL dichloromethane was cooled down to 0° C. Then 0.8 mL trifluoroacetic acid in 2 mL dichloromethane and after 25 min. a solution of 0.29 g diiodomethane in 2 mL dichloromethane was added. After another 20 min. 0.18 g (0.54 mmol) (R)-2-(4-methoxy-3-vinyl-benzyl)-morpholine-4-carboxylic acid tert-butyl ester dissolved in 2 mL dichloromethane was added. The ice bath was removed and after 45 min. stirring at room temperature the reaction mixture was poured on 1M hydrochloric acid and extracted three times with dichloromethane. The combined organic layers were washed with brine, dried over magnesium sulfate, filtered and evaporated. The residue was chromatographed using MPLC and dichloromethane:methanol:ammonia (9:1:0.1 v/v) as eluant to give the compound as a light brown oil (26%).

MS (ISP): 248.1 (M+H$^+$)

Intermediates a) (R)-2-(4-Methoxy-3-vinyl-benzyl)-morpholine-4-carboxylic acid tert-butyl ester To the solution of 0.5 g (1.3 mmol) (R)-2-(3-bromo-4-methoxy-benzyl)-morpholine-4-carboxylic acid tert-butyl ester (see Example 9) in 15 mL 1,2-dimethoxyethane 45 mg (39 µmol) tetrakis(triphenylphosphine)palladium(0) and 0.17 g (3.9 mmol) lithium chloride were added. After the addition of 0.45 mL tributyl(vinyl)tin the reaction was stirred under reflux for 23 h. After cooling down to room temperature the reaction suspension was poured on 1N aqueous sodium hydroxide solution and was extracted three times with ethyl acetate. The combined organic layers were washed with brine, dried over magnesium sulfate, filtered and evaporated. The residue was chromatographed using MPLC and tert-butyl methyl ether: n-heptane (1:1 v/v) as eluant to give the compound as a colorless oil (83%).

MS (ISP): 351.4 (M+NH$_4^+$)

Example 83

(R)-2-{3-Chloro-4-[5-(4-methoxy-phenyl)-[1,2,4]oxadiazol-3-ylmethoxy]-benzyl}-morpholine The solution of 0.30 g (0.6 mmol) (R)-2-{3-chloro-4-[5-(4-methoxy-phenyl)-[1,2,4]oxadiazol-3-ylmethoxy]-benzyl}-morpholine-4-carboxylic acid tert-butyl ester in 3 mL dichloromethane was cooled to 0° C. and treated with 1.5 mL (19.6 mmol) trifluoroacetic acid. The cooling bath was removed and the solution stirred at room temperature for 1 h. The volatile components were evaporated and the residue dissolved in dichloromethane and extracted with 1N aqueous sodium hydroxide solution. The organic layer was washed with brine, dried over magnesium sulfate, evaporated and dried under high vacuum to give 0.23 g (95%) of the product as colorless oil.

MS (ISP): 416.3 (M+H$^+$)

Intermediates a) (R)-2-{3-chloro-4-[5-(4-methoxy-phenyl)-[1,2,4]oxadiazol-3-ylmethoxy]-benzyl}-morpholine-4-carboxylic acid tert-butyl ester To the solution of 0.20 g (0.6 mmol) (R)-2-(3-chloro-4-hydroxy-benzyl)-morpholine-4-carboxylic acid tert-butyl ester (example 7, intermediate (a)) in 2 mL N,N-dimethylformamide 29 mg (0.66 mmol) sodium hydride (55% dispersion in mineral oil) were added. After 30 min. 0.27 g (1.2 mmol) 3-(chlormethyl)-5-(4-methoxyphenyl)-1,2,4-oxadiazole were added. After 2 h the reaction mixture was extracted with 10% aqueous sodium bicarbonate solution and brine, dried over magnesium sulfate and evaporated. The remaining oil was chromatographed on silica gel with n-hexane:ethyl acetate (2:1 v/v) as eluant to give 0.30 g (95%) of the product as a colorless oil.

MS (ISP): 516.4 (M+H$^+$)

Example 84

(R)-2-[3-Chloro-4-(5-methyl-2-phenyl-oxazol-4-ylmethoxy)-benzyl]-morpholine

The title compound was synthesized in analogy to example 83 from (R)-2-[3-chloro-4-(5-methyl-2-phenyl-oxazol-4-ylmethoxy)-benzyl]-morpholine-4-carboxylic acid tert-butyl ester as starting material to give the compound as a light yellow solid (91%).

MS (ISP): 399.4 (M+H$^+$)

Intermediates (R)-2-[3-Chloro-4-(5-methyl-2-phenyl-oxazol-4-ylmethoxy)-benzyl]-morpholine-4-carboxylic acid tert-butyl ester The title compound was synthesized in analogy to example 83, intermediate, from (R)-2-(3-chloro-4-hydroxy-benzyl)-morpholine-4-carboxylic acid tert-butyl ester (example 7, intermediate (a)) and 4-chloromethyl-5-methyl-2-phenyl-oxazole as starting materials to give the compound as a colorless oil (94%).

MS (ISP): 499.4 (M+H$^+$)

Example 85

(R)-2-[3-Chloro-4-(5-phenyl-[1,2,4]oxadiazol-3-ylmethoxy)-benzyl]-morpholine

The title compound was synthesized in analogy to example 83 from (R)-2-[3-chloro-4-(5-phenyl-[1,2,4]oxadiazol-3-ylmethoxy)-benzyl]-morpholine-4-carboxylic acid tert-butyl ester to give the title compound as a light yellow solid (41%).
MS (ISP): 386.3 (M+H$^+$)

Intermediates (R)-2-[3-Chloro-4-(5-phenyl-[1,2,4]oxadiazol-3-ylmethoxy)-benzyl]-morpholine-4-carboxylic acid tert-butyl ester The title compound was synthesized in analogy to example 83, intermediate, from (R)-2-(3-chloro-4-hydroxybenzyl)-morpholine-4-carboxylic acid tert-butyl ester (example 7, intermediate (a)) and 3-(chloromethyl)-5-phenyl-1,2,4-oxadiazole as starting materials to give the compound as a colorless oil (80%).
MS (ISP): 486.5 (M+H$^+$)

Example 86

(R)-2-{3-Chloro-4-[5-(4-trifluoromethyl-phenyl)-[1,2,4]oxadiazol-3-ylmethoxy]-benzyl}-morpholine The title compound was synthesized in analogy to example 83 from (R)-2-{3-chloro-4-[5-(4-trifluoromethyl-phenyl)-[1,2,4]oxadiazol-3-ylmethoxy]-benzyl}-morpholine-4-carboxylic acid tert-butyl ester to give the title compound as light yellow oil (58%).
MS (ISP): 454.4 (M+H$^+$)

Intermediates (R)-2-{3-Chloro-4-[5-(4-trifluoromethyl-phenyl)-[1,2,4]oxadiazol-3-ylmethoxy]-benzyl}-morpholine-4-carboxylic acid tert-butyl ester The title compound was synthesized in analogy to example 83, intermediate, from (R)-2-(3-chloro-4-hydroxybenzyl)-morpholine-4-carboxylic acid tert-butyl ester (example 7, intermediate (a)) and 3-(chloromethyl)-5-[4-(trifluoromethyl)phenyl]-1,2,4-oxadiazole as starting materials to give the compound as a colorless oil (95%).
MS (ISP): 554.3 (M+H$^+$); 498.3 ((M+H$^+$)—C$_4$H$_8$)

Example 87

(R)-2-{3-Chloro-4-[2-(4-chloro-phenyl)-thiazol-4-ylmethoxy]-benzyl}-morpholine

The title compound was synthesized in analogy to example 83 from (R)-2-{3-chloro-4-[2-(4-chloro-phenyl)-thiazol-4-ylmethoxy]-benzyl}-morpholine-4-carboxylic acid tert-butyl ester to give the title compound as a light yellow solid (80%).
MS (ISP): 435.3 (M+H$^+$)

Intermediates (R)-2-{3-chloro-4-[2-(4-chloro-phenyl)-thiazol-4-ylmethoxy]-benzyl}-morpholine-4-carboxylic acid tert-butyl ester The title compound was synthesized in analogy to example 84 intermediate, from (R)-2-(3-chloro-4-hydroxybenzyl)-morpholine-4-carboxylic acid tert-butyl ester (example 7, intermediate (a)) and 4-(chloromethyl)-2-(4-chlorophenyl)-1,3-thiazole as starting materials to give the compound as a light yellow oil (68%).
MS (ISP): 535.5 (M+H$^+$)

Example 88

(R)-2-[3-Chloro-4-(5-trifluoromethyl-furan-2-ylmethoxy)-benzyl]-morpholine

The title compound was synthesized in analogy to example 83 from (R)-2-[3-chloro-4-(5-trifluoromethyl-furan-2-ylmethoxy)-benzyl]-morpholine-4-carboxylic acid tert-butyl ester to give the title compound as light yellow foam (98%).
MS (ISP): 376.3 (M+H$^+$)

Intermediates (R)-2-[3-Chloro-4-(5-trifluoromethyl-furan-2-ylmethoxy)-benzyl]-morpholine-4-carboxylic acid tert-butyl ester The title compound was synthesized in analogy to example 84, intermediate, from (R)-2-(3-chloro-4-hydroxybenzyl)-morpholine-4-carboxylic acid tert-butyl ester (example 7, intermediate (a)) and 2-(bromomethyl)-5-(trifluoromethyl)furan as starting materials to give the compound as a colorless oil (82%).
MS (ISP): 493.4 (M+NH$_4^+$)

Example 89

(R)-2-[4-(1-Benzyl-1H-imidazol-2-ylmethoxy)-3-chloro-benzyl]-morpholine

The title compound was synthesized in analogy to example 83 from (R)-2-[4-(1-benzyl-1H-imidazol-2-ylmethoxy)-3-chloro-benzyl]-morpholine-4-carboxylic acid tert-butyl ester to give the title compound as a colorless oil (94%).
MS (ISP): 398.3 (M+H$^+$)

Intermediates (R)-2-[4-(1-Benzyl-1H-imidazol-2-ylmethoxy)-3-chloro-benzyl]-morpholine-4-carboxylic acid tert-butyl ester The title compound was synthesized in analogy to example 83, intermediate, from (R)-2-(3-chloro-4-hydroxybenzyl)-morpholine-4-carboxylic acid tert-butyl ester (example 7, intermediate (a)) and 1-benzyl-2-(chloromethyl)-1H-imidazole hydrochloride as starting materials to give the compound as a colorless oil (67%).
MS (ISP): 498.4 (M+H$^+$)

Example 90

(R)-2-[3-Chloro-4-(pyridin-2-ylmethoxy)-benzyl]-morpholine

The title compound was synthesized in analogy to example 83 from (R)-2-[3-chloro-4-(pyridin-2-ylmethoxy)-benzyl]-morpholine-4-carboxylic acid tert-butyl ester to give the title compound as a colorless oil (88%).
MS (ISP): 319.2 (M+H$^+$)

Intermediates (R)-2-[3-Chloro-4-(pyridin-2-ylmethoxy)-benzyl]-morpholine-4-carboxylic acid tert-butyl ester The title compound was synthesized in analogy to example 84, intermediate, from (R)-2-(3-chloro-4-hydroxybenzyl)-morpholine-4-carboxylic acid tert-butyl ester (example 7, intermediate (a)) and 2-(chloromethyl)pyridine hydrochloride as starting materials to give the compound as a colorless oil (62%).
MS (ISP): 419.3 (M+H$^+$)

Example 91

2-(2-Chloro-4-(R)-1-morpholin-2-ylmethyl-phenoxymethyl)-benzothiazole

The title compound was synthesized in analogy to example 83 from (R)-2-[4-(benzothiazol-2-ylmethoxy)-3-chloro-benzyl]-morpholine-4-carboxylic acid tert-butyl ester to give the title compound as a light yellow solid (96%).
MS (ISP): 375.4 (M+H$^+$)

Intermediates (R)-2-[4-(Benzothiazol-2-ylmethoxy)-3-chloro-benzyl]-morpholine-4-carboxylic acid tert-butyl ester
The title compound was synthesized in analogy to example 83, intermediate, from (R)-2-(3-chloro-4-hydroxy-benzyl)-morpholine-4-carboxylic acid tert-butyl ester (example 7, intermediate (a)) and 2-(bromomethyl)-1,3-benzothiazole as starting materials to give the compound as a light yellow solid (76%).
MS (ISP): 475.4 (M+H$^+$)

Example 92

(R)-2-[3-Chloro-4-(3,5-dimethyl-isoxazol-4-yl-methoxy)-benzyl]-morpholine

The title compound was synthesized in analogy to example 83 from (R)-2-(3-chloro-4-hydroxy-benzyl)-morpholine-4-carboxylic acid tert-butyl ester to give the title compound as a colorless oil (91%).
MS (ISP): 337.1 (M+H$^+$)

Intermediates (R)-2-(3-chloro-4-hydroxy-benzyl)-morpholine-4-carboxylic acid tert-butyl ester
The title compound was synthesized in analogy to example 83, intermediate, from (R)-2-(3-chloro-4-hydroxy-benzyl)-morpholine-4-carboxylic acid tert-butyl ester (example 7, intermediate (a)) and 4-(chloromethyl)-3,5-dimethylisoxazole as starting materials to give the compound as a colorless oil (80%).
MS (ISP): 437.4 (M+H$^+$)

Example 93

(R)-2-[3-Chloro-4-(2-methyl-thiazol-4-ylmethoxy)-benzyl]-morpholine

The title compound was synthesized in analogy to example 83 from (R)-2-[3-chloro-4-(2-methyl-thiazol-4-yl-methoxy)-benzyl]-morpholine-4-carboxylic acid tert-butyl ester to give the title compound as a colorless oil (94%).
MS (ISP): 339.1 (M+H$^+$)

Intermediates (R)-2-[3-Chloro-4-(2-methyl-thiazol-4-ylmethoxy)-benzyl]-morpholine-4-carboxylic acid tert-butyl ester
The title compound was synthesized in analogy to example 83, intermediate, from (R)-2-(3-chloro-4-hydroxy-benzyl)-morpholine-4-carboxylic acid tert-butyl ester (example 7, intermediate (a)) and 4-(chloromethyl)-2-methyl-1,3-thiazole as starting material to give the compound as a colorless oil (87%).
MS (ISP): 439.3 (M+H$^+$)

Example 94

(R)-2-(2-Chloro-3'-fluoro-4'-methyl-biphenyl-4-ylmethyl)-morpholine

The title compound was synthesized in analogy to example 83 from (R)-2-(2-chloro-3'-fluoro-4'-methyl-biphenyl-4-ylmethyl)-morpholine-4-carboxylic acid tert-butyl ester to give the title compound as a colorless oil (84%).
MS (ISP): 306.1 (M+H$^+$)

Intermediates (R)-2-(2-Chloro-3'-fluoro-4'-methyl-biphenyl-4-ylmethyl)-morpholine-4-carboxylic acid tert-butyl ester
The title compound was synthesized in analogy to example 80, intermediate (a), from (R)-2-(3-chloro-4-trifluoromethanesulfonyloxy-benzyl)-morpholine-4-carboxylic acid tert-butyl ester and 3-fluoro-4-methylbenzeneboronic acid to give the compound as a colorless oil (97%).
MS (ISP): 437.2 (M+NH$_4^+$)

Example 95

(R)-2-(3-Methoxymethyl-benzyl)-morpholine

The title compound was synthesized in analogy to example 83 from to give the compound as colorless oil (79%).
MS (ISP): 222.3 (M+H$^+$)

Intermediates a) (R)-2-(3-Methoxymethyl-benzyl)-morpholine-4-carboxylic acid tert-butyl ester
To the solution of 0.20 g (0.65 mmol) (R)-2-(3-hydroxymethyl-benzyl)-morpholine-4-carboxylic acid tert-butyl ester in 3 mL N,N-dimethylformamide 31 mg (0.71 mmol; 55% dispersion in mineral oil) sodium hydride was added. After 30 min. 81 µL (1.3 mmol) methyl iodide was added. After 2 h the reaction mixture was diluted with ethyl acetate and extracted with 10% aqueous ammonium chloride solution followed by brine. The organic layer was dried over magnesium sulfate, filtered and evaporated and the residue was purified by column chromatography on silica gel with n-hexane:ethyl acetate (1:1) as eluant to give the title compound as a colorless oil (76%).
MS (EI): 265.1 (M–C$_4$H$_8$)

b) (R)-2-(3-Hydroxymethyl-benzyl)-morpholine-4-carboxylic acid tert-butyl ester
The solution of 0.48 g (1.6 mmol) (R)-2-(3-formyl-benzyl)-morpholine-4-carboxylic acid tert-butyl ester in 5 mL methanol was treated with 36 mg (0.95 mmol) sodium borohydride. After 2 h the reaction was diluted with ethyl acetate and extracted with 10% aqueous sodium bicarbonate solution and brine. The organic layer was dried over magnesium sulfate, filtered and evaporated. Chromatography of the remaining residue on silica gel with n-hexane:ethyl acetate (1:1 v/v) gave the desired compound in form of a colorless oil (87%).
MS (ISP): 308.3 (M+H$^+$)

c) (R)-2-(3-Formyl-benzyl)-morpholine-4-carboxylic acid tert-butyl ester

The solution of 1.3 g (3.6 mmol) (R)-2-(3-bromo-benzyl)-morpholine-4-carboxylic acid tert-butyl ester in 80 mL diethyl ether was cooled down to −100° C. and treated dropwise with 2.6 mL (3.9 mmol; 1.5M solution in n-pentane) tert-butyllithium. After 15 min. 0.31 mL (4.0 mmol) N,N-dimethylformamide were added and the reaction stirred for another 1.5 h. The solution was poured on 10% aqueous ammonium chloride solution and extracted with ethyl acetate. The organic layer was washed with brine, dried over magnesium sulfate, filtered and evaporated. The residue was chromatographed on silica gel with n-hexane:ethyl acetate (2:1 v/v) as eluant to give the desired compound as colorless oil (43%).

MS (ISP): 323.4 (M+NH$_4^+$)

d) (R)-2-(3-Bromo-benzyl)-morpholine-4-carboxylic acid tert-butyl ester

To the solution of 4.1 g (16.0 mmol) (R)-2-(3-bromo-benzyl)-morpholine (example 15) in 50 mL dichloromethane, 4.2 g (19.2 mmol) di-tert-butyl dicarbonate and 0.20 g (16.4 mmol) 4-(dimethylamino)pyridine were added and the solution was stirred for 1 hour. The solvent was evaporated and the residue chromatographed over silica gel with n-hexane:ethyl acetate (4:1) as solvent to give the desired compound as a colorless oil (98%).

MS (EI): 35.05, 357.0 (M)

Example 96

(R)-2-(3-Cyclopropylmethoxymethyl-benzyl)-morpholine

The title compound was synthesized in analogy to example 83 from (R)-2-(3-cyclopropylmethoxymethyl-benzyl)-morpholine-4-carboxylic acid tert-butyl ester to give the compound as a colorless oil (97%).

MS (ISP): 262.2 (M+H$^+$)

Intermediates (R)-2-(3-Cyclopropylmethoxymethyl-benzyl)-morpholine-4-carboxylic acid tert-butyl ester The title compound was synthesized in analogy to example 95, intermediate (a), from (R)-2-(3-hydroxymethyl-benzyl)-morpholine-4-carboxylic acid tert-butyl ester and (bromomethyl)cyclopropane to give the compound as colorless oil (56%).

MS (EI): 304.1 (M−C$_2$H$_4$)

Example 97

Tablets containing the following ingredients can be manufactured in a conventional manner:

| Ingredients | Per tablet |
|---|---|
| Compound of formula I | 10.0-100.0 mg |
| Lactose | 125.0 mg |
| Maize starch | 75.0 mg |
| Talc | 4.0 mg |
| Magnesium stearate | 1.0 mg |

Example 98

Capsules containing the following ingredients can be manufactured in a conventional manner:

| Ingredients | Per capsule |
|---|---|
| Compound of formula I | 25.0 mg |
| Lactose | 150.0 mg |
| Maize starch | 20.0 mg |
| Talc | 5.0 mg |

Example 99

Injection solutions can have the following composition:

| Compound of formula I | 3.0 mg |
|---|---|
| Gelatine | 150.0 mg |
| Phenol | 4.7 mg |
| Water for injection solutions | ad 1.0 mL |

It is to be understood that the invention is not limited to the particular embodiments of the invention described above, as variations of the particular embodiments may be made and still fall within the scope of the appended claims.

What is claimed is:
1. A compound of formula (I):

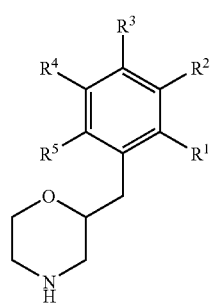

(I)

wherein
$R^1$, $R^2$, $R^3$, $R^4$ and $R^5$ are independently selected from hydrogen, alkyl, cycloalkyl, aryl, halogen, cyano, alkoxy, hydroxy, arylalkyl, arylalkoxy, alkenylalkoxy, cycloalkylalkoxy, cycloalkylalkoxyalkyl, hydroxyalkyl, alkoxyalkyl, hydroxyalkoxy, alkoxyalkoxy, alkenyl, alkenyloxy, N-hydroxy-amidinyl, aryloxyalkoxyalkyl, cyanoalkyl, cyanoalkoxy, alkinyloxy, alkinylalkoxy, heterocyclyl, heterocyclylalkyl, heterocyclylalkoxy, arylheterocyclylalkoxy, haloalkylarylheterocyclylalkoxy, haloalkylheterocyclylalkoxy, aralkylheterocyclylalkoxy, haloalkyl, alkylcarbonyl, alkylsulfonylphenyl, alkylsulfanyl, haloalkoxy and haloalkoxy substituted with hydroxyl and, wherein two of $R^1$, $R^2$, $R^3$, $R^4$ and $R^5$ optionally form together —(CH$_2$)$_n$—O— or —O—CF$_2$—O—;
n is 1, 2, 3 or 4;
with the proviso that at least one of $R^1$, $R^2$, $R^3$, $R^4$ and $R^5$ is not hydrogen and 2-(4-tert-butyl-benzyl)-morpholine is excluded;
and pharmaceutically acceptable salts and esters thereof.

2. The compound according to claim 1, wherein $R^1$ and $R^5$ are independently selected from hydrogen, halogen, hydroxyl, alkoxy and haloalkoxy.

3. The compound according to claim 1, wherein $R^1$ and $R^5$ are hydrogen.

4. The compound according to claim 1, wherein $R^2$ and $R^4$ are independently selected from hydrogen, alkyl, halogen, hydroxyalkyl, alkoxyalkyl, alkenyl, N-hydroxy-amidinyl, aryloxyalkoxyalkyl, heterocyclyl, heterocyclylalkyl and haloalkyl and, wherein $R^3$ and $R^4$ optionally form together —(CH$_2$)$_n$—O—.

5. The compound according to claim 1, wherein $R^2$ and $R^4$ are independently selected from hydrogen, alkyl, halogen, hydroxyalkyl, alkoxyalkyl, vinyl, N-hydroxy-amidinyl, aryloxyalkoxyalkyl, chloro-pyridinyl, pyridinylalkyl and trifluoromethyl and, wherein $R^3$ and $R^4$ optionally form together —(CH$_2$)$_2$—O—.

6. The compound according to claim 1, wherein one of $R^2$ and $R^4$ is hydrogen and the other one is alkyl, halogen or trifluoromethyl.

7. The compound according to claim 1, wherein $R^3$ is hydrogen, halogen, alkoxy, arylalkoxy, alkenylalkoxy, cycloalkylalkoxy, alkoxyalkoxy, alkenyloxy, cyanoalkoxy, heterocyclylalkoxy, haloalkoxy or haloalkoxy substituted with hydroxyl or, wherein $R^3$ and $R^4$ optionally form together —(CH$_2$)$_n$—O—.

8. The compound according to claim 1, wherein $R^3$ is hydrogen, alkoxy, cycloalkylalkoxy, methyl-isoxazolylalkoxy or trifluoromethoxy.

9. The compound according to claim 1, wherein the compound is of formula

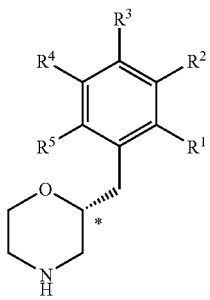

(Ia)

wherein the carbon atom C* is of the R configuration and $R^1$ to $R^5$ are defined as in any one of claims 1 to 8.

10. The compound according to claim 1, wherein the compound is of formula

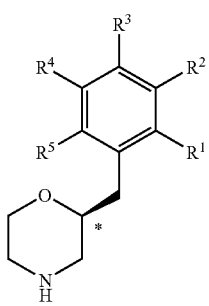

(Ib)

wherein the carbon atom C* is of the S configuration and $R^1$ to $R^5$ are defined as in any one of claims 1 to 8.

11. The compound according to claim 1, selected from 4-Bromo-2-(R)-1-morpholin-2-ylmethyl-phenol;
(R)-2-(4-Methoxy-3-trifluoromethyl-benzyl)-morpholine;
(R)-2-(2,5-Difluoro-4-methoxy-benzyl)-morpholine;
(R)-2-[3-Bromo-4-(5-methyl-isoxazol-3-ylmethoxy)-benzyl]-morpholine;
(R)-2-(2-Fluoro-4-methoxy-5-methyl-benzyl)-morpholine;
(R)-2-(4-Benzyloxy-3-bromo-benzyl)-morpholine;
(R)-2-{4-[((E)-But-2-enyl)oxy]-3-chloro-benzyl}-morpholine;
(R)-2-(4-Fluoro-3-trifluoromethyl-benzyl)-morpholine;
(R)-2-(3-Bromo-4-methoxy-benzyl)-morpholine;
(R)-2-(4-Ethoxy-3-trifluoromethyl-benzyl)-morpholine;
(R)-2-(4-Cyclopropylmethoxy-3-trifluoromethyl-benzyl)-morpholine;
(R)-2-(4-Methoxy-3-methyl-benzyl)-morpholine;
(R)-2-(2-Fluoro-5-trifluoromethyl-benzyl)-morpholine;
(R)-2-(3-Trifluoromethyl-benzyl)-morpholine;
(R)-2-(3-Bromo-benzyl)-morpholine;
(R)-2-(3-Chloro-benzyl)-morpholine;
(R)-2-[4-Methoxy-3-(1-methoxy-ethyl)-benzyl]-morpholine;
(R)-2-(3,4-Dichloro-benzyl)-morpholine;
(R)-2-(4-Allyloxy-3-bromo-benzyl)-morpholine;
(R)-2-[3-Chloro-4-(5-methyl-isoxazol-3-ylmethoxy)-benzyl]-morpholine;
(R)-2-(4-Allyloxy-3-chloro-benzyl)-morpholine;
(R)-2-(3-Bromo-4-ethoxy-benzyl)-morpholine;
(R)-2-(3-Bromo-4-cyclopropylmethoxy-benzyl)-morpholine;
(R)-2-(4-Methoxy-3-vinyl-benzyl)-morpholine;
N-Hydroxy-2-methoxy-5-(R)-1-morpholin-2-ylmethyl-benzamidine;
(R)-2-[3-(2-Phenoxy-ethoxymethyl)-benzyl]-morpholine;
(S)-2-(3-Chloro-4-cyclopropylmethoxy-benzyl)-morpholine;
(R)-2-(3-Chloro-4-ethoxy-benzyl)-morpholine;
2-(R)-1-Morpholin-2-ylmethyl-phenol;
(R)-2-(4-Chloro-3-methyl-benzyl)-morpholine;
(R)-2-[3-(2-Pyridin-4-yl-ethyl)-benzyl]-morpholine;
(2-Bromo-4-(R)-(1-morpholin-2-ylmethyl)-phenoxy)-acetonitrile;
(R)-2-(3-Methyl-benzyl)-morpholine;
(R)-2-(2-Difluoromethoxy-benzyl)-morpholine;
(S)-2-(3-Bromo-4-methoxy-benzyl)-morpholine;
(R)-2-[3-Bromo-4-(2-methoxy-ethoxy)-benzyl]-morpholine;
(R)-2-[4-(2,2,2-Trifluoro-ethoxy)-3-trifluoromethyl-benzyl]-morpholine;
(R)-2-(3-Bromo-4-prop-2-ynyloxy-benzyl)-morpholine;
(R)-2-(3-Chloro-4-prop-2-ynyloxy-benzyl)-morpholine;
(R)-2-[3-Chloro-4-(2,2,2-trifluoro-ethoxy)-benzyl]-morpholine;
(R)-2-(3-Vinyl-benzyl)-morpholine;
(R)-2-(5-Chloro-2-fluoro-benzyl)-morpholine;
(R)-2-[3-Chloro-4-(2-methoxy-ethoxy)-benzyl]-morpholine;
(R)-2-[3-Chloro-4-(pyridin-3-ylmethoxy)-benzyl]-morpholine;
(R)-2-[3-(6-Chloro-pyridin-3-yl)-benzyl]-morpholine;
(R)-2-(3-Bromo-4-methoxy-5-methyl-benzyl)-morpholine;
(R)-2-(3-Fluoro-4-methoxy-benzyl)-morpholine;
(R)-2-[3-(2-Pyridin-3-yl-ethyl)-benzyl]-morpholine;
1-(2-Methoxy-5-(R)-1-morpholin-2-ylmethyl-phenyl)-ethanol;

(R)-2-(7-Bromo-2,3-dihydro-benzofuran-5-ylmethyl)-morpholine;
2,4-Dibromo-6-(R)-1-morpholin-2-ylmethyl-phenol;
(R)-2-[3-Chloro-4-(tetrahydro-furan-2-ylmethoxy)-benzyl]-morpholine;
(R)-2-(3-Ethyl-4-methoxy-benzyl)-morpholine;
(R)-2-[3-(3,5-dimethyl-isoxazol-4-yl)-4-methoxybenzyl]-morpholine;
1-(2-Methoxy-5-(R)-1-morpholin-2-ylmethyl-phenyl)-ethanone;
(R)-2-(3-Iodo-4-methoxy-benzyl)-morpholine;
(R)-2-(5-Bromo-2,4-dimethoxy-benzyl)-morpholine;
(R)-2-(3-Chloro-4-propyloxy-benzyl)-morpholine;
(R)-2-(3-Bromo-4-cyclopentyloxy-benzyl)-morpholine;
(R)-2-(5-Bromo-2-difluoromethoxy-benzyl)-morpholine;
(R)-2-(3-Bromo-4-butoxy-benzyl)-morpholine;
(R)-2-(3-Bromo-4-isopropoxy-benzyl)-morpholine;
(R)-2-(3-Bromo-4-propoxy-benzyl)-morpholine;
(R)-2-(3-Chloro-4-methoxy-benzyl)-morpholine;
(R)-2-(5-Chloro-2-fluoro-4-methoxy-benzyl)-morpholine;
(R)-2-(2,2-Difluoro-benzo[1,3]dioxol-4-ylmethyl)-morpholine;
(R)-2-(2-Fluoro-3-trifluoromethyl-benzyl)-morpholine;
(R)-2-[3-(2-Pyridin-2-yl-ethyl)-benzyl]-morpholine;
2-(3-Ethyl-benzyl)-morpholine;
2-(2-Fluoro-3-methyl-benzyl)-morpholine;
2-(4-Fluoro-3-methylbenzyl)-morpholine;
2-(3-Bromo-4-methoxy-benzyl)-morpholine;
2-(3-Bromobenzyl)-morpholine;
(S)-2-(3-Trifluoromethyl-benzyl)-morpholine;
2-(2-Difluoromethoxy-benzyl)-morpholine;
2-(3-Methyl-benzyl)-morpholine;
2-(3-Trifluoromethyl-benzyl)-morpholine;
(R)-4-(2,5-Difluoro-4-(R)-(1-morpholin-2-ylmethyl)-phenoxy)-1,1,1-trifluoro-butan-2-ol;
(R)-2-[2,5-Difluoro-4-(5-methyl-isoxazol-3-ylmethoxy)-benzyl]-morpholine;
(R)-2-(2-Chloro-4'-methanesulfonyl-biphenyl-4-ylmethyl)-morpholine;
(R)-2-(3-Chloro-4-methylsulfanyl-benzyl)-morpholine;
(R)-2-(3-Cyclopropyl-4-methoxy-benzyl)-morpholine;
(R)-2-{3-Chloro-4-[5-(4-methoxy-phenyl)-[1,2,4]oxadiazol-3-ylmethoxy]-benzyl}-morpholine;
(R)-2-[3-Chloro-4-(2-phenyl-5-methyl-oxazol-4-ylmethoxy)-benzyl]-morpholine;
(R)-2-[3-Chloro-4-(5-phenyl-[1,2,4]oxadiazol-3-ylmethoxy)-benzyl]-morpholine;
(R)-2-{3-Chloro-4-[5-(4-trifluoromethyl-phenyl)-[1,2,4]oxadiazol-3-ylmethoxy]-benzyl}-morpholine;
(R)-2-{3-Chloro-4-[2-(4-chloro-phenyl)-thiazol-4-ylmethoxy]-benzyl}-morpholine;
(R)-2-[3-Chloro-4-(5-trifluoromethyl-furan-2-ylmethoxy)-benzyl]-morpholine; (R)-2-[4-(1-Benzyl-1H-imidazol-2-ylmethoxy)-3-chloro-benzyl]-morpholine;
(R)-2-[3-Chloro-4-(pyridin-2-ylmethoxy)-benzyl]-morpholine;
2-(2-Chloro-4-(R)-(1-morpholin-2-ylmethyl)-phenoxymethyl)-benzothiazole;
(R)-2-[3-Chloro-4-(3,5-dimethyl-isoxazol-4-ylmethoxy)-benzyl]-morpholine;
(R)-2-[3-Chloro-4-(2-methyl-thiazol-4-ylmethoxy)-benzyl]-morpholine;
(R)-2-(2-Chloro-3'-fluoro-4'-methyl-biphenyl-4-ylmethyl)-morpholine;
(R)-2-(3-Methoxymethyl-benzyl)-morpholine; and
(R)-2-(3-Cyclopropylmethoxymethyl-benzyl)-morpholine.

12. The compound according to claim 1, selected from
(R)-2-(4-Methoxy-3-trifluoromethyl-benzyl)-morpholine;
(R)-2-[3-Bromo-4-(5-methyl-isoxazol-3-ylmethoxy)-benzyl]-morpholine;
(R)-2-(4-Ethoxy-3-trifluoromethyl-benzyl)-morpholine;
(R)-2-(4-Cyclopropylmethoxy-3-trifluoromethyl-benzyl)-morpholine;
(R)-2-(4-Methoxy-3-methyl-benzyl)-morpholine;
(R)-2-(3-Trifluoromethyl-benzyl)-morpholine;
(R)-2-(3-Chloro-benzyl)-morpholine;
(R)-2-[3-Chloro-4-(5-methyl-isoxazol-3-ylmethoxy)-benzyl]-morpholine;
(R)-2-(3-Bromo-4-ethoxy-benzyl)-morpholine;
(R)-2-[3-Chloro-4-(2,2,2-trifluoro-ethoxy)-benzyl]-morpholine;
(R)-2-(3-Chloro-4-ethoxy-benzyl)-morpholine;
(2-Bromo-4-(R)-(1-morpholin-2-ylmethyl)-phenoxy)-acetonitrile;
(R)-4-(2,5-Difluoro-4-(R)-(1-morpholin-2-ylmethyl)-phenoxy)-1,1,1-trifluoro-butan-2-ol; and
(R)-2-[3-Chloro-4-(2,2,2-trifluoro-ethoxy)-benzyl]-morpholine.

13. A pharmaceutical composition, comprising a therapeutically effective amount of a compound according to claim 1 and a therapeutically inert carrier.

14. The pharmaceutical composition according to claim 13, comprising further a therapeutically effective amount of a lipase inhibitor.

* * * * *